United States Patent
Cook et al.

(10) Patent No.: US 7,235,656 B2
(45) Date of Patent: Jun. 26, 2007

(54) ANXIOLYTIC AGENTS WITH REDUCED SEDATIVE AND ATAXIC EFFECTS

(75) Inventors: James M. Cook, Whitefish Bay, WI (US); Qi Huang, Moorpark, CA (US); Xiaohui He, San Diego, CA (US); Xioayan Li, Milwaukee, WI (US); Jianming Yu, Milwaukee, WI (US); Dongmei Han, Houston, TX (US)

(73) Assignee: WiSys Technology Foundation, Inc., Madison, WI (US)

( * ) Notice: Subject to any disclaimer, the term of this patent is extended or adjusted under 35 U.S.C. 154(b) by 0 days.

(21) Appl. No.: 11/458,739

(22) Filed: Jul. 20, 2006

(65) Prior Publication Data

US 2007/0054881 A1     Mar. 8, 2007

Related U.S. Application Data

(62) Division of application No. 10/402,538, filed on Mar. 28, 2003, now Pat. No. 7,119,196.

(60) Provisional application No. 60/368,408, filed on Mar. 28, 2002, now abandoned.

(51) Int. Cl.
  *C07D 495/14*   (2006.01)
  *C07D 521/00*   (2006.01)

(52) U.S. Cl. .................................................. 540/560

(58) Field of Classification Search ................. 540/560
See application file for complete search history.

(56) References Cited

U.S. PATENT DOCUMENTS 4,401,597 A * 8/1983 Walser et al. ................ 540/568
4,440,685 A * 4/1984 Walser et al. ................ 540/562
4,900,729 A * 2/1990 Stransky et al. ............. 514/220

* cited by examiner

*Primary Examiner*—Bruck Kifle
(74) *Attorney, Agent, or Firm*—Roger P. Zimmerman; Mirick O'Connell DeMallie & Lougee LLP

(57) ABSTRACT

Orally active benzodiazepine derivatives and their salts are disclosed. These compounds and their salts have anxiolytic and anticonvulsant activity with reduced sedative/hypnotic/muscle relaxant/ataxic effects.

8 Claims, No Drawings

ANXIOLYTIC AGENTS WITH REDUCED SEDATIVE AND ATAXIC EFFECTS

CROSS-REFERENCE TO RELATED APPLICATIONS

This application is a divisional of U.S. application Ser. No. 10/402,538 filed on Mar. 28, 2003 now U.S. Pat. No. 7,119,196, which claims benefit of U.S. Provisional Patent Application No. 60/368,408 filed Mar. 28, 2002, both of which are incorporated herein in its entirety as if fully set forth herein.

STATEMENT REGARDING FEDERALLY SPONSORED RESEARCH OR DEVELOPMENT

This invention was made with Government support under NIMH grant number MH46851. The Government has certain rights to this invention.

BACKGROUND OF THE INVENTION

The present invention relates to a class of benzodiazepine derivatives which possess anxiolytic activity with decreased sedative, hypnotic, and ataxic side effects.

The most frequently prescribed medication for treatment of anxiety disorders (such as phobias, obsessive compulsive disorders) and seizure disorders are benzodiazepines such as diazepam (Valium), triazolam (Halcion), midazolam (Versed), lorazepam (Ativan), chlordiazepoxide (Librium), alprazolam (Xanax), and other benzodiazepine-based medications. However, these benzodiazepine-based medications have side effects such as drowsiness, sedation, motor incoordination, memory impairment, potentiation of effects of alcohol, tolerance and dependence, and abuse potential. Buspirone, tandospirone, and other serotonergic agents have been developed as anxiolytics with a potentially reduced profile of side effects. However, while these medications do show a reduced profile of side effects, they have other characteristics which make them less than ideal for treatment of anxiety disorders. In some cases, these agents cause anxiety before a therapeutic dose can be obtained or require dosing of the drug for several days before a therapeutic effect is seen. Development of anxiolytics with even fewer side effects is desired.

Receptors for the major inhibitory neurotransmitter, gamma-aminobutyric acid (GABA), are divided into three main classes: (1) $GABA_A$ receptors, which are members of the ligand-gated ion channel superfamily; (2) $GABA_B$ receptors, which may be members of the G-protein linked receptor superfamily; and (3) $GABA_C$ receptors, also members of the ligand-gated ion channel superfamily, but their distribution is confined to the retina. Benzodiazepine receptor ligands do not bind to $GABA_B$ and $GABA_C$ receptors. Since the first cDNAs encoding individual $GABA_A$ receptor subunits were cloned the number of known members of the mammalian family has grown to 21 including $\alpha$, $\beta$, and $\gamma$ subunits ($6\alpha$, $4\beta$, $4\gamma$, $1\delta$, $1\epsilon$, $1\pi$, $1\theta$, and $3\rho$).

Subtype assemblies containing an $\alpha 1$ subunit ($\alpha 1\beta 2\gamma 2$) are present in most areas of the brain and are thought to account for 40-50% of $GABA_A$ receptors in the rat. Subtype assemblies containing $\alpha 2$ and $\alpha 3$ subunits respectively are thought to account for about 25% and 17% $GABA_A$ receptors in the rat. Subtype assemblies containing an $\alpha 5$ subunit ($\alpha 5\beta 3\gamma 2$) are expressed predominately in the hippocampus and cortex and are thought to represent about 4% of $GABA_A$ receptors in the rat.

A characteristic property of all known $GABA_A$ receptors is the presence of a number of modulatory sites, one of which is the benzodiazepine binding site. The benzodiazepine binding site is the most explored of the $GABA_A$ receptor modulatory sites, and is the site through which benzodiazepine-based anxiolytic drugs exert their effect. Before the cloning of the $GABA_A$ receptor gene family, the benzodiazepine binding site was historically subdivided into two subtypes, BENZODIAZEPINE1 and BENZODIAZEPINE2, on the basis of radioligand binding studies on synaptosomal rat membranes. The BENZODIAZEPINE1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain, as stated.

Two other major populations are the ($\alpha 2\beta 2/3\gamma 2$ and $\alpha 3\beta 2/3\gamma 2/3$ subtypes. Together these constitute approximately a further 35% of the total $GABA_A$ receptor population. Pharmacologically this combination appears to be equivalent to the BENZODIAZEPINE2 subtype as defined previously by radioligand binding, although the BENZODIAZEPINE2 subtype may also include certain $\alpha 5$-containing subtype assemblies. The physiological role of these subtypes has hitherto been unclear because no sufficiently selective agonists or antagonists were known.

It is now believed that agents acting as benzodiazepine agonists at $GABA_A/\alpha 2$, $GABA_A/\alpha 3$, and/or $GABA_A/\alpha 5$ receptors, will possess desirable anxiolytic properties. Compounds which are modulators of the benzodiazepine binding site of the $GABA_A$ receptor by acting as benzodiazepine agonists are referred to hereinafter as "$GABA_A$ receptor agonists." The $GABA_A/\alpha 1$-selective ($\alpha 1\beta 2\gamma 2$) agonists alpidem and zolpidem are clinically prescribed as hypnotic agents, suggesting that at least some of the sedation associated with known anxiolytic drugs which act at the BENZODIAZEPINE 1 binding site is mediated through $GABA_A$ receptors containing the $\alpha 1$ subunit. Accordingly, it is considered that $GABA_A/\alpha 2$, $GABA_A/\alpha 3$, and/or $GABA_A/\alpha 5$ receptor agonists rather than $GABA_A/\alpha 1$ receptors will be effective in the treatment of anxiety with a reduced propensity to cause sedation. For example, QH-ii-066 binds with high affinity to $GABA_A/\alpha 0.5$ receptors (Ki<10 nM), intermediate affinity to $GABA_A/\alpha 2$ and $GABA_A/\alpha 3$ (Ki<50 nM), and lower affinity to $GABA_A/\alpha 1$ receptors (Ki>70 nM), unlike diazepam which binds with high affinity to all four diazepam-sensitive $GABA_A$ receptors (Ki<25 nM), as disclosed in Huang, et al., *J. Med. Chem.* 2000, 43, 71-95. Also, agents which are antagonists or inverse agonists at $\alpha 1$ receptors might be employed to reverse sedation or hypnosis caused by $\alpha 1$ agonists.

Since the compounds of the present invention exhibit increased agonist efficacy at only a few $GABA_A$ types of receptors and/or selective efficacy at one or more ion channels and have been shown to be effective in animal models of anxiety and seizures, with reduced severity and/or incidence of side effects, they are useful in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, general anxiety disorder, attention deficit disorders, stress disorders including post-traumatic and acute stress disorder, and generalized or substance-induced anxiety disorder, neuroses, convulsions; migraine; depressive or bipolar disorders, for example single episode or recurrent major depressive disorder, dysthymic disorder, bipolar I and bipolar II manic disorders, and cyclothymic disorder, psychotic disorders including schizophrenia.

SUMMARY OF THE INVENTION

In consideration of this situation, the problem to be solved by the present invention is to provide a medication which can be used for the treatment of anxiety neurosis, general anxiety disorder, panic disorder, phobias, obsessive-compulsive disorders, schizophrenia, post-cardiac trauma stress disorders, depression disorders, psychosomatic disorders, and other psychoneurotic disorders, eating disorders, menopausal disorders, infantile autism and other disorders, and also emesis with fewer side effects.

The present inventors engaged in repeated extensive studies to develop a superior medication free from the above problems. They found that the compounds of the present invention, that is, the novel benzodiazepine derivatives and their salts, have beneficial pharmacological and behavioral effects, that is, the compounds of the present invention show anxiolytic and anticonvulsant activity with greatly decreased or no sedative/hypnotic/muscle relaxant/ataxic side effects.

The compounds described in the present invention have been synthesized based on a modified version of the computer modeling disclosed in Cook, et al *J. Med. Chem.*, 1996, 39, 1928-1934. These compounds obtained by modifying elements, described herein, of the known benzodiazepine agents, have increased binding selectivity for the $GABA_A$/$\alpha 2$, $GABA_A$/$\alpha 3$, and/or $GABA_A$/$\alpha 5$ receptors described above, and/or altered efficacy at one or more $GABA_A$ receptors described above, and/or altered selectivity at one or more ion channels. These compounds, which have been tested in animal models of anxiety in rats and seizures in mice, and side effect models in rats, have been found to be orally active and have anxiolytic and anticonvulsant activity, with reduced severity and/or incidence of side effects.

One object of the present invention is to identify medications containing these benzodiazepine derivatives or their pharmaceutically acceptable salts as essential ingredients that are usable for the treatment of anxiety neurosis, phobias, obsessive-compulsive disorders, panic disorder, generalized anxiety disorder, schizophrenia, post-cardiac trauma stress disorders, depression disorders, psychosomatic disorders, and other psychoneurotic disorders, eating disorders, menopausal disorders, infantile autism, and other disorders.

The present invention describes a class of benzodiazepine derivatives which possess desirable enhanced agonist efficacy at various $GABA_A$ receptors and desirable behavioral profile with respect to anxiolytic and anticonvulsant efficacy and reduced side effect efficacy. The compounds in accordance with the present invention have agonist efficacy at the $GABA_A$/$\alpha 2$, $GABA_A$/$\alpha 3$, and $GABA_A$/$\alpha 5$ receptors. The compounds of this invention have anxiolytic and anticonvulsant effects with decreased sedative-hypnotic activity.

The present invention provides a compound of formula I, or a salt or prodrug thereof,

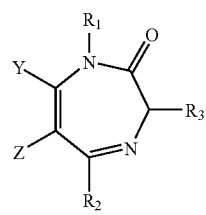

(I)

wherein Y and Z are taken together with the two intervening carbon atoms to form a ring selected from phenyl and thienyl, which ring is substituted at the C(7) position with at least the substituent —C≡C—R, where R is H, $Si(CH_3)_3$, t-butyl, isopropyl, methyl, or cyclopropyl; $R_1$ is one of H, $CH_3$, $C_2H_4N(C_2H_5)_2$, $CH_2CF_3$, $CH_2C\equiv CH$, or an alkyl cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position; and $R_3$ is one of H, OH, $OCON(CH_3)_2$, $COOCH_3$, or $COOC_2H_5$. Preferred compounds according to formula I include:

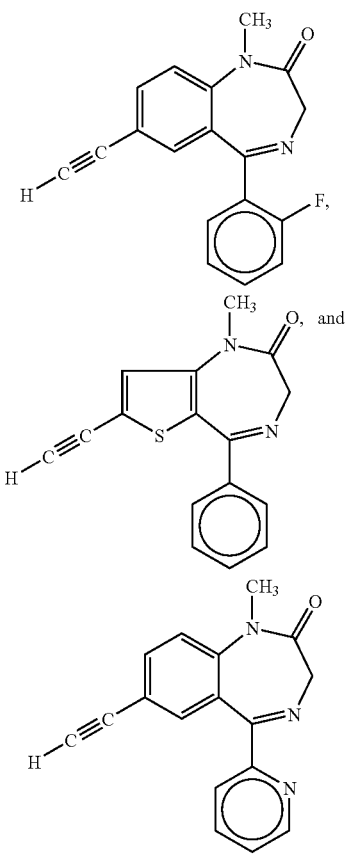

The invention provides in another aspect a compound of formula II, or a salt or prodrug thereof,

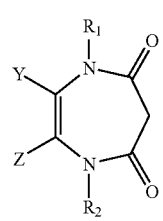

(II)

wherein Y and Z are taken together with the two intervening carbon atoms to form a ring selected from phenyl and thienyl, which ring is substituted at the C(7) position with at least the substituent —C≡C—R, where R is H, $Si(CH_3)_3$, t-butyl, isopropyl, methyl, or cyclopropyl; $R_1$ is one of H, CH₃, C₂H₄N(C₂H₅)₂, CH₂CF₃, CH₂C≡CH, or an alkyl cyclopropyl; and R₂ is a substituted or unsubstituted at least partially unsaturated 5 or 6 membered cyclic or heterocyclic ring, wherein if substituted the substituent is one or more of F, Cl, Br, or NO₂ at the 2'-position. Preferred compounds according to formula II include:

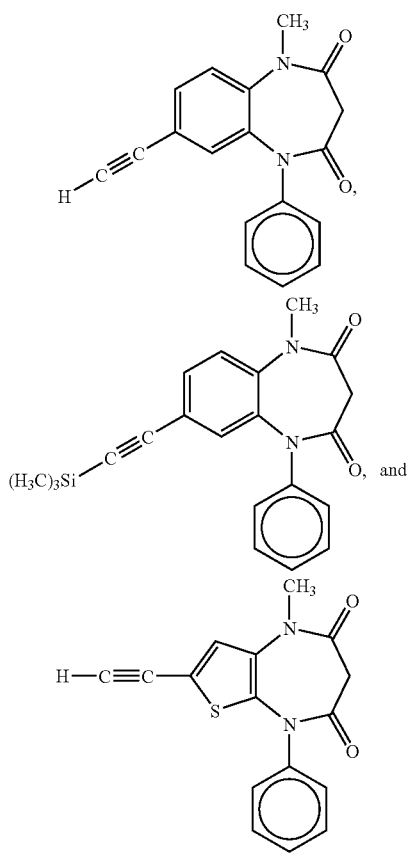

The present invention provides in yet another aspect a compound of formula III, or a salt or prodrug thereof,

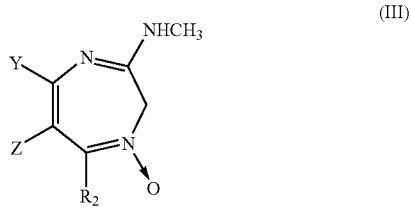
(III)

wherein Y and Z are taken together with the two intervening carbon atoms to form a ring selected from phenyl and thienyl, which ring is substituted at the C(7) position with at least the substituent —C≡C—R, where R is H, Si(CH₃)₃, t-butyl, isopropyl, methyl, or cyclopropyl; and R₂ is a substituted or unsubstituted at least partially unsaturated 5 or 6 membered cyclic or heterocyclic ring, wherein if substituted the substituent is one or more of F, Cl, Br, or NO₂ at the 2'-position. Preferred compounds according to the formula III include:

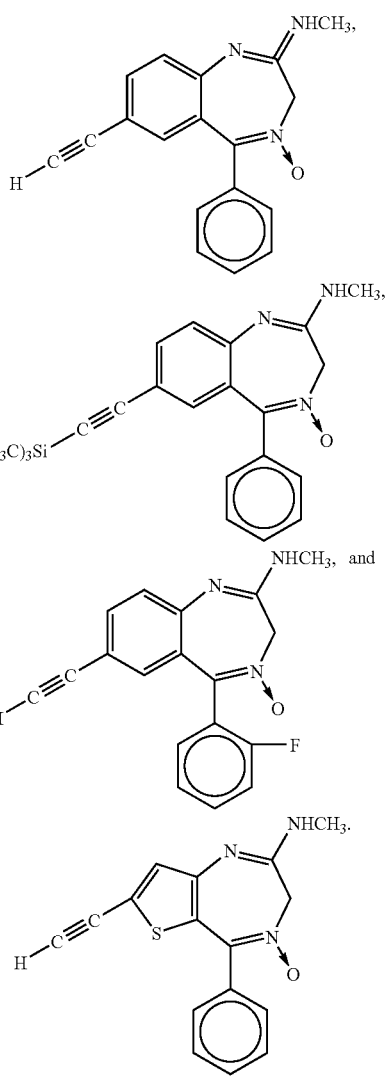

Further, the present invention provides a compound of formula IV, or a salt or prodrug thereof.

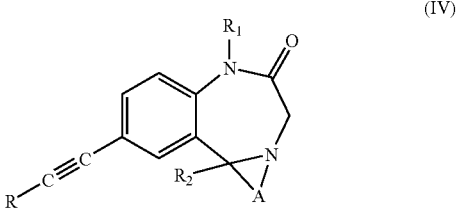
(IV)

wherein R is H, Si(CH₃)₃, t-butyl, isopropyl, methyl, or cyclopropyl; R₁ is one of H, CH₃, C₂H₄N(C₂H₅)₂, CH₂CF₃, CH₂C≡CH, or an alkyl cyclopropyl; R₂ is a substituted or unsubstituted at least partially unsaturated 5 or 6 membered cyclic or heterocyclic ring, wherein if substituted the substituent is one or more of F, Cl, Br, or NO₂ at the 2'-position; and A is an ethoxide or a propoxide. Preferred compounds according to the formula IV include:

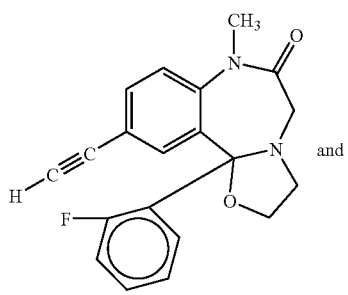

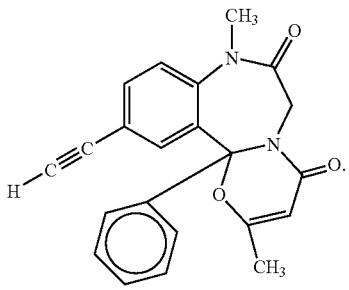

In a still further aspect, the present invention provides a compound of formula V, or a salt or prodrug thereof,

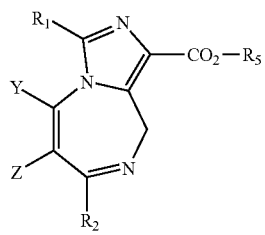

(V)

wherein Y and Z are taken together with the two intervening carbon atoms to form a ring selected from phenyl and thienyl, which ring is substituted at the C(8) position with at least the substituent —C≡C—R, where R is H, $Si(CH_3)_3$, t-butyl, isopropyl, methyl, or cyclopropyl; $R_1$ is one of H, $CH_3$, $CF_3$, $CH_2CH_3$, $CH_2CF_3$, $CH_2C≡CH$, an alkyl, or cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position; and $R_5$ is a branched or straight chain $C_1$ to $C_4$ halogenated or unhalogenated alkyl or a methyl cyclopropyl. Preferred compounds according to formula V include:

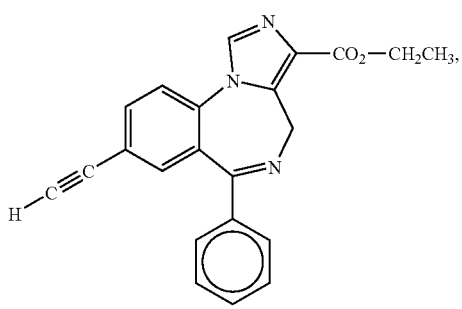

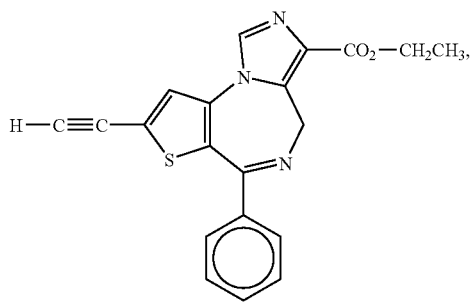

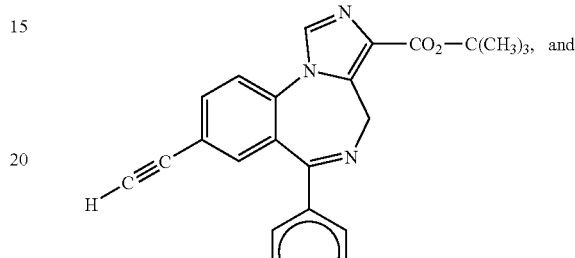

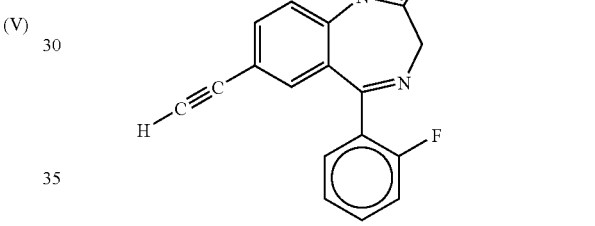

In yet another aspect, the present invention provides a compound of formula VI, or a salt or prodrug thereof,

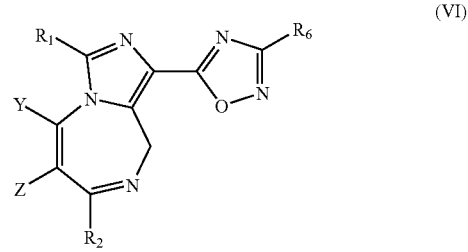

(VI)

wherein Y and Z are taken together with the two intervening carbon atoms to form a ring selected from phenyl and thienyl, which ring is substituted at the C(8) position with at least the substituent —C≡C—R, where R is H, $Si(CH_3)_3$, t-butyl, isopropyl, methyl, or cyclopropyl; $R_1$ is one of H, $CH_3$, $CF_3$, $CH_2CH_3$, $CH_2CF_3$, or cyclopropyl; $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position; and $R_6$ is a branched or straight chain $C_1$ to $C_4$ alkyl or a methyl cyclopropyl. Preferred compounds according to formula VI include:

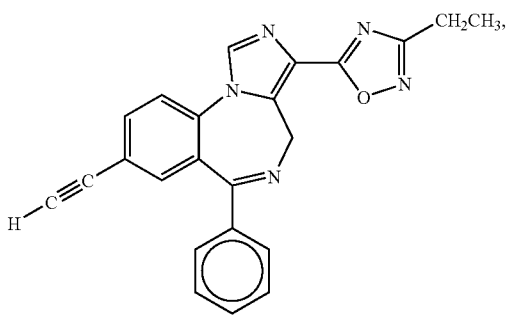

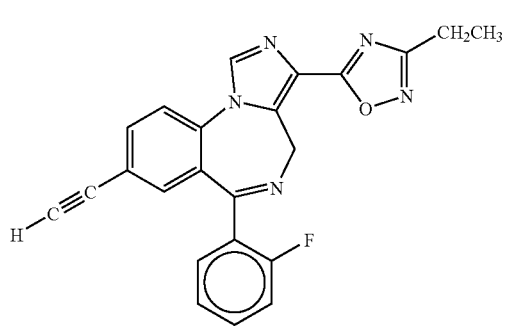

The present invention also provides a compound of formula VII, or a salt or prodrug thereof,

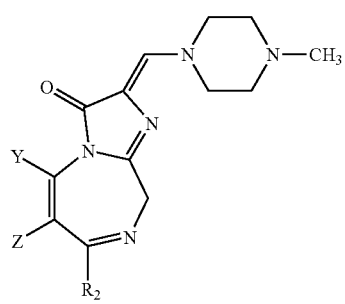

(VII)

wherein Y and Z are taken together with the two intervening carbon atoms to form a ring selected from phenyl and thienyl, which ring is substituted at the C(8) position with at least the substituent —C≡C—R, where R is H, $Si(CH_3)_3$, t-butyl, isopropyl, methyl, or cyclopropyl; and $R_2$ is a substituted or unsubstituted at least partially unsaturated 5 or 6 membered cyclic or heterocyclic ring, wherein if substituted the substituent is one or more of F, Cl, Br, or $NO_2$ at the 2'-position. Preferred compounds according to formula VII include:

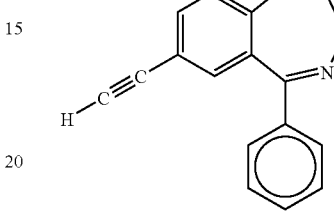

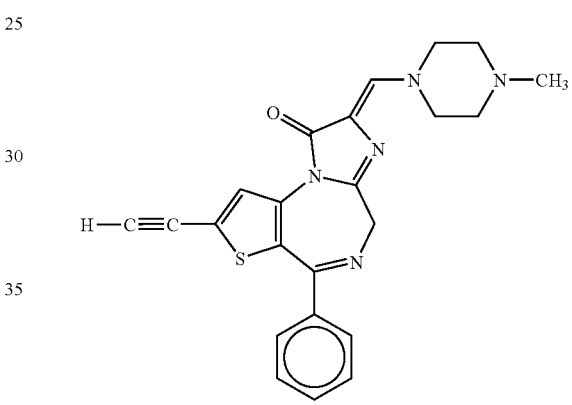

The present invention still further provides a compound of formula VIII, or a salt or prodrug thereof,

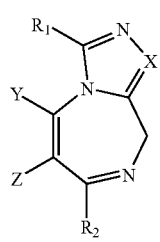

(VIII)

wherein Y and Z are taken together with the two intervening carbon atoms to form a ring selected from phenyl and thienyl, which ring is substituted at the C(8) position with at least the substituent —C≡C—R, where X is N or CH, where R is H, $Si(CH_3)_3$, t-butyl, isopropyl, methyl, or cyclopropyl; $R_1$ is H, $CH_3$, $CF_3$, $CH_2CH_3$, $CH_2CF_3$, or cyclopropyl; $R_2$ is a substituted or unsubstituted at least partially unsaturated 5 or 6 membered cyclic or heterocyclic ring, wherein if substituted the substituent is one or more of F, Cl, Br, or NO₂ at the 2'-position. Preferred compounds according to formula VIII include:

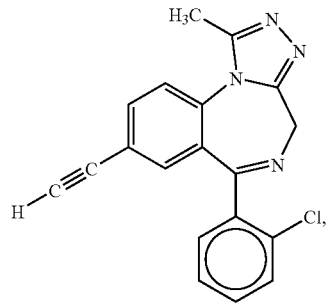

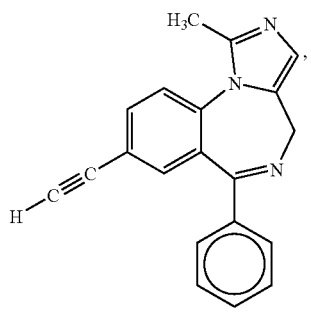

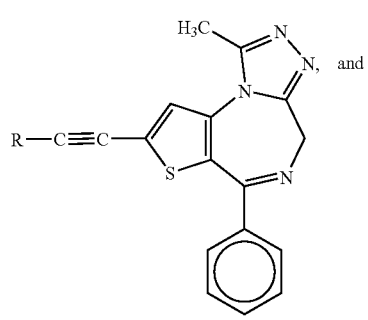
and

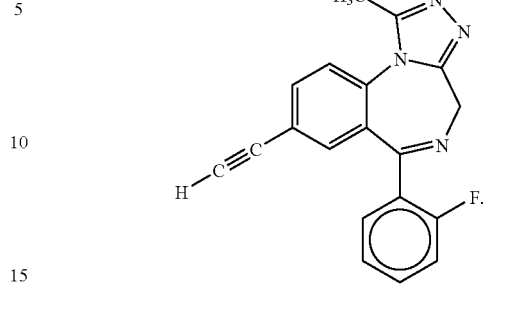

Yet another aspect of the present invention provides a compound of formula IX, or a salt or prodrug thereof,

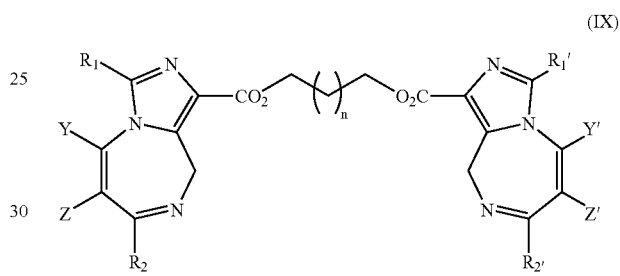

wherein n is 0 to 4; Y and Z are taken together with the two intervening carbon atoms to form a ring selected from phenyl and thienyl, which ring is substituted at the C(8) position with at least the substituent —C≡C—R, where R is H, Si(CH₃)₃, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, Si(CH₃)₃, t-butyl, isopropyl, methyl, or cyclopropyl; $R_1$ and $R_1'$ are independently one of H, CH₃, CF₃, CH₂CF₃, CH₂CH₃, or cyclopropyl; and $R_2$ and $R_2'$ are independently a substituted or unsubstituted at least partially unsaturated 5 or 6 membered cyclic or heterocyclic ring, wherein if substituted the substituent is one or more of F, Cl, Br, or NO₂ at the 2'-position. Preferred compounds according to formula IX include:

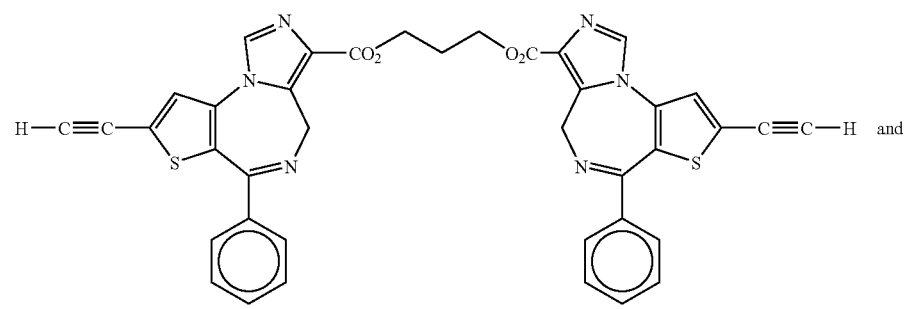
and

-continued

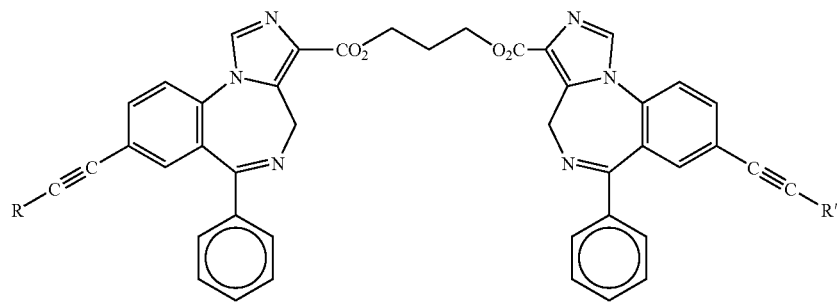

R is H or Si(CH$_3$)$_3$
R' is H or Si(CH$_3$)$_3$

A still further aspect of the present invention provides a compound of formula X, or a salt or prodrug thereof,

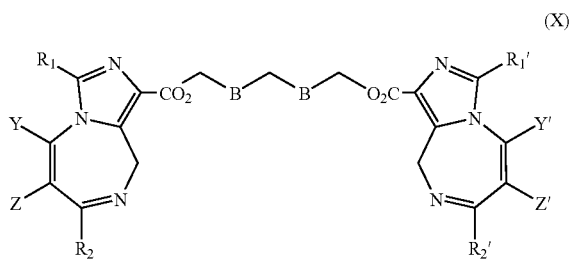

wherein Y and Z are taken together with the two intervening carbon atoms to form a ring selected from phenyl and thienyl, which ring is substituted at the C(8) position with at least the substituent —C≡C—R, where R is H, Si(CH$_3$)$_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R' where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O or NH and wherein —BCH$_2$B— is optionally replaced with —N(R$_7$)—N(R$_7$)—, where R$_7$ is one of H, CH$_3$, alkyl, or cycloalkyl. Preferred compounds according to formula X include:

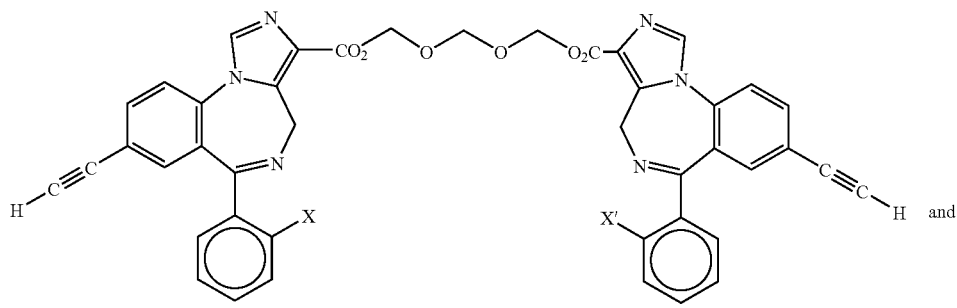

X and X' are each independently H or F

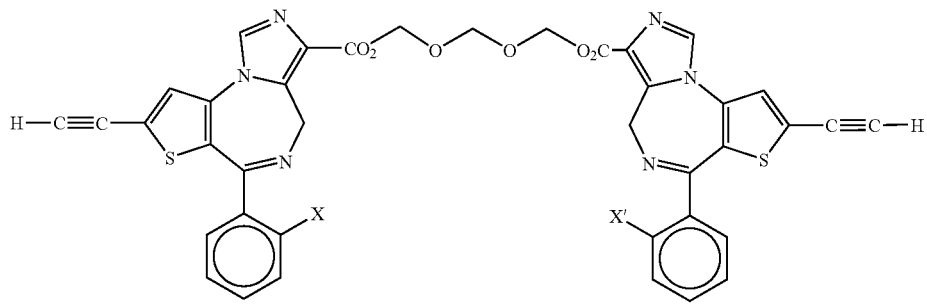

X and X' are each independently H or F

The present invention further provides a compound of formula XI, or a salt or prodrug thereof,

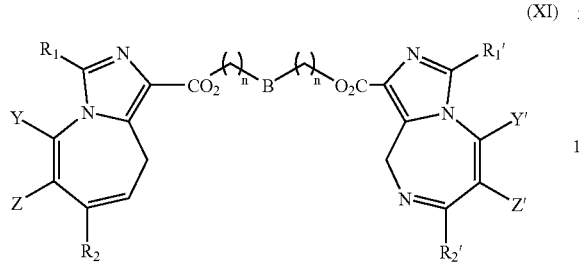

(XI)

wherein n is 1 or 2; wherein Y and Z are taken together with the two intervening carbon atoms to form a ring selected from phenyl and thienyl, which ring is substituted at the C(8) position with at least the substituent —C≡C—R, where R is H, $Si(CH_3)_3$, t-butyl, isopropyl, methyl, or cyclopropyl; Y' and Z' are taken together with the two intervening carbon atoms to form a ring selected from phenyl and thienyl, which ring is substituted at the C(8)' position with at least the substituent —C≡C—R', where R' is H, $Si(CH_3)_3$, t-butyl, isopropyl, methyl, or cyclopropyl; $R_1$ and $R_1'$ are independently one of H, $CH_3$, $CF_3$, $CH_2CH_3$, $CH_2CF_3$, or cyclopropyl; $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position; and B is O, NH, or —$N(R_7)$—$N(R_7)$—, where $R_7$ is one of H, $CH_3$, alkyl, or cycloalkyl. Preferred compounds according to formula XI include:

Yet another aspect of the present invention provides a compound of formula XII, or a salt or prodrug thereof,

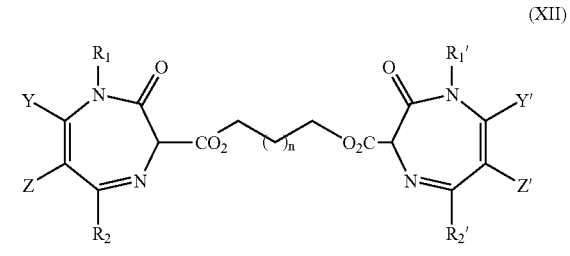

(XII)

wherein n is 0 to 4; Y and Z are taken together with the two intervening carbon atoms to form a ring selected from phenyl and thienyl, which ring is substituted at the C(7) position with at least the substituent —C≡C—R, where R is H, $Si(CH_3)_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, $Si(CH_3)_3$, t-butyl, isopropyl, methyl, or cyclopropyl; $R_1$ and $R_1'$ are independently one of H, $CH_3$, $CF_3$, $CH_2CF_3$, $CH_2CH_3$, or cyclopropyl; and $R_2$ and $R_2'$ are independently a substituted or unsubstituted at least partially unsaturated 5 or 6 membered cyclic or heterocyclic ring, wherein if substituted the substituent is one or more of F, Cl, Br, or $NO_2$ at the 2'-position. Preferred compounds according to formula XII include:

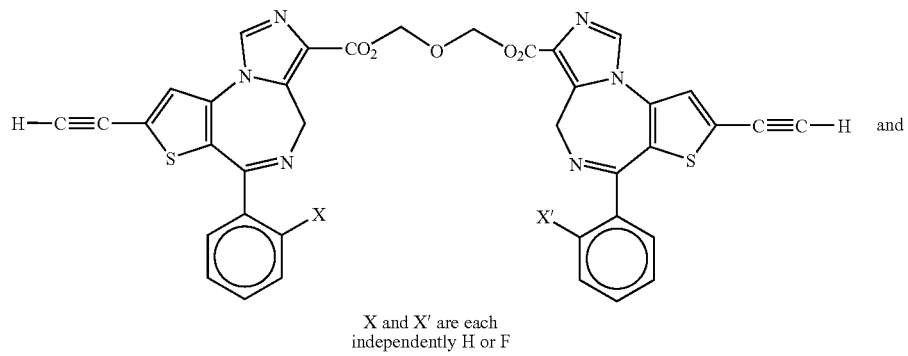

and

X and X' are each independently H or F

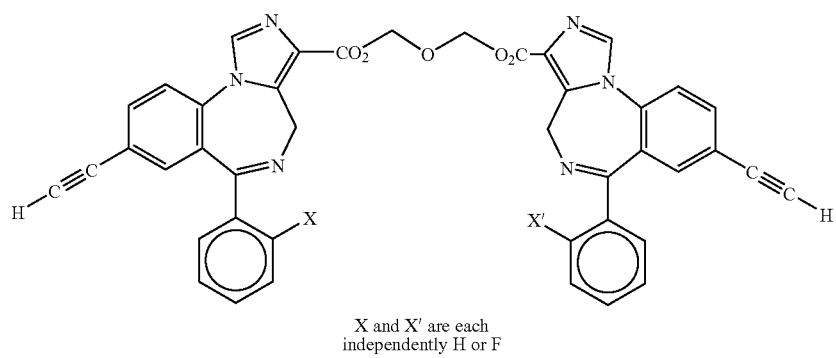

X and X' are each independently H or F

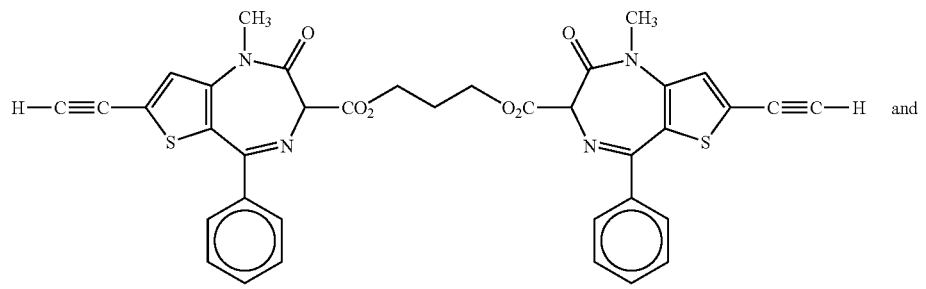

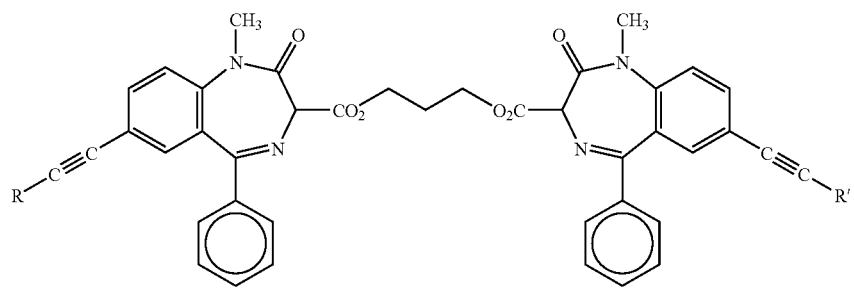

R is H or Si(CH$_3$)$_3$
R' is H or Si(CH$_3$)$_3$

A still further aspect of the present invention provides a compound of the formula XIII, or a salt or prodrug thereof,

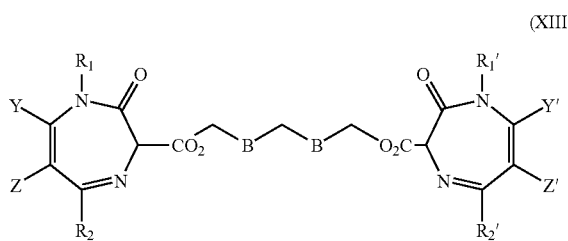

(XIII)

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O or NH and wherein —BCH$_2$B— is optionally replaced with —N(R$_7$)—N(R$_7$)—, where R$_7$ is one of H, CH$_3$, alkyl, or cycloalkyl. Preferred compounds according to formula XIII include:

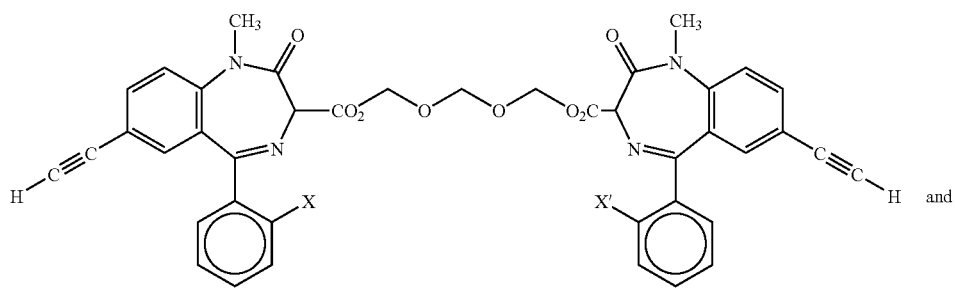

X and X' are each independently H or F

-continued

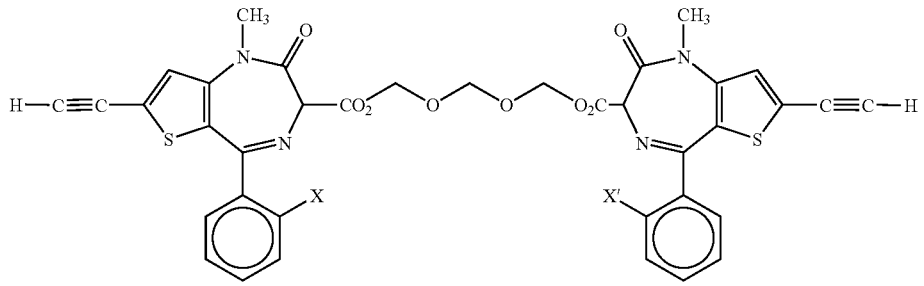

X and X' are each independently H or F

Yet another aspect of the present invention provides a compound of the formula XIV, or a salt or prodrug thereof, (XIV)

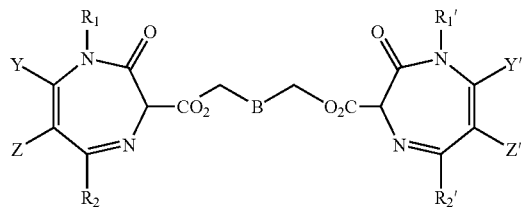

wherein Y and Z are taken together with the two intervening carbon atoms to form a ring selected from phenyl and thienyl, which ring is substituted at the C(7) position with at least the substituent —C≡C—R, where R is H, Si(CH$_3$)$_3$, t-butyl, isopropyl, methyl, or cyclopropyl; Y' and Z' are taken together with the two intervening carbon atoms to form a ring selected from phenyl and thienyl, which ring is substituted at the C(7)' position with at least the substituent —C≡C—R', where R' is H, Si(CH$_3$)$_3$, t-butyl, isopropyl, methyl, or cyclopropyl; R$_1$ and R$_1$' are independently one of H, CH$_3$, CF$_3$, CH$_2$CH$_3$, CH$_2$CF$_3$, or cyclopropyl; R$_2$ and R$_2$' are independently a substituted or unsubstituted at least partially unsaturated 5 or 6 membered cyclic or heterocyclic ring, wherein if substituted the substituent is one or more of F, Cl, Br, or NO$_2$ at the 2'-position; and B is O, NH, or —N(R$_7$)—N(R$_7$)—, where R$_7$ is one of H, CH$_3$, alkyl, or cycloalkyl. Preferred compounds according to formula XIV include:

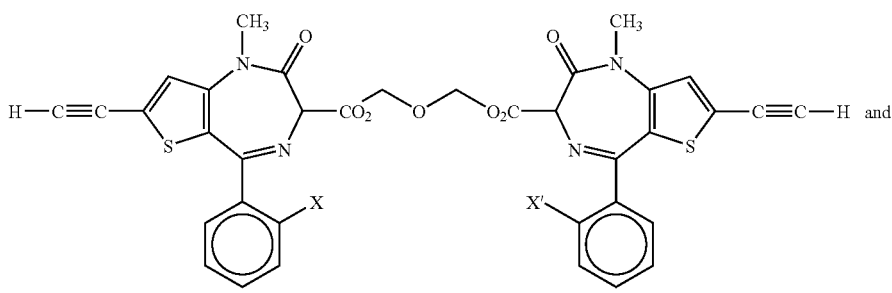

X and X' are each independently H or F

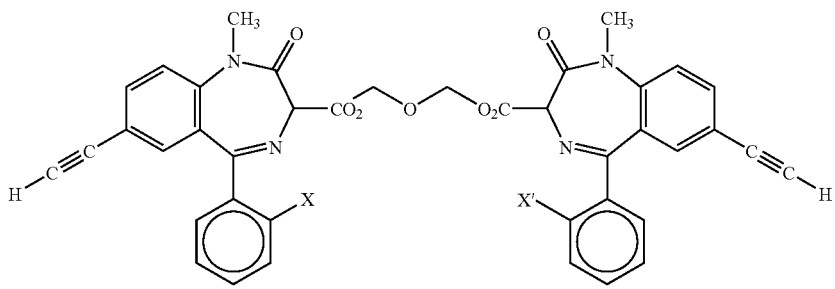

X and X' are each independently H or F

Another compound (XV) of the present invention is

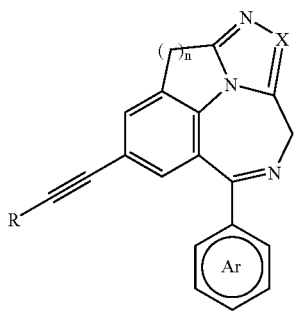

n=1, n=2; R=H, SiMe₃, tBu, CH₃,

Ar=phenyl, 2'-flurophenyl, 2-thienyl, 3-thienyl, 2-pyridyl, 2-pyridyl N—O; X=N or CH Yet another compound (XVI) of the present invention is:

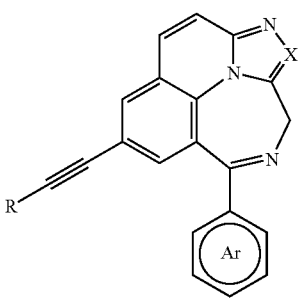

R=H, SiMe₃, tBu, CH₃,

;

Ar=phenyl, 2'-flurophenyl, 2-thienyl, 3-thienyl, 2-pyridyl, 2-pyridyl N—O; X=N or CH Still another compound (XVII) of the present invention is:

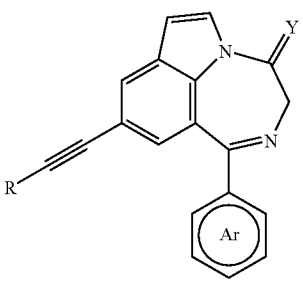

R=H, SiMe₃, tBu, CH₃,

;

Ar=phenyl, 2'-flurophenyl, 2-thienyl, 3-thienyl, 2-pyridyl, 2-pyridyl N—O; Y=O, S, NHCH₃

Another compound (XVIII) of the present invention is:

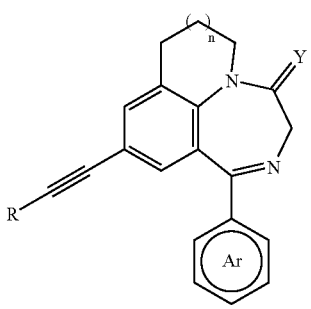

n=0, n=1; R=H, SiMe₃, tBu, CH₃,

;

Ar=phenyl, 2'-flurophenyl, 2-thienyl, 3-thienyl, 2-pyridyl, 2-pyridyl N—O; Y=O, S, NHCH₃

Yet another compound (XIX) of the present invention is:

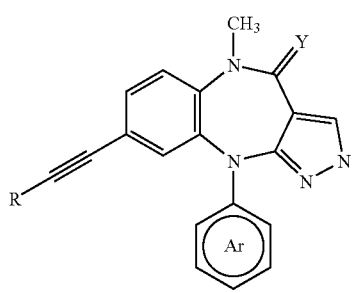

R=H, SiMe₃, tBu, CH₃,

;

Ar=phenyl, 2'-flurophenyl, 2-thienyl, 3-thienyl, 2-pyridyl, 2-pyridyl N—O; Y=O, S, NHCH₃

Still another compound (XX) of the present invention is:

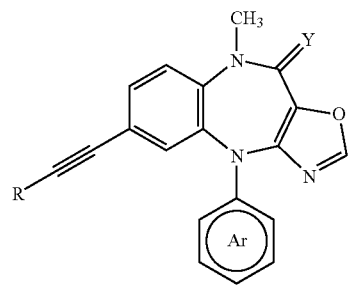

R=H, SiMe₃, tBu, CH₃,

;

Ar=phenyl, 2'-flurophenyl, 2-thienyl, 3-thienyl, 2-pyridyl, 2-pyridyl N—O; Y=O, S, NHCH₃

A further compound (XXI) of the present invention is:

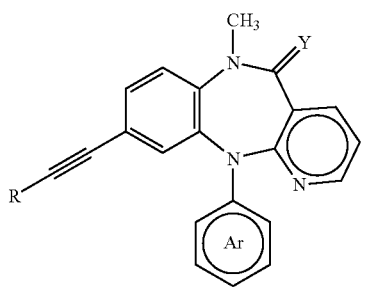

R=H, SiMe$_3$, tBu, CH$_3$,

;

Ar=phenyl, 2'-flurophenyl, 2-thienyl, 3-thienyl, 2-pyridyl, 2-pyridyl N—O; Y=O, S, NHCH$_3$ Compounds (XV) to (XXI) above can also have R as CF$_3$, CCl$_3$, or CBr$_3$.

A still further aspect of the present invention provides compositions comprising compounds of the above kind in a pharmaceutically acceptable carrier. Such pharmaceutically acceptable carriers are well known in the art.

Another aspect of the invention provides a method for the treatment and/or prevention of anxiety which comprises administering to a patient in need of such treatment an effective amount of a compound of the above kinds, or a pharmaceutically acceptable salt thereof or a prodrug thereof.

In the above embodiments by "alkyl" we mean a straight or branched halogenated or unhalogenated alkyl group having 1-6 carbon atoms. By "cycloalkyl" we mean one containing 3-7 carbon atoms. Also, in the above embodiments by "cyclic" we prefer a phenyl group and by "heterocyclic" we prefer a 2-pyridine or a 2- or 3-thiophene.

The compounds of the present invention are GABA$_A$ receptor ligands which exhibit anxiolytic activity due to increased agonist efficacy at GABA$_A$/α2, GABA$_A$/α3 and/or GABA$_A$/α5 receptors. The compounds in accordance with this invention may possess at least 2-fold, suitably at least 5-fold, and advantageously at least a 10-fold, selective efficacy for the GABA$_A$/α2, GABA$_A$/α3, and/or GABA$_A$/α5 receptors relative to the GABA$_A$/α1 receptors. However, compounds which are not selective in terms of their agonist efficacy for the GABA$_A$/α2, GABA$_A$/α3, and/or GABA$_A$/α5 receptors are also encompassed within the scope of the present invention. Such compounds will desirably exhibit functional selectivity by demonstrating anxiolytic activity with decreased sedative-hypnotic/muscle relaxant/ataxic activity due to decreased efficacy at GABA$_A$/α1 receptors.

For use in medicine, the salts of the compounds of formulas (I)-(XXI) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The present invention includes within its scope prodrugs of the compounds of formulas (I)-(XXI) above. In general, such prodrugs will be functional derivatives of the compounds of formulas (I)-(XXI) which are readily convertible in vivo into the required compound of formulas (I)-(XXI). Conventional procedures for the selection and preparation of suitable prodrug derivatives are described, for example, in *Design of Prodrugs*, ed. H. Bundgaard, Elsevier, 1985.

Where the compounds according to the invention have at least one asymmetric center, they may accordingly exist as enantiomers. Where the compounds according the invention possess two or more asymmetric centers, they may additionally exist as diastereoisomers. It is to be understood that all such isomers and mixtures thereof in any proportion are encompassed within the scope of the present invention.

The compounds according to the present invention exhibit anxiolytic activity, as may be demonstrated in rats by a positive response in a preclinical test for anti-anxiety efficacy (e.g., situational anxiety or defensive withdrawal). Moreover, the compounds of the invention are substantially non-sedating and non-ataxic as may be confirmed by an appropriate result obtained from the locomotor activity test and rotorod paradigm, respectively.

The compounds according to the present invention may also exhibit anticonvulsant activity. This can be demonstrated by the ability to block pentylenetetrazole-induced seizures in rodents.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid performulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day, or on a continuous basis via, for example, the use of a transdermal patch.

DETAILED DESCRIPTION OF THE INVENTION

Scheme 1 (QHII-066)

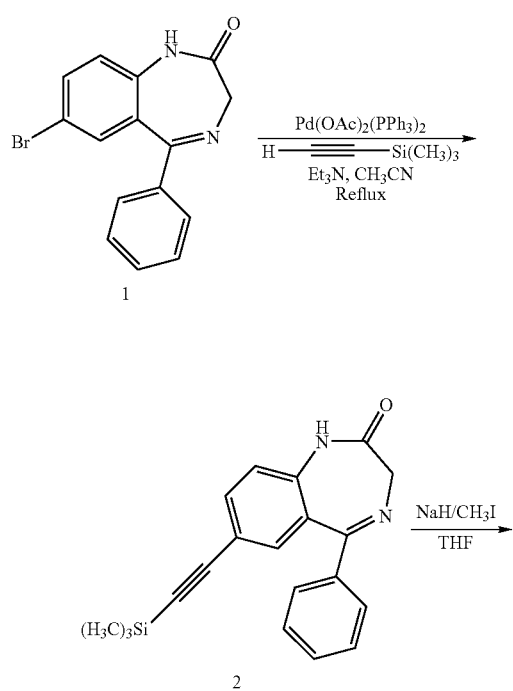

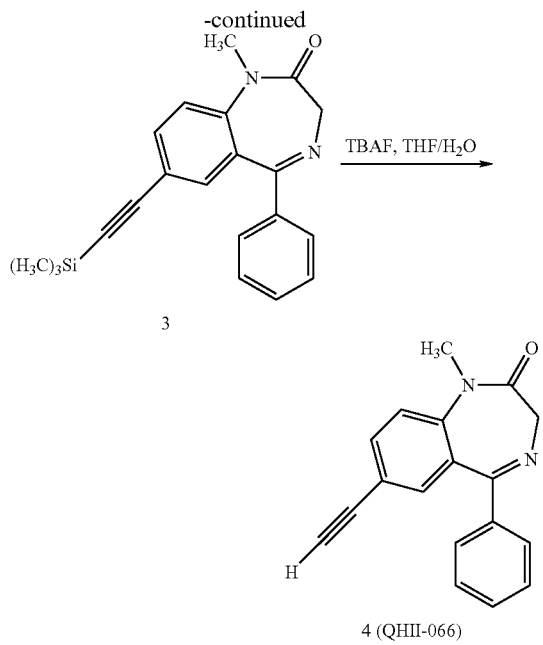

The bromide 1 available from reference [1] was reacted with trimethylsilyacetylene in the presence of a palladium catalyst to provide trimethylsilyl analog 2.[4,5,6] This product was methylated with methyl iodide/sodium hydride to give the N-methyl benzodiazepine 3. This was subjected to fluoride-mediated desilation to furnish 4 (QHII-066).

Procedure for QHII-066

7-Trimethylsilylacetyleno-5-phenyl-1,3-dihydrobenzo[e]-1,4-diazepin-2-one 2.[4,5,8]

A mixture of 1[1] (1 g, 3.17 mmole available from reference 1) in triethyl amine (30 mL) and CH$_3$CN (20 mL) with trimethylsilylacetylene (622.7 mg, 6.34 mmole) and bis(triphenylphosphine)-palladium (II) acetate (118 mg, 0.16 mmol) was heated to reflux under nitrogen. After 12 hours, the reaction mixture was cooled to room temperature and filtered. The filtrate was concentrated in vacuum and the residue was treated with a saturated aqueous solution of NaHCO$_3$ (30 mL), and extracted with CH$_2$Cl$_2$ (3×50 mL). The organic layers were combined and washed with brine and dried (Na$_2$SO$_4$). After removal of solvent under reduced pressure, the residue was purified via flash chromatography (silica gel, EtOAc/hexanes:1/1) to furnish 3 as a yellow powder (791 mg, 75%): mp: 190-191.5° C.; IR (KBr) 3011, 2281, 1686, 1610, 1486, 1325, 1249, 839, 700 cm$^{-1}$; 1H NMR (CDCl$_3$) δ 0.21 (s, 9H), 4.31 (s, 2H), 7.09 (d, 1H, J=8.25 Hz), 7.21-7.61 (br, 7H), 10.17 (s, 1H); MS (CI) m/e (relative intensity) 333 (M$^+$+1, 100). This material was used in the next step.

1-Methyl-7-trimethylsilylacetyleno-5-phenyl-1,3-dihydrobenzo[e]-1,4-diazepin-2-one 3.[7]

A mixture of 2 (485 mg, 1.46 mmol) was dissolved in dry THF (20 mL) at 0° C. and NaH (60% in mineral oil, 70 mg, 1.75 mmol) was added to the solution in one portion. The slurry was then stirred for 20 min at 0° C. and CH$_3$I (311 mg, 2.19 mmol) was added to the mixture and it was warmed up to room temperature. After the mixture stirred for 3 hours at room temperature, the THF was then removed under reduced pressure. The residue was purified by flash chromatography [hexanes/EtOAc (1:4)] to provide the title compound 3 (303 mg, 60%) as a white solid: mp: 177–178° C.; IR (KBr) 2954, 2147, 1687, 1612, 1491, 1382, 1115, 1075, 839, 700 cm$^{-1}$; 1HNMR (CDCl$_3$) δ(ppm), 3.18 (s, 3H), 3.54 (d, 1H, J=10.8 Hz), 4.60 (d, 1H, J=10.8 Hz), 7.05 (s, 1H), 7.07 (d, 1H, J=8.58 Hz), 7.20–7.27 (m, 3H), 7.37–7.42 (m, 3H); MS (EI) m/e 346 (M$^+$, 90), 318 (100), 303(19), 165(22), 151(20). Anal. Calcd. for $C_{21}H_{22}N_2OSi$: C, 72.79; H, 6.40; N, 8.08. Found: C, 72.50; H, 6.68; N, 8.04.

1-Methyl-7-acetyleno-5-phenyl-1,3-dihydro-benzo[e]-1,4-diazepin-2-one 4 (QHII-066).[7]

A solution of 3 (100 mg,) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried (Na$_2$SO$_4$). The solvent was removed under vacuum and the residue which resulted was passed through a wash column (silica gel, EtOAc/hexanes:4/1) to give 4 (QHII-066) as light yellow crystals (71 mg, 90%): mp: 163–165° C.; IR (KBr) 2965, 1680, 1605, 1387, 1121, 833, 747 cm$^{-1}$; $^1$HNMR (CDCl$_3$) δ (ppm) 3.38 (s, 3H), 3.75 (d, 1H, J=10.8 Hz), 4.80 (d, 1H, J=10.9 Hz), 5.28 (s, 1H), 7.29 (d, 1H, J=8.5 Hz), 7.35–7.45 (m, 4H), 7.55–7.59 (m, 2H), 7.62 (dd, 1H, J=8.5 Hz, 2.0 Hz); MS (EI) m/e (relative intensity) 274 (M$^+$, 100), 259 (12), 246 (100), 189 (12).122(19), 105 (42). Anal. Calcd. for $C_{18}H_{14}N_2O \cdot \frac{2}{3}H_2O$, Calculated: C, 75.51; H, 4.89; N, 9.78. Found: C, 75.59; H, 5.17; N, 9.62.

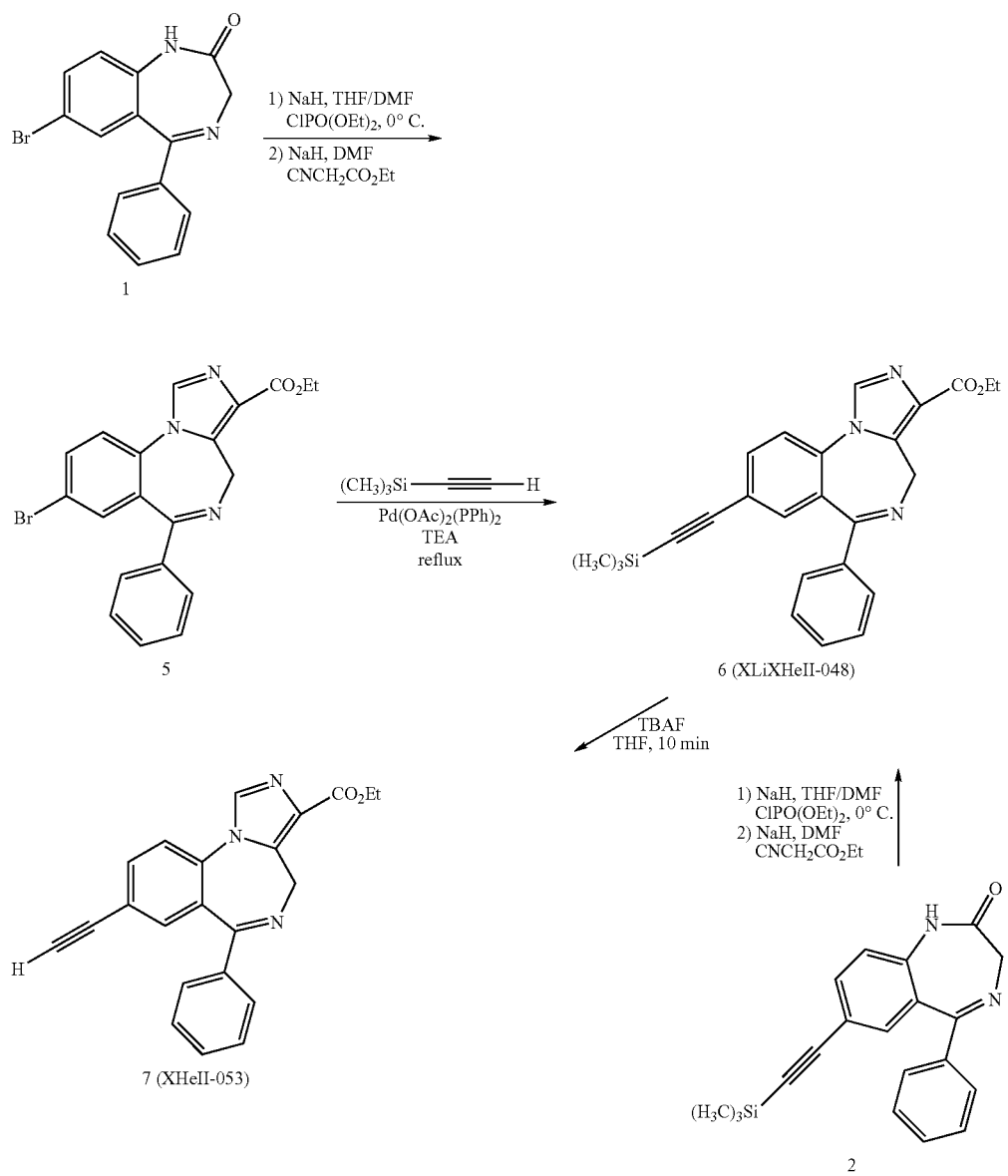

The bromide 1 was reacted with diethylphosphorochloridate in the presence of sodium hydride, followed by addition of ethyl isocyanoacetate to provide the ester 5. This was converted to the trimethylsilylacetyleno compound 6 (XLiXHeII-048) under standard conditions (Pd-mediated, Heck-type coupling).[8] Treatment of 6 with fluoride gave the title compound 7 (XHeII-053).

Procedure for XHe-II-053

Ethyl 8-bromo-6-phenyl-4H-benzo[f]imidazo[1,5-a][1,4]diazepine-3-carboxylate 5.

This benzodiazepine 5 was obtained in 45% yield from 1[1] analogous to the literature procedure[2] as a white solid. 2: mp: 174-175° C.; IR (KBr) 2978, 1712, 1609, 1491 cm$^{-1}$; $^1$H NMR (CDCl$_3$) δ 1.44 (t, 3H, J=7.1 Hz), 4.09 (d, 1H, J=12.1 Hz), 4.38-4.49 (m, 2H), 6.08 (d, 1H, J=12.3 Hz), 7.40-7.53 (m, 6H), 7.60 (d, 1H, J=2.2 Hz), 7.82 (dd, 1H, J=8.6 Hz and 2.2 Hz), 7.95 (s, 1H); MS (EI) m/e (relative intensity) 411 (34), 410 (M$^+$, 8), 409 (34), 365 (61), 363 (61), 337 (100), 335 (100), 285 (21), 232, (17). Anal. Calcd. for C$_{20}$H$_{16}$BrN$_3$O$_2$: C, 58.55; H, 3.93; N, 10.24. Found: C, 58.30, H, 3.91; N, 9.90.

Ethyl 8-trimethylsilylacetylenyl-6-phenyl-4H-benzo[f]imidazo[1,5-a][1,4]diazepine-3-carboxylate 6 (XLiXHeII-048).[4,5,8]

A mixture of bromide 5 (0.3 g, 0.73 mmol), trimethylsilylacetylene (0.143 g, 1.46 mmol) and bis(triphenylphosphine)-palladium-(I) acetate (55 mg, 0.073 mmol) in a mixed solvent system of toluene (20 mL) and anhydrous TEA (50 mL) was heated to reflux under argon. After stirring for 12 hours at reflux, the mixture was cooled to room temperature and the precipitate which formed was removed by filtration. The filtrate was concentrated under reduced pressure and the residue was treated with a saturated aqueous solution of NaHCO$_3$ (20 mL), and extracted with CHCl$_3$ (3×25 mL). The combined extracts were washed with brine and dried (Na$_2$SO$_4$). After removal of solvent under reduced pressure, the residue was purified by flash chromatography (silica gel, EtOAc) to afford 6 (XLiXHeII-048) as a white solid (0.29 g, 93%). This benzodiazepine can also be obtained from 2 in 45% yield by following the same procedure 6 (XLiXHeII-048): mp: 170-172° C.; IR (KBr) 2958, 2152, 1718 cm$^{-1}$; $^1$H NMR (CDCl$_3$) δ 0.23 (s, 9H), 1.42 (t, 3H, J=7.2 Hz), 4.04 (d, 1H, J=12.6 Hz), 4.41 (m, 2H, J=7.2 Hz), 6.23 (d, 1H, J=12.6 Hz), 7.35-7.55 (m, 7H), 7.73 (dd, 1H, J=8.3 Hz, J=1.9 Hz), 7.93 (s, 1H); MS (EI) m/e (relative intensity) 427 (M$^+$, 76), 412 (5), 381 (55), 353 (100) 303 (10), 287 (7). Anal. Calcd. for C$_{25}$H$_{25}$N$_3$O$_2$Si.⅓ EtOAc: C, 69.22; H, 6.01; N, 9.20. Found: C, 68.87; H, 5.81; N, 9.37.

Ethyl 8-acetylenyl-6-phenyl-4H-benzo[f]imidazo[1,5-a][1,4]diazepine-3-carboxylate 7 (XHeII-053).[7]

A solution of 6 (XLiXHeII-048) (0.17 g, 0.41 mmol), in THF (15 mL) was treated with Bu$_4$NF.H$_2$O (0.16 g, 0.62 mmol). The mixture which resulted was allowed to stir for 30 min at room temperature after which the mixture was added to H$_2$O (10 mL) and extracted with EtOAc (3×25 mL). The combined organic extracts were washed with brine (25 mL) and dried (Na$_2$SO$_4$). After removal of solvent under reduced pressure, the residue was purified by a wash column (silica gel, EtOAc) to furnish 7 (XHeII-053) (0.12 g, 85%) as a white solid: mp 237-239° C.; IR (KBr) 3159, 3107, 2092, 1721, 1606 cm$^{-1}$; $^1$H NMR (CDCl$_3$) δ 1.44 (t, 3H, J=7.1 Hz), 3.20 (s, 1H), 4.13 (d, 1H, J=10.22 Hz), 4.41-4.48 (m, 2H), 6.11 (d, 1H, J=12 Hz), 7.42-7.63 (m, 7H), 7.81 (dd, 1H, J=8.3 Hz and 1.8 Hz), 8.03 (s, 1H); MS (EI) m/e (relative intensity) 355 (M$^+$, 83), 309 (70), 281 (100), 253 (12), 231 (18), 178 (20). Anal. Calcd. for C$_{22}$H$_{17}$N$_3$O$_2$.¾H$_2$O: C, 71.63; H, 5.05; N, 11.39. Found: C, 71.27; H, 4.71; N, 11.03.

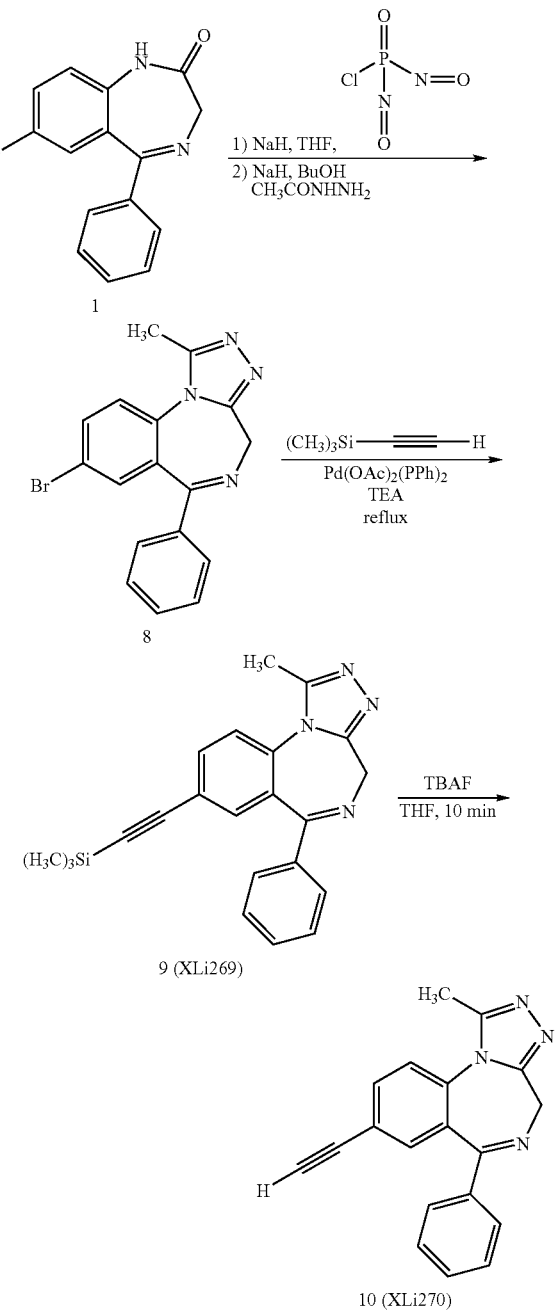

Scheme 3 (XLi270)

The bromide 1, available from reference 1, was stirred with the di-4-morpholino-phosphinic chloride, followed by addition of acetylhydrazide to furnish triazolo-benzodiazepine 8. This material 8 was subjected to a Heck-type coupling reaction (TMS-C≡CH, Pd-mediated)[4,7,8] to furnish ligand 9. This analog was converted into 10 (XLi270) on stirring with fluoride anion as shown in Scheme 3.

Procedure for XLi 270

8-Bromo-1-methyl-6-phenyl-4H-s-triazolo[4,3-a][1,4]benzodiazepine 8.[3]

A solution of 1[1] (1 g, 3.07 mmol of 7-bromo-5-phenyl-1,4-benzodiazepine-2-one) in dry THF (20 mL) was cooled in an ice-water bath and a 60% dispersion of sodium hydride (152.2 mg) was added in one portion. After 20 minutes, di-4-morpholinylphosphinic chloride[3] (943.9 mg, 4.76 mmol) was added at 0° C. and this was stirred for 30 minutes and allowed to warm to room temperature. The mixture was stirred for 1.5 hours. To this mixture was then added a solution of acetylhydrazide (521.9 mg, 7.14 mmol) in dry butanol (5 mL) and stirring was continued at room temperature for 10 min. The solvents were evaporated and the residue was dissolved in butanol (10 mL) and heated to reflux for 5 hours. Butanol was removed under reduced pressure and the residue was partitioned between $CH_2Cl_2$ (50 mL) and water (50 mL). The water layer was extracted by $CH_2Cl_2$ (3×30 mL). The combined organic layer was washed by brine (30 mL). The organic layer was dried ($Na_2SO_4$) and the solvent was removed under vacuum. The residue was purified by flash chromatography (silica gel) to provide pure 8 [539.5 mg (40% yield)] as a white solid: mp 268.5-270° C.; IR (KBr) 2358, 1607, 1538, 1484, 1311, 1000, 801, 697 $cm^{-1}$; $^1$H NMR ($CDCl_3$) δ 2.82(s, 3H), 4.11(d, 1H, J=12.8 Hz), 5.49 (d, 1H, J=12.8 Hz), 7.21-7.68 (m, 7H), 7.75 (dd, 1H, J=0.58 Hz, J=1.5 Hz); MS (EI) m/e (relative intensity) 354 (34), ($M^+$, 16), 352 (34), 325(33), 323 (34), 273 (63), 245 (31), 232 (19), 204 (100), 183(23), 177 (36), 151 (24). Anal. Calcd. for $C_{17}H_{13}BrN_4$: C, 57.81; H, 3.71; N, 15.86. Found C, 57.57; H, 3.64: N, 15.70.

8-Trimethylsilylacetylenyl-1-methyl-6-phenyl-4H-s-triazolo[4,3-a][1,4]-benzodiazepine 9.[4,5,8] (XLi269).

A mixture of 8 (8-bromo-1-methyl-6-phenyl-4-H-s-triazolo-[4,3-a][1,4]benzodiazepine, 300 mg, 0.85 mmol), trimethylsilylacetylene (208.5 mg, 2.12 mmol) and bis(triphenylphosphine)-palladium(II) acetate in a mixed solvent system of $EtN_3$ (5 mL) and $CH_3CN$ (8 mL) was heated to reflux under nitrogen. After stirring for 6 hours at reflux. The mixture was cooled to room temperature. The mixture was concentrated under reduced pressure and $H_2O$ (30 mL) was added. The mixture was extracted with $CH_2Cl_2$ (3×50 mL). The combined extracts were washed with brine and dried ($Na_2SO_4$). After removal of solvent under reduced pressure, the residue was purified by flash chromatography (silica gel, EtOH/EtOAc) to afford benzodiazepine 9 (185 mg, 60% yield) as a white solid: mp 229-233° C.; IR (KBr) 2957, 2156, 1609, 1537, 1491, 1424, 1315, 1249, 881, 844, 750 $cm^{-1}$; $^1$H NMR ($CDCl_3$) δ 0.23 (s, 9H), 2.68 (s, 3H), 4.11 (d, 1H, J=12.5 Hz), 5.49 (d, 1H, J=13.0 Hz), 7.21-7.68(m, 7H), 7.75(dd, 1H, J=8.5 Hz, J=1.5 Hz); MS (EI) m/e (relative intensity) 370 ($M^+$, 80), 355 (44), 341 (60), 286 (34), 177 (51), 163 (52) 143 (100), 129 (19), 115 (28). Anal. Calcd. for $C_{22}H_{22}N_4Si$: C, 71.31; H, 5.98; N, 15.12. Found: C, 70.90; H, 5.93; N, 15.08.

8-Acetylenyl-1-methyl-6-phenyl-4H-s-triazolo[4,3-a][1,4]benzodiazepine 10 (Xli-270).[7]

A solution of 9 [trimethylsilylacetylenyl-1-methyl-6-phenyl-4H-s-triazolo-[4,3-a]-[1,4]-benzodiazepine (106.4 mg, 0.288 mmol)] in dry THF (20 mL) was treated with $Bu_4NF$ (1.0 M in THF, 112.8 mg, 0.431 mmol). The mixture which resulted was allowed to stir for 5 min at room temperature after which the mixture was added to $H_2O$ (10 mL) and extracted with $CH_2Cl_2$ (3×25 mL). The combined organic extracts were washed with brine (25 mL) and dried ($Na_2SO_4$). After removal of solvent under reduced pressure, the residue was crystallized from EtOAc to provide benzodiazepine 10 (XLi270) (66.8 mg, 80% yield) as a white solid: mp>250° C. (dec); IR (KBr) 3198, 2158, 1609, 1538, 1491, 1425, 1317, 1002, 838, 748, 695 $cm^{-1}$; $^1$H NMR ($CDCl_3$) δ 2.78 (s, 3H), 3.15 (s, 1H), 4.11 (d, 2H, J=12.8 Hz), 5.91 (d, 1H, J=12.8 Hz), 7.35-7.85 (m, 8H); MS (EI) (relative intensity) 298 ($M^+$, 100), 269 (78), 230 (48), 228 (65), 201 (20), 127 (65), 115 (42), 101 (54). Anal. Calcd. for $C_{19}H_{14}N_4 \cdot \frac{1}{2}CH_3OH$: C, 74.50; H, 5.13; N, 17.82. Found: C, 74.33; H, 4.83; N, 17.77,

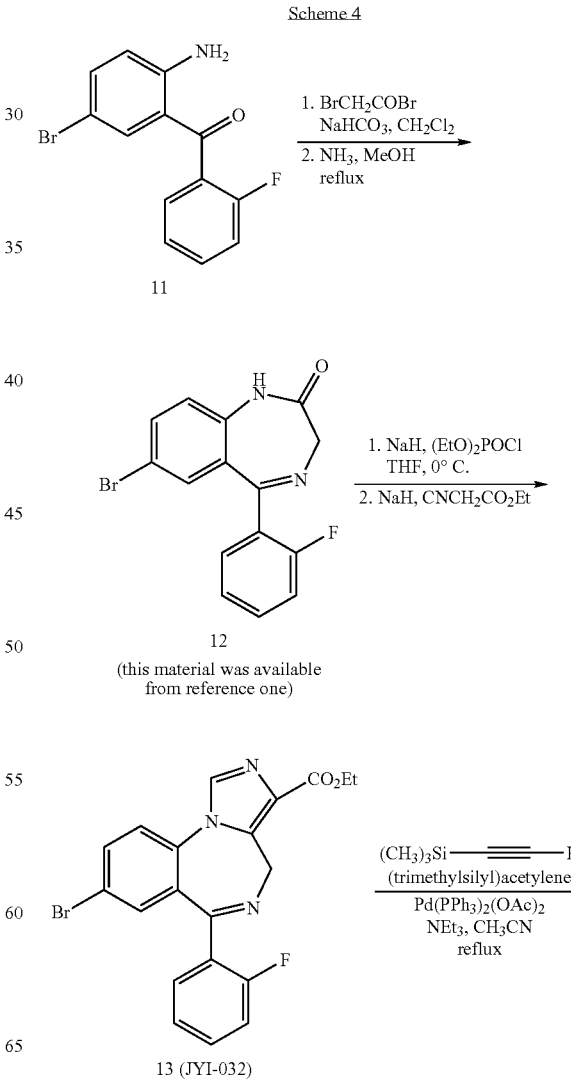

Scheme 4

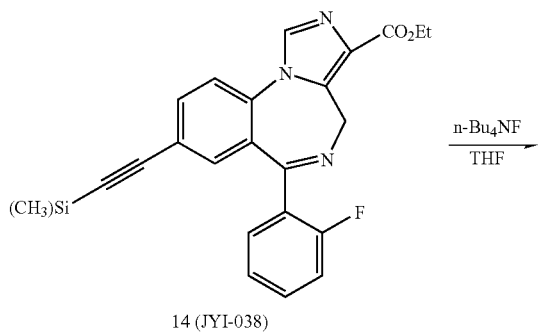

14 (JYI-038)

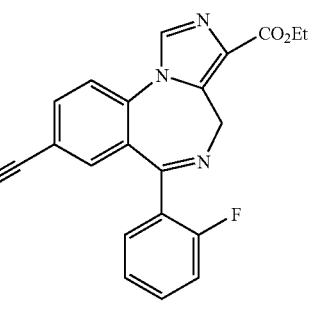

15 (JY-XHE-053)

The 7-bromo-2'-fluorobenzodiazepine 12 (available from reference 1) was reacted with sodium hydride and diethylphosphorochloridate and this was followed by addition of ethyl isocyanoacetate to provide benzimidazo intermediate 13 (JYI-032),[2] as illustrated in Scheme 4. This material was heated with trimethysilylacetylene in a Heck-type coupling reaction[8] to provide the trimethylsilyl analog 14 (JYI-038). The silyl group was removed from 14 on treatment with fluoride anion to furnish 15, a 2'-fluoro analog of XHeII-053, in excellent yield.

Procedure:

Ethyl 8-bromo-6-(2'-fluorophenyl)-4H-benzo[f]imidazo[1,5-a][1,4]diazepine-3-carboxylate 13 (JYI-032).

A solution of 121 (7.0 g, 21.0 mmol) in THF (50 mL) was cooled in ice-water, and sodium hydride (1.0 g, 25.2 mmol) was added in one portion. After 30 min, diethyl phosphorochloridate (5.62 g, 31.5 mmol) was added dropwise, and the solution which resulted was stirred continuously for 30 min with cooling from an ice bath. A solution of ethyl isocyanoacetate (4.22 g, 25.2 mmol) and sodium hydride (1.17 g, 29.4 mmol) in THF (10 mL), which had stirred for 30 min with ice-bath cooling, was added slowly via a cannula. After stirring for another 30 min with cooling, the reaction mixture was allowed to stir at room temperature overnight. The mixture was then added to $H_2O$ (10 mL) and extracted with EtOAc (3×50 mL). The combined organic extracts were washed with brine (2×50 mL) and dried ($Na_2SO_4$). The solvent was evaporated under reduced pressure and the residue was purified by flash chromatography (silica gel, hexanes/EtOAc:2/1) to afford 13 (JYI-032, 5.2 g, 58%) as a white solid: mp 200-201.5° C.; IR (KBr) 2977, 1718, 1610, 1491, 1450 cm$^{-1}$; $^1$H NMR (DMSO-d$_6$) δ 1.30 (t, 3H, J=4.2 Hz), 4.28 (bs, 1H), 4.30 (q, 2H, J=4.2 Hz), 5.75 (bs, 1H), 7.20 (t, 1H, J=5.6 Hz), 7.30 (t, 1H, J=4.5 Hz), 7.40 (s, 1H), 7.54 (m, 2H), 7.85 (d, 1H, J=5.2 Hz), 7.96 (dd, 1H, J=5.2 Hz and 1.3 Hz), 8.44 (s, 1H); MS (EI) m/e (relative intensity) 428 (7), 381 (58), 355 (100), 303 (37), 274 (36), 247 (35), 234 (52), 154 (71), 127 (62). Anal Calcd. for $C_{20}H_{15}N_3O_2FBr$: C, 56.09; H, 3.53; N, 9.81. Found: C, 56.02; H, 3.51; N, 9.58.

Ethyl 8-trimethylsilylacetylenyl-6-(2'-fluorophenyl)-4H-benzo[f]-imidazo[1,5-α][1,4]diazepine-3-carboxylate 14 (JYI-038).

A mixture of bromide 13 (JYI-032, 1.40 g, 3.3 mmol), trimethylsilylacetylene (0.65 g, 6.6 mmol) and bis(triphenylphosphine)-palladium (II) acetate (0.25 g, 0.33 mmol) in a mixed solvent system of $CH_3CN$ (80 mL) and anhydrous triethylamine (50 mL) was heated to reflux under argon. After stirring for 2 h at reflux, the mixture was cooled to room temperature and the precipitate which formed was removed by filtration. The filtrate was concentrated under reduced pressure and the residue was treated with a saturated aqueous solution of $NaHCO_3$ (40 mL), and extracted with $CHCl_3$ (3×50 mL). The combined organic extracts were washed with brine (2×20 mL) and dried ($Na_2SO_4$). After removal of solvent under reduced pressure, the residue was purified by flash chromatography (silica gel, hexanes/EtOAc:3/1) to afford 14 (JYI-038, 1.2 g, 82%) as a white solid: mp 196-197.5° C.; IR (KBr) 2959, 2157, 1709, 1613, 1494, 1451, 1252 cm$^{-1}$; $^1$H NMR (DMSO-d$_6$) δ 0.20 (s, 9H), 1.32 (t, 3H, J=7.1 Hz), 4.18 (bs, 1H), 4.32 (q, 2H, J=7.1 Hz), 5.78 (bs, 1H), 7.25 (t, 1H, J=11.5 Hz), 7.30-7.35 (m, 4H), 7.81 (d, 1H, J=6.6 Hz), 7.93 (d, 1H, J=8.4 Hz), 8.49 (s, 1H); MS (EI) m/e (relative intensity) 445 (37), 399 (51), 371 (100), 235 (71), 192 (66), 178 (75). Anal. Calcd. for $C_{25}H_{24}N_3O_2FSi$: C, 67.39; H, 5.42; N, 9.43. Found: C, 66.98; H, 5.46; N, 9.19.

8-Acetyleno-6-(2'-fluorophenyl)-4H-benzo[f]imidazo[1,5-a][1,4]diazepine-3-carboxylate 15 (JY-XHE-053).

A solution of 14 (JYI-038, 80 mg, 0.18 mmol) in THF (5 mL) was treated with Bu$_4$NF (0.5 mL, 1.0M solution in THF). The mixture which resulted was allowed to stir for 5 min at room temperature after which the mixture was added to $H_2O$ (5 mL) and extracted with EtOAc (3×10 mL). The combined organic extracts were washed with brine (2×10 mL) and dried ($Na_2SO_4$). The solvent was removed under reduced pressure and the residue was purified by flash chromatography (silica gel, EtOAc) to afford 15 (JY-XHE-053, 67 mg, 80%) as a white solid: mp 223.5-224.5° C.; IR (KBr) 3288, 2979, 1712, 1621, 1491, 1255, 1190 cm$^{-1}$; $^1$H NMR (DMSO-d$_6$) δ 1.34 (t, 3H, J=7.1 Hz), 4.27 (bs, 1H), 4.36 (q, 2H, J=7.1 Hz), 4.47 (s, 1H), 5.80 (bs, 1H), 7.22 (t, 1H, J=8.4 Hz), 7.30-7.60 (m, 4H), 7.85 (d, 1H, J=6.6 Hz), 7.92 (d, 1H, J=8.4 Hz), 8.83 (s, 1H); MS (EI) m/e (relative intensity) 373 (28), 327 (47), 299 (100), 249(22), 178 (50).

Anal. Calcd. for $C_{22}H_{16}N_3O_2F\cdot\frac{1}{2}H_2O$: C, 69.10; H, 4.48; N, 10.99. Found: C, 69.19; H, 4.39; N, 10.68.

Scheme 5

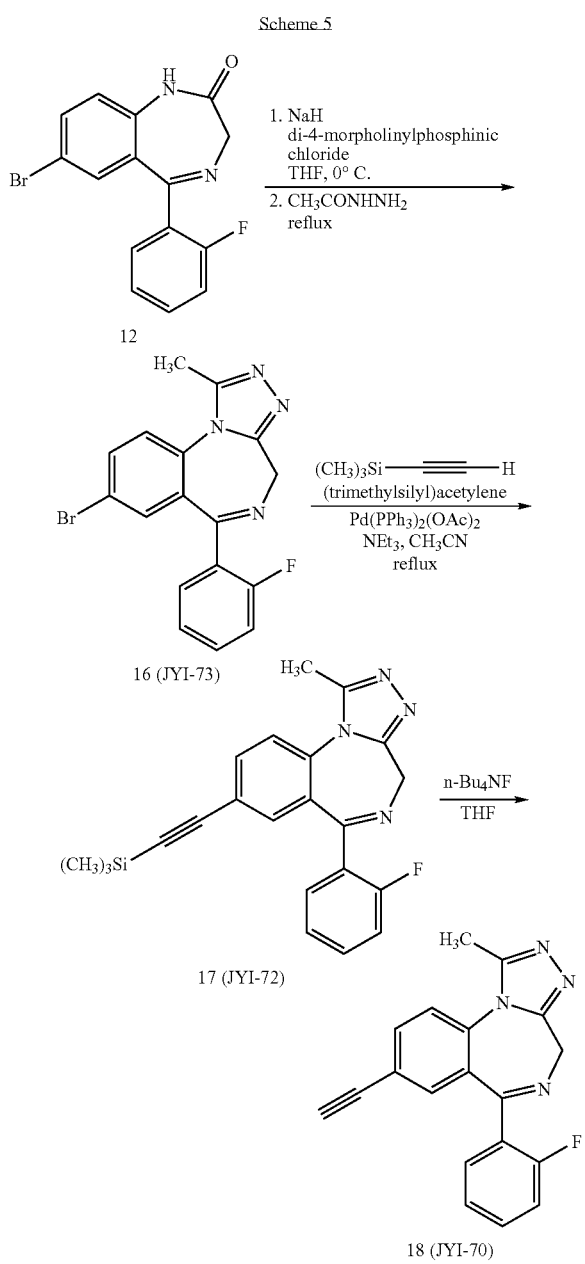

The 7-bromo-2'-fluorobenzodiazepine 12 was stirred with sodium hydride and di-4-morpholinylphosphinic chloride, followed by addition of acetic hydrazide, according to the published procedure[3] to provide triazolobenzodiazepine 16 (JYI-73), as illustrated in Scheme 5. This compound 16 underwent the palladium-mediated Heck-type coupling reactions with trimethylsilylacetylene to furnish the 8-trimethylsilyl substituted analog 17 (JYI-72). Removal of the silyl group from 17 furnished the 8-acetyleno triazolobenzodiazepine 18 (JYI-70).

Procedure:

8-Bromo-1-methyl-6-(2'-fluorophenyl)-4H-s-triazolo[4,3-a][1,4]benzodiazepine 16 (JYI-73).

A solution of 12 (JYI-032, 7.0 g, 21.0 mmol) in THF (50 mL) was cooled in ice-water, and sodium hydride (0.72 g, 18 mmol) was added in one portion. After 1 hour, di-4-morpholinylphosphinic chloride (4.84 g, 22.5 mmol) was added, and the solution which resulted was stirred continuously for 2 hours at room temperature. To this mixture was then added a solution of acetic hydrazide (2.47 g, 30 mmol) in n-BuOH (20 mL) and stirring was continued at room temperature for 15 min. The solvents were evaporated and the residue was dissolved in n-BuOH (25 mL) and heated to reflux for 2 hours. n-Butanol was evaporated and the residue was partitioned between $CH_2Cl_2$ and brine. The $CH_2Cl_2$ layer was dried and removed under reduced pressure after which the residue was purified by flash chromatography (silica gel, EtOAc) to afford 16 (JYI-73, 2.2 g, 40%) as a white solid: mp 213-214° C.; IR (KBr) 1610, 1484, 1426, 1314 cm$^{-1}$; $^1$H NMR (DMSO-d$_6$) δ 2.56 (s, 3H), 4.28 (d, 1H, J=12.9 Hz), 5.26 (d, 1H, J=12.9 Hz), 7.24 (t, 1H, J=8.3 Hz), 7.29 (t, 1H, J=7.2 Hz), 7.35 (s, 1H), 7.43-7.60 (m, 2H), 7.83 (d, 1H, J=8.7 Hz), 7.98 (dd, 1H, J=8.7 Hz and 2.3 Hz); MS (EI) m/e (relative intensity) 371 (5), 341 (34), 222 (100), 195 (19), 181 (28), 111 (72). Anal. Calcd. for $C_{17}H_{12}N_4FBr$: C, 55.01; H, 3.26; N, 15.09. Found: C, 54.76; H, 3.29; N, 14.74.

8-Trimethylsilylacetylenyl-1-methyl-6-(2'-fluorophenyl)-4H-s-triazolo[4,3-a][1,4]-benzodiazepine 17 (JYI-72).

A mixture of bromide 16 (JYI-73, 1.40 g, 3.8 mmol), trimethylsilylacetylene (0.65 g, 6.6 mmol) and bis(triphenylphosphine)palladium (II) acetate (0.25 g, 0.33 mmol) in a mixed solvent system of $CH_3CN$ (80 mL) and anhydrous triethylamine (50 mL) was heated to reflux under argon. After stirring for 2 hours at reflux, the mixture was cooled to room temperature and the precipitate which formed was removed by filtration. The filtrate was concentrated under reduced pressure and the residue was treated with a saturated aqueous solution of $NaHCO_3$ (40 mL), and extracted with $CHCl_3$ (3×50 mL). The combined organic extracts were washed with brine (2×10 mL) and dried ($Na_2SO_4$). After removal of solvent under reduced pressure, the residue was purified by flash chromatography (silica gel, EtOAc) to afford 17 (JYI-72, 1.15 g, 77%) as a gray solid: mp 218-219° C.; IR (KBr) 2958, 2157, 1612, 1537, 1493, 1452, 1317, 1249 cm$^{-1}$; $^1$H NMR (DMSO-d$_6$) δ 0.21 (s, 9H), 2.56 (s, 3H), 4.23 (s, 1H, J=12.9 Hz), 7.26 (t, 1H, J=8.4 Hz), 7.29-7.83 (m, 6H); MS (EI) m/e (relative intensity) 388 (65), 373 (14), 359 (77), 304 (44), 152 (100). Anal. Calcd. for $C_{22}H_{21}N_4SiF \cdot 0.7H_2O$: C, 65.87; H, 5.62; N, 13.94. Found: C, 65.88; H, 5.34; N, 13.94.

8-Acetyleno-1-methyl-6-(2'-fluorophenyl)-4H-s-triazolo[4,3-a][1,4]benzodiazepine 18 (JYI-70).

A solution of 17 (JYI-72, 2.0 g, 5 mmol) in THF (20 mL) was treated with Bu$_4$NF (4 mL, 1.0M solution in THF). The mixture which resulted was allowed to stir for 5 min at room temperature after which the mixture was added to $H_2O$ (20 mL) and extracted with $CH_2Cl_2$ (3×50 mL). The combined organic extracts were washed with brine (2×15 mL) and dried ($Na_2SO_4$). After removal of solvent under reduced pressure, the residue was purified by flash chromatography (silica gel, EtOAc/MeOH:100/1) to afford 18 (JYI-70, 1.1 g, 70%) as a pale yellow solid: mp>250° C. (dec); IR (KBr) 3205, 1612, 1493, 1426, 1317 cm$^{-1}$; $^1$H NMR (DMSO-d$_6$) δ 2.54 (s, 3H), 4.22 (d, 1H, J=12.9 Hz), 4.39 (s, 1H), 5.26 (d, 1H, J=12.9 Hz), 7.22 (t, 1H, J=8.3 Hz), 7.32-7.55 (m, 4H), 7.97 (m, 2H); MS (EI) m/e (relative intensity) 316 (72), 287 (100), 246 (69), 153 (16), 127 (62). Anal. Calcd. for C$_{19}$H$_{13}$N$_4$F·0.6 CH$_3$OH: C, 70.16; H, 4.37; N, 16.55. Found: C, 69.98; H, 4.31; N, 16.70.

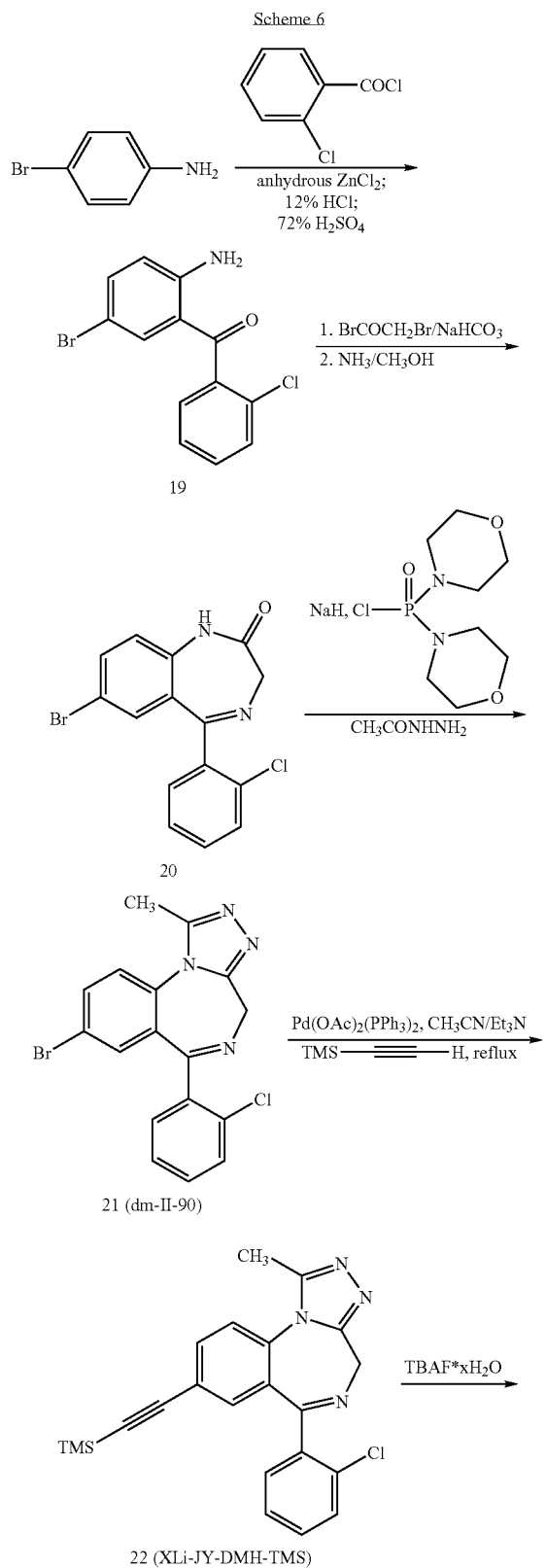

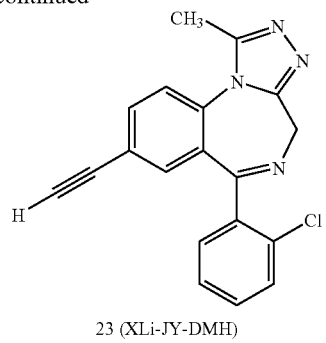

23 (XLi-JY-DMH)

2-Amino-5-bromo-2'-chlorobenzophenone 19 was obtained from simple starting materials, 4-bromoaniline and 2-chlorobenzoyl chloride, according to the improved conditions in the literature.[9] The benzodiazepine 20, available from reference 1, was stirred with sodium hydride and di-4-morpholinophosphinic chloride, followed by addition of acetylhydrazide to furnish triazolobenzodiazepine 21 (dm-II-90).[3] The ligand 22 (XLi-JY-DMH-TMS) was obtained by a Heck coupling reaction of 21 (dm-II-90) with trimethylsilylacetylene.[4,7,8] This compound was converted into acetylene 23 (XLi-JY-DMH)[7] on stirring with fluoride anion as shown in Scheme 6.

2-Amino-5-bromo-2'-chlorobenzophenone 19[9]

2-Chlorobenzoyl chloride (177 mL, 1.4 mol) was cooled in a 2-L flask equipped with a condenser and a thermometer to 0° C. with an ice-water bath and 4-bromoaniline (100 g, 0.58 mol) was added to the cooled solution. The mixture was heated to 120° C. and kept at this temperature for 1 h until analysis by TLC indicated 4-bromoaniline had been consumed (EtOAc:hexane, 1:4). The solution was heated to 160° C. and anhydrous ZnCl$_2$ (95 g, 0.70 mol, flamed dried) was added in one portion. The temperature was increased to 195° C. and stirring was maintained at this temperature for 3 hr until no more bubbles were evolved. The mixture was cooled to 120° C. and aq HCl (12%, 350 mL) was added dropwise slowly. The mixture was kept at reflux for 20 min, after which the aq layer was poured off. This procedure with aq HCl was repeated 4 times. Water (350 mL) was then added, and the mixture held at reflux for 20 min and then the water was poured off. This was repeated several times until the solid was not a block any more. Then H$_2$SO$_4$ (72%, 700 mL) was added to the residue and the mixture was heated to reflux for about 1 hr until the reaction mixture became a homogeneous dark colored solution. The hot acidic solution was poured into a mixture of ice and water with stirring. The precipitate which resulted was filtered and washed with a large amount of cold water until the pH value of the solid was about 6. The solid was then suspended in ice water and aq NaOH (40%, 290 mL) was added carefully. The mixture which resulted was stirred for 2 hrs. The solid was filtered and washed with ice water. The suspension of the solid in ice water was adjusted carefully to approximately pH=3 with aq H$_2$SO$_4$ (40%) dropwise. The solid which remained was filtered and washed with water to neutrality. The yellow solid 19 (66.1 g, 37.0%) was dried and used directly in the next step without further purification. $^1$H NMR (300 MHz, CDCl$_3$) δ 6.49 (s, br, 2H), 6.65 (d, 1H, J=8.82 Hz), 7.26-7.8 (m, 6H).

8-Bromo-5-(2'-chlorophenyl)-1-methyl-4H-s-triazolo[4,3-a]-1,4-benzodiazepine 21 (dm-II-90)[3]

A solution of benzodiazepine 20 (20 g, 57 mmol, available from reference 1) in dry THF (250 mL) was cooled to −5° C. and a 60% dispersion of sodium hydride (3.66 g, 92 mmol) was added in one portion. The mixture was allowed to warm to rt with stirring and the stirring was continued at rt until no more bubbles were evolved. The suspension was cooled to −5° C. after which di-4-morpholinylphosphinic chloride (21.8 g, 86 mmol) was added and this mixture was stirred for 30 min and allowed to warm to rt. The mixture was stirred for an additional 1.5 hr. To the mixture was then added a solution of acetylhydrazide (9.42 g, 114 mmol) in butanol (60 mL) and stirring was continued at rt for 10 min. The solvent was removed under reduced pressure and the residue was taken up in butanol (100 mL) and held at reflux for 2 hr. Butanol was removed under reduced pressure and the residue was partitioned between $CH_2Cl_2$ (200 mL) and $H_2O$ (100 mL). The aq layer was extracted 4 times and the organic layers combined. The organic layer was washed with brine and dried ($Na_2SO_4$). After the solvent was removed under reduced pressure, the residue was crystallized from $EtOAc-Et_2O$ to provide the pure triazolobenzodiazepine 21 (dm-II-90, 14 g, 63.2%) as a yellow solid: mp 265-267° C. [lit 274-275° C.][10]; IR (KBr) 3120 (br.), 1686, 1479, 1386, 1014, 827, 747 $cm^{-1}$; $^1H$ NMR (300 MHz, $CDCl_3$) δ 2.42 (s, 1H), 4.18 (d, 1H, J=12.9 Hz), 5.56 (d, 1H, J=12.9 Hz), 7.36 (m, 3H), 7.43 (m, 2H), 7.61 (m, 1H), 7.80 (dd, 1H, J=2.1 Hz, 8.7 Hz); MS (EI) m/e (rel intensity) 386 ($M^+$, 45), 357 (100); Anal. Calcd. For $C_{17}H_{12}N_4BrCl.0.5H_2O$: C, 51.65; H, 3.32; N, 14.18. Found C, 51.95; H, 2.97; N, 13.91.

8-Trimethylsilylacetylenyl-5-(2'-chlorophenyl)-1-methyl-4H-s-triazolo-[4,3-a]-1,4-benzodiazepine 22 (XLi-JY-DMH-TMS)[4,7,8]

A mixture of 21 (7.75 g, 20 mmol), acetonitrile (600 mL), triethylamine (500 mL) and bis(triphenylphosphine)-palladium (II) acetate (1.2 g, 1.6 mmol) was degassed. Trimethylsilylacetylene (5.65 mL, 40 mmol) was then added and the solution was degassed again. The solution was then heated to reflux for 4 hr until analysis by TLC indicated the starting material had disappeared. The mixture was cooled to rt and concentrated under reduced pressure. The residue was partitioned between $H_2O$ (50 mL) and EtOAc (2×200 mL). The combined organic layer was washed with brine and dried ($Na_2SO_4$). The residue was purified by flash chromatography on silica gel ($CHCl_3$) to furnish the trimethylsilyl analogue 22 (XLi-JY-DMH-TMS, 3 g, 37.0%) as white solid: mp 265-267° C.; IR (KBr) 2930, 1618, 1554, 1497, 1429, 1316, 885, 847 $cm^{-1}$; $^1H$ NMR (300 MHz, $CDCl_3$) δ 0.24 (s, 9H), 2.65 (s, 3H), 4.15 (d, 1H, J=12.9 Hz), 5.52 (d, 1H, J=12.9 Hz), 7.35-7.45 (m, 5H), 7.61 (m, 1H), 7.72 (dd, 1H, J=1.8 Hz, 8.4 Hz); MS (EI) m/e (rel intensity) 404 ($M^+$, 90), 375 (100); Anal. Calcd. For $C_{22}H_{21}N_4SiCl$: C, 65.33; H, 5.24; N, 13.86. Found: C, 64.99; H, 4.98; N, 13.79.

8-Acetyleno-5-(2'-chlorophenyl)-1-methyl-4H-s-triazolo-[4,3-a]-1,4-benzodiazepine 23 (XLi-JY-DMH)[7]

A solution of benzodiazepine 22 (1.25 g, 31 mmol) in THF (250 mL) was cooled to −30° C. and treated with $Bu_4NF.xH_2O$ (0.97 g, 37 mmol). After the mixture was stirred for 5 min, analysis by TLC (silica gel; EtOAc:EtOH 4:1) indicated starting material had disappeared. Water (70 mL) was then added and the mixture was allowed to warm to rt. The mixture was then extracted with EtOAc (2×200 mL). The organic layer was washed with brine and dried ($Na_2SO_4$). After removal of the solvent under reduced pressure, the residue was washed successively with ethyl ether, ethyl acetate and chloroform. After drying, the title compound 23 (XLi-JY-DMH) was obtained (1.0 g, 97.3%) as a white solid: mp>250° C. (dec); IR (KBr) 3185, 1623, 1543, 1497, 1429, 756 $cm^{-1}$; $^1H$ NMR (300 MHz, $CDCl_3$) δ 2.65 (s, 3H), 3.17 (s, 1H), 4.18 (d, 1H, J=12.9 Hz), 5.54 (d, 1H, 12.9 Hz), 7.34(m, 2H), 7.41-7.45 (m, 3H), 7.6 (m, 1H), 7.75 (dd, 1H, J=1.8 Hz, 8.4 Hz); MS (EI) m/e (rel intensity) 332 ($M^+$, 78) 303 (100).

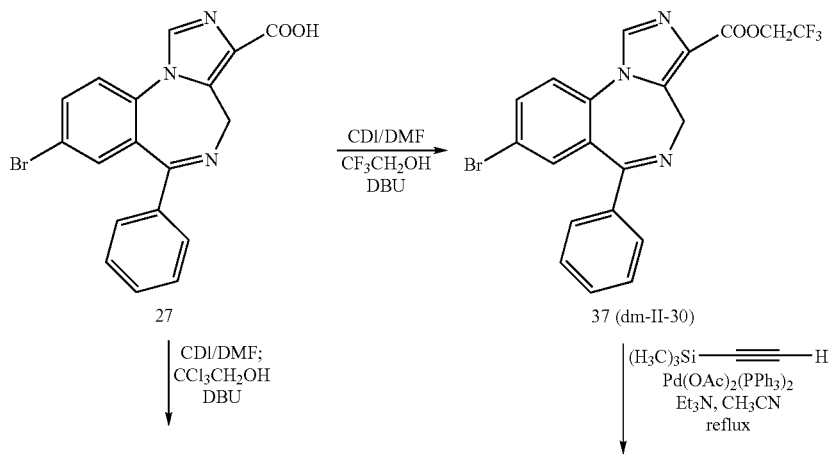

Scheme 7

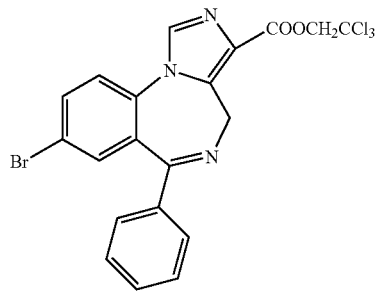

38 (dm-II-33)

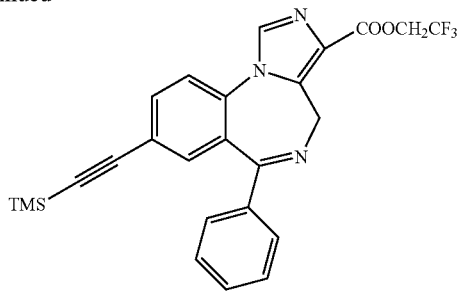

39 (dm-II-35)

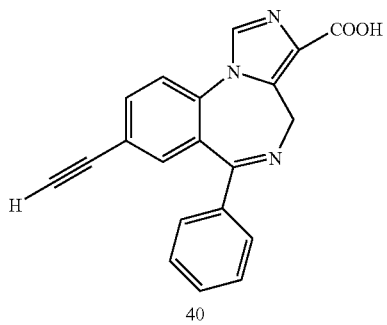

40

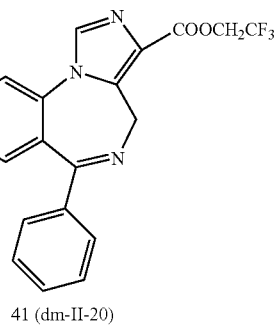

41 (dm-II-20)

Esters 37 (dm-II-30), 38(dm-II-33) and 41 (dm-II-20) were prepared according to the general procedure described in item [0067] from the starting acids and different alcohols, respectively. The bromide 37 was converted into the trimethlyacetylenyl compound 39 (dm-II-35) under standard conditions (Pd-mediated, Heck-type coupling)[4,7,8] (Scheme 7).

General Procedure for Preparing the Esters.

The acid was dissolved in DMF (10 mL/mmol S.M.) and CDI (1.2 eq) was added. The reaction mixture was stirred at room temperature for 3 h followed by addition of the alcohol (10 eq) and DBU (1 eq). The stirring was maintained until the disappearance of all the starting material as determined by TLC (EtOAc:EtOH 4:1). The reaction mixture was then quenched by adding water. The solid which precipitated was filtered and washed with ethyl ether. It was purified by flash chromatography (EtOAc) on silica gel or neutral aluminum oxide for ester 38.

Trifluoroethyl 8-bromo-6-phenyl-4H-benzo[f]imidazo[1,5-a][1,4]diazepine-3-carboxylate 37 (dm-II-30)

A white solid (69.1%) from acid 27 and 2,2,2-trifluoroethanol: mp 202-204° C.; IR (KBr) 3114, 1711, 1608, 1495, 1368, 1288, 1158 cm$^{-1}$; $^1$H NMR (300 MHz, CDCl$_3$) δ 4.10 (d, 1H, J=12.6 Hz), 4.68 (m, 1H), 4.85 (m, 1H), 6.02 (d, 1H, J=12.6 Hz), 7.41-7.54 (m, 6H), 7.62 (d, 1H, J=2.1 Hz), 7.83 (dd, 1H, J=2.1 Hz, 8.4 Hz), 7.97 (s, 1H); MS (EI) m/e (rel intensity) 463 (M$^+$, 14), 465 (14).

Trichloroethyl 8-bromo-6-phenyl-4H-benzo[f]imidazo[1,5-a][1,4]diazepine-3-carboxylate 38 (dm-II-33)

A white solid (90.9%) from acid 27 and 2,2,2-trichloroethanol: mp 113-116° C.; IR (KBr) 3434, 1728, 1610, 1493, 1270, 1146, 1128 cm$^{-1}$; $^1$H NMR (300 MHz, CDCl$_3$) δ 4.11 (d, 1H, J=12.6 Hz), 4.91 (d, 1H, J=12.0 Hz), 5.19 (d, 1H, J=12.0 Hz), 6.12 (d, 1H, J=12.6 Hz), 7.41-7.54 (m, 6H), 7.61 (d, 1H, J=2.1 Hz), 7.83 (dd, 1H, J=2.1 Hz, 8.4 Hz); MS (EI) m/e (rel intensity) 511 (M$^+$, 45).

Trifluoroethyl 8-trimethylsilylacetylenyl-6-phenyl-4H-benzo[f]imidazo[1,5-a][1,4]diazepine-3-carboxylate 39 (dm-II-35)

A white solid (49.8%): mp 107-110° C.; IR (KBr) 2961, 1734, 1611, 1560, 1497, 1251, 1159, 1120, 846 cm$^{-1}$; $^1$H NMR (300 MHz, CDCl$_3$) δ 0.25 (s, 9H), 4.08 (d, 1H, J=12.3 Hz), 4.69 (m, 1H), 4.84 (m, 1H), 5.98 (d, 1H, J=12.3 Hz), 7.39-7.57 (m, 7H), 7.76 (dd, 1H, J=1.8 Hz, 8.4 Hz); MS (EI) m/e (rel intensity) 481 (M$^+$, 100).

Trifluoroethyl 8-acetylenyl-6-phenyl-4H-benzo[f]imidazo[1,5-a][1,4]diaze-pine-3-carboxylate 41 (dm-II-20)

A white solid (36.9%) from acid 40 and 2,2,2-trifluoroethanol: mp 188-190° C.; IR (KBr) 3443, 3277, 1710, 1600, 1492, 1366, 1280, 1156 cm$^{-1}$; $^1$H NMR (500 MHz, CDCl$_3$) δ 3.18 (s, 1H), 4.08 (d, 1H, J=12.5 Hz), 4.67 (m, 1H), 4.82 (m, 1H), 5.98 (d, 1H, J=12.5 Hz), 7.37-7.40 (m, 2H), 7.44-7.51 (m, 3H), 7.56-7.59 (m, 2H), 7.78 (dd, 1H, J=1.5 Hz, 8.5 Hz); MS (EI) m/e (rel intensity) 409 (M$^+$, 28). Anal. Calcd. For $C_{22}H_{14}N_3O_2F_3 \cdot 0.25H_2O$: C, 63.82; H, 3.72; N, 10.16. Found: C, 63.89; H, 3.37; N, 9.94.

Scheme 8:

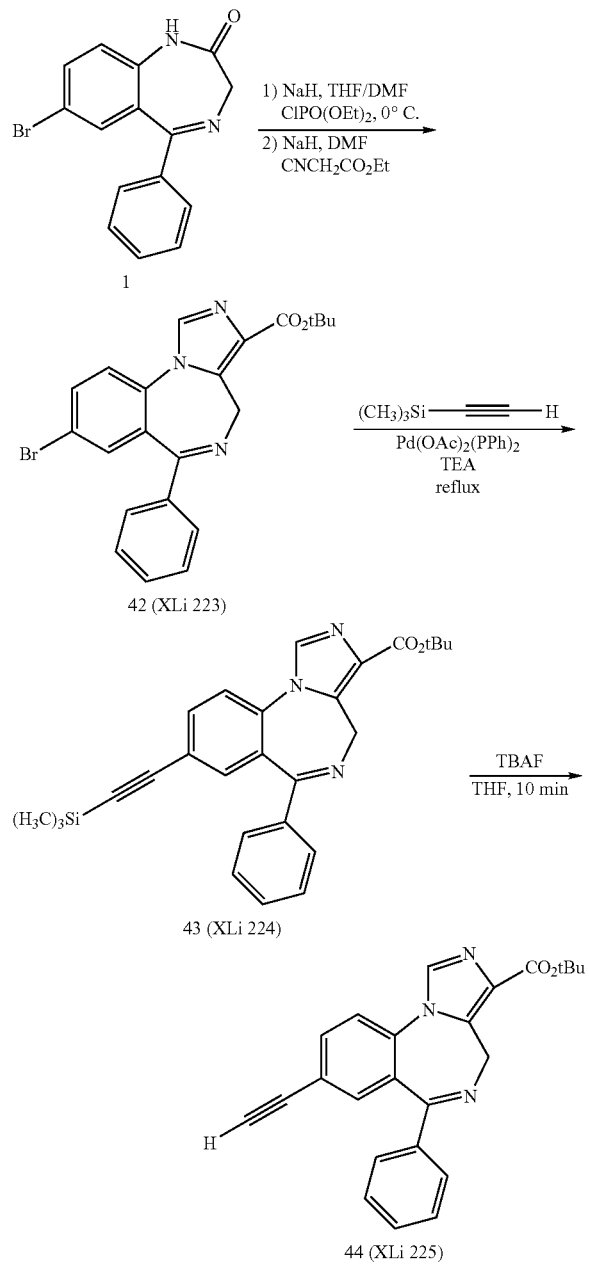

(XLi223): mp: 222°-223° C.; IR (KBr) 2975, 2358, 1717, 1608, 1557, 1277, 1073, 908, 696, 652 cm$^{-1}$; $^1$H NMR (CDCl$_3$) δ 1.60 (s, 9H), 4.03 (d, 1H, J=12.5 Hz), 6.08 (d, 1H, J=12.4 Hz), 7.35-7.52 (m, 7H), 7.58 (d, 1H, J=2.2 Hz), 7.80 (dd, 1H, J=2.22 Hz and 8.55 Hz), 7.93 (s, 1H);

t-Butyl-8-trimethylsilylacetylenyl-6-phenyl-4H-benzo[f]imidazo[1,5-a][1,4]-diazepine-3-carboxylate 43 (XLi 224).[4,5,8]

A mixture of bromide 42 (1 g, 2.28 mmol, trimethylsilylacetylene (559 mg, 5.69 mmol) and bis(triphenylphosphine)-palladium-(I) acetate (55 mg, 0.073 mmol) in a mixed solvent system of CH$_3$CN (15 mL) and anhydrous TEA (25 mL) was heated to reflux under argon. After stirring for 6 hours at reflux, the mixture was cooled to room temperature and the precipitate which formed was removed by filtration. The filtrate was concentrated under reduced pressure and the residue was treated with a saturated aqueous solution of NaHCO$_3$ (20 mL), and extracted with CHCl$_3$ (3×25 mL). The combined extracts were washed with brine and dried (Na$_2$SO$_4$). After removal of solvent under reduced pressure, the residue was purified by flash chromatography (silica gel, EtOAc) to afford 43 (XLi224) as a white solid (710 mg, 68.9%). mp:234°-236° C.; IR (KBr) 2973, 2357, 2154, 1719, 1611, 1493, 1366, 1250, 1152, 1075, 946, 880 cm$^{-1}$; $^1$H NMR (CDCl$_3$) δ 0.23 (s, 9H), 1.64 (s, 9H), 4.05 (d, 1H, J=12.7 Hz), 6.06 (d, 1H, J=12.4), 7.37-7.53 (m, 7H), 7.73 (dd, 1H, J=1.95 and 8.25 Hz), 7.92 (s, 1 H); MS (EI) m/e (relative intensity) 427 (M$^+$, 76), 412 (5), 381 (55), 353 (100) 303 (10), 287 (7).

t-Butyl 8-acetylenyl-6-phenyl-4H-benzo[f]imidazo[1,5-a][1,4]diazepine-3-carboxylate 44 (XLi 225).[7]

A solution of 43 (128 mg, 0.281 mmol), in THF (15 mL) was treated with Bu$_4$NF.H$_2$O (100.04 mg, 0.38 mmol). The mixture which resulted was allowed to stir for 5 min at room temperature after which the mixture was added to H$_2$O (10 mL) and extracted with EtOAc (3×15 mL). The combined organic extracts were washed with brine (15 mL) and dried (Na$_2$SO$_4$). After removal of solvent under reduced pressure, the residue was purified by a wash column (silica gel, EtOAc) to furnish 44 (XLi225) (92 mg, 85.4%) as a white solid: mp:221°-223° C.; IR (KBr) 3159, 3107, 2092, 1721, 1606 cm$^{-1}$; $^1$H NMR (CDCl$_3$) δ 1.62 (s, 9H), 3.21 (s, 1H), 4.12 (d, 1H, J=10.2 Hz), 6.07 (d, 1H, J=12.5 Hz), 7.35-7.53 (m, 7H), 7.73 (dd, 1H, J=1.8 Hz and 8.3 Hz), 7.92 (s, 1H).

The bromide 1 was reacted with diethylphosphorochloridate in the presence of sodium hydride, followed by addition of t-butyl isocyanoacetate to provide the ester 42. This was converted into the trimethylsilylacetyleno compound 43 under standard conditions (Pd-mediated, Heck-type coupling).[8] Treatment of 43 with fluoride gave the title compound 44.

Procedure for XLi225 t-Butyl 8-bromo-6-phenyl-4H-benzo[f]imidazo[1,5-a][1,4]diazepine-3-carboxylate 42.

This benzodiazepine 42 was obtained in 40% yield from 1[1] analogous to the literature procedure[2] as a white solid. 42

Scheme 9

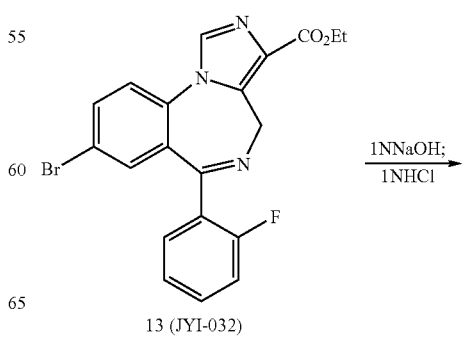

13 (JYI-032)

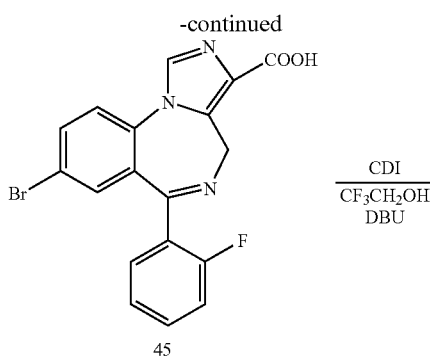

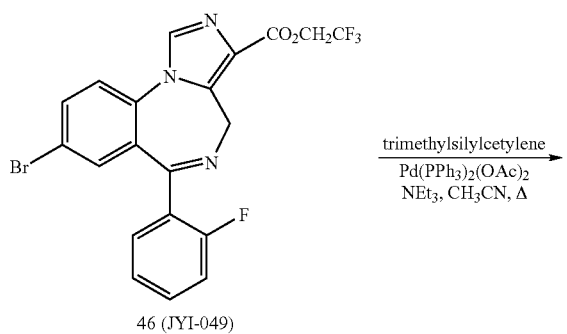

46 (JYI-049)

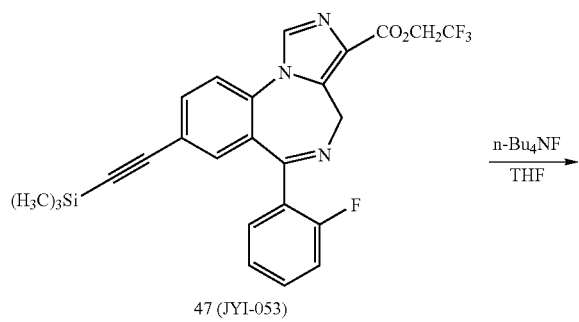

47 (JYI-053)

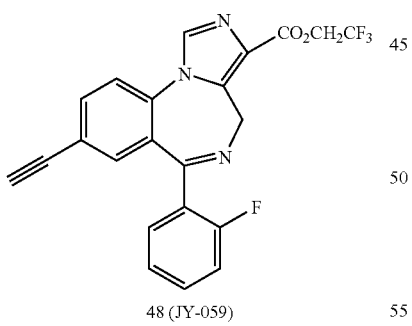

48 (JY-059)

7-Bromo-2'-fluorobenzodiazepine 13 was hydrolyzed with aq 2 N sodium hydroxide in EtOH and acidified to pH 4 by adding 1 N HCl to afford the acid 45. The acid, obtained from the ester 13, was stirred with CDI in DMF, followed by stirring with trifluoroethanol and DBU to provide the ester 46 (JYI-049). This material 46 was heated with trimethysilylacetylene in a Heck-type coupling reaction[8] to provide the trimethylsilyl analog 47 (JYI-053). The silyl group was removed from 47 on treatment with tetrabutylammonium fluoride to furnish 48 (JYI-059) in 70% yield.

Procedure:

8-Bromo-6-(2'-fluorophenyl)-4H-benzo[f]imidazo[1,5-a][1,4]diazepine-3-carboxylic acid 45.

The ester 13 (1.0 g, 2.36 mmol) was dissolved in EtOH (80 mL) and 2 N aq NaOH (8 mL) was added to the solution. The mixture was stirred at rt for 4 hours. After the EtOH was removed under reduced pressure, the solution was allowed to cool. The pH value was adjusted to 4 by adding 1 N HCl dropwise. The mixture was filtered and the solid was washed with cold water and ethyl ether. The solid was dried to afford 45 (0.96 g, 97%) as a white solid: mp 280° C. (dec); IR (KBr) 3419, 1740, 1611, 1491 cm$^{-1}$; $^1$H NMR (DMSO-d$_6$) δ 4.11 (bs, 1H), 5.99 (bs, 1 H), 7.20 (t, 1 H, J=8.5 Hz), 7.32 (t, 1 H, J=7.5 Hz), 7.38 (d, 1 H, J=1.8 Hz), 7.55 (m, 2 H), 7.84 (d, 1 H, J=8.7 Hz), 7.95 (dd, 1 H, J=8.6, 1.9 Hz), 8.35 (s, 1 H). MS (EI) m/e (relative intensity) 400 (72), 399 (85), 381 (100), 355 (82).

Trifluoroethyl-8-bromo-6-(2'-fluorophenyl)-4H-benzo[f]imidazo[1,5-a][1,4]diazepine-3-carboxylate 46 (JYI-049).

The carboxylic acid 45 (0.89 g, 2.23 mmol) was dissolved in dry DMF (20 mL), after which CDI (0.72 g, 4.45 mmol) was added at rt and the mixture was stirred for 12 hours. The trifluoroethanol (0.49 mL, 6.68 mmol) in DMF (1 mL) and DBU (0.37 mL, 2.45 mmol) in DMF (1 mL) were then added to the mixture and stirring continued overnight. The solvent was evaporated under reduced pressure and the residue was purified by flash chromatography (silica gel, hexanes/EtOAc:3/1) to afford 46 (JYI-049, 0.81 g, 76%) as a white solid: mp 223-224° C.; IR (CHCl$_3$) 3063, 1732, 1611, 1492 cm$^{-1}$; $^1$H NMR (CDCl$_3$) δ 4.16 (bs, 1 H), 4.80 (bs, 2 H), 6.07 (bs, 1 H), 7.06 (dt, 1 H, J=8.3, 0.9 Hz), 7.30 (m, 2 H), 7.48 (m, 2 H), 7.68 (dt, 1 H, J=7.6, 1.8 Hz), 7.80 (dd, 1 H, J=8.6, 2.1 Hz), 8.11 (s, 1 H). MS (EI) m/e (relative intensity) 483 (38), 383 (64), 355 (100). Anal. Calcd. for C$_{20}$H$_{12}$N$_3$O$_2$F$_4$Br: C, 49.81; H, 2.51; N, 8.71. Found: C, 49.97; H, 2.44; N, 8.68.

Trifluoroethyl-8-trimethylsilylacetylenyl-6-(2'-fluorophenyl)-4H-benzo[f]imidazo[1,5-a][1,4]diazepine-3-carboxylate 47 (JYI-053).

A mixture of bromide 46 (JYI-049, 482 mg, 1.0 mmol), trimethylsilylacetylene (0.28 mL, 2.0 mmol) and bis(triphenylphosphine)palladium (II) acetate (75 mg, 0.1 mmol) in a mixed solvent system of CH$_3$CN (25 mL) and anhydrous triethylamine (25 mL) was heated to reflux under argon. After stirring for 12 h at reflux, the mixture was cooled to room temperature and the precipitate which formed was removed by filtration. The filtrate was concentrated under reduced pressure and the residue was treated with a saturated aq solution of NaHCO$_3$ (40 mL), and extracted with CHCl$_3$ (3×100 mL). The combined organic extracts were washed with brine (2×50 mL) and dried (Na$_2$SO$_4$). After removal of solvent under reduced pressure, the residue was purified by flash chromatography (silica gel, hexanes/EtOAc:3/1) to afford 47 (JYI-053, 360 mg, 76%) as a gray solid: mp 220-221° C.; IR (CHCl$_3$) 2960, 1741, 1612, 1496 cm$^{-1}$; $^1$H NMR (CDCl$_3$) δ 0.25 (s, 9 H), 4.12 (bs, 1 H), 4.82 (bs, 2 H), 6.10 (bs, 1 H), 7.06 (t, 1 H, J=8.3 Hz), 7.30 (m, 1 H), 7.48 (m, 2 H), 7.56 (d, 1 H, J=8.3 Hz), 7.67 (m, 1 H), 7.73 (dd, 1 H, J=8.3, 1.8 Hz), 8.02 (s, 1 H); MS (EI) m/e (relative intensity) 499 (52), 399 (45), 371 (100), 235 (21), 178 (36).

Anal. Calcd. for $C_{25}H_{21}N_3O_2F_4Si$: C, 60.11; H, 4.24; N, 8.41. Found: C, 60.27; H, 4.22; N, 8.33.

Trifluoroethyl-8-acetyleno-6-(2'-fluorophenyl)-4H-benzo[f]imidazo-[1,5-a][1,4]diazepine-3-carboxylate 48 (JYI-059).

A solution of 47 (JYI-053, 475 mg, 1.0 mmol) in THF (15 mL) was treated with $Bu_4NF$ (2 mL, 1.0M solution in THF). The mixture, which resulted, was allowed to stir for 5 min at room temperature after which the mixture was added to ethyl acetate/hexanes to afford 48 (JYI-059, 299 mg, 70%) as a pale yellow solid: mp 192-193° C.; IR ($CHCl_3$) 3295, 3052, 1741, 1612, 1494, 1277, 1159 cm$^{-1}$; $^1$H NMR ($CDCl_3$) δ 3.14 (s, 1 H), 4.17 (bs, 1 H), 4.78 (bs 2 H), 4.47 (s, 1 H), 6.05 (bs, 1 H), 7.05 (dt, 1 H, J=8.3, 0.8 Hz), 7.30 (m, 1 H), 7.48 (m, 2H), 7.60 (d, 1 H, J=8.3 Hz), 7.68 (dt, 1 H, J=7.6, 1.8 Hz), 7.76 (dd, 1 H, J=10.1, 1.8 Hz), 8.02 (s, 1 H); MS (EI) m/e (relative intensity) 427 (37), 327 (26), 299 (100), 178 (50). Anal. Calcd. for $C_{22}H_{13}N_3O_2F_4$: C, 61.83; H, 3.07; N, 9.83. Found: C, 61.94; H, 3.03; N, 9.68.

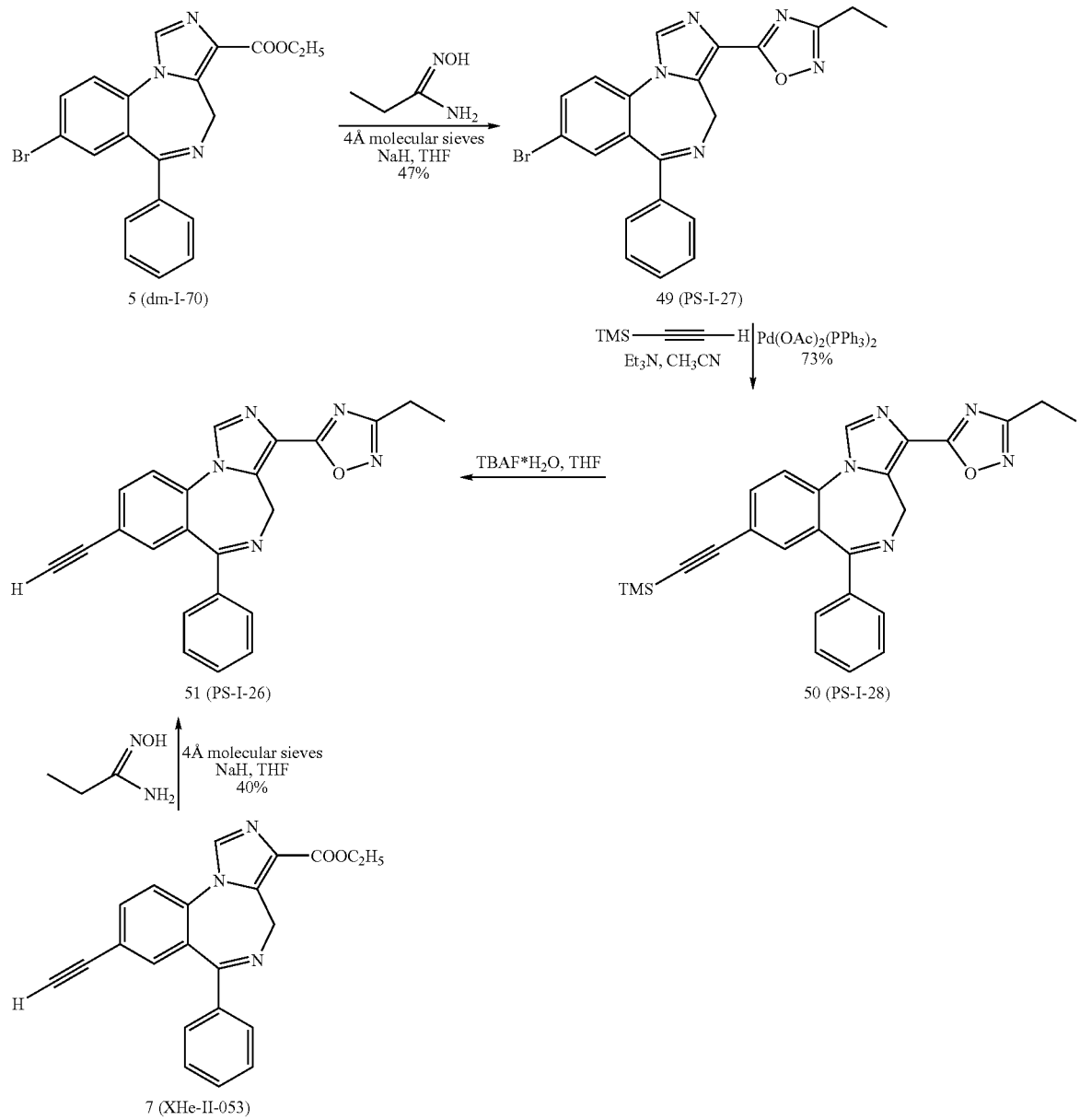

Scheme 10

$H_2O$ (5 mL) and extracted with EtOAc (3×10 mL). The combined organic extracts were washed with brine (2×10 mL) and dried ($Na_2SO_4$). The solvent was removed under reduced pressure and the residue was recrystallized from Ethyl amido oxime (59.5 mg, 0.676 mmol) was added to a stirred suspension of powdered 4A molecular sieves (75 mg) in anhydrous THF (15 mL) under nitrogen. After the mixture was stirred at rt for 10 min, NaH (27 mg of 60% in mineral oil, 0.676 mmol) was added to the mixture. After the mixture was stirred for a further 30 min, a solution of the forgoing ester 7 (XHeII-053, 120 mg, 0.338 mmol) in THF (20 mL) was added. The mixture which resulted was heated to reflux for 8 hr. It was cooled to rt, after which acetic acid (40.6 mg, 0.676 mmol) was added. After the solution was stirred for 10 min, the mixture was filtered through celite. The filtrate was diluted with $CH_2Cl_2$ (50 mL) and washed with water, brine and dried ($K_2CO_3$). Evaporation of the solvent under reduced pressure afforded a pale yellow solid, which was purified by flash column chromatography (silica gel, EtOAc/hexane, 2:3) to furnish 51 as a white solid (PS-1-26, 52 mg, 40%). mp: 221-222° C.; IR (KBr) 3297, 3105, 1631, 1570, 1495, 1310, 938 cm$^{-1}$; $^1$H NMR (CDCl$_3$) δ 8.07 (s, 1H), 7.80 (dd, 1H, J=8.4 Hz, J=1.8 Hz), 7.64-7.60 (m, 2H), 7.53-7.37 (m, 5H), 6.12 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); $^{13}$C NMR (CDCl$_3$) δ 171.8, 170.6, 168.8, 139.1, 136.6, 135.8, 135.4 (2C), 135.1, 130.7, 129.3 (2C), 128.3 (2C), 128.1, 124.7, 122.7, 121.6, 81.2, 80.0, 44.7, 19.7, 11.5; MS (m/z) 379 (100).

This compound 49 (PS-1-27) was obtained in 47% yield from 5 (dm-1-70) analogous to the procedure employed in [0085] as a white solid. mp: 210° C.; IR (KBr) 3106, 1631, 1563, 1493, 1147, 931, 698 cm$^{-1}$; $^1$H NMR (CDCl$_3$) δ 8.06 (s, 1H), 7.84 (dd, 1H, J=8.6 Hz, J=2.25 Hz), 7.63-7.38 (m, 7H), 6.13 (d, 1H, J=12.9 Hz), 4.21 (d, 1H, J=12.9 Hz), 3.20 (s, 1H), 2.88 and 2.83 (ABq, 2H, J=7.6 Hz), 1.41 (t, 3H, J=7.6 Hz); MS (m/z) 435 (100).

To the suspension of compound 49 (PS-1-27, 0.5 g, 1.15 mmol) in acetonitrile (30 mL) and triethylamine (80 mL) was added bis(triphenylphosphine)palladium (II) acetate (0.086 g, 0.115 mmol). The solution was degassed and trimethylsilylacetylene (0.33 mL, 2.3 mmol) added. The mixture was heated to reflux and stirred overnight. After removal of the solvent, the residue was dissolved in $CH_2Cl_2$ and washed with a saturated aqueous solution $NaHCO_3$ and brine. The organic layer was dried ($Na_2SO_4$) filtered and concentrated under vacuum. The residue was purified by flash column chromatography (EtOAc:hexane 2:3) to furnish the trimethylsilyl analog 50 (PS-1-28, 380 mg, 73%) as a pale yellow solid: mp: 193-194° C.; IR (KBr) 3106, 2960, 2149, 1630, 1567, 1493, 938, 851, 701 cm$^{-1}$; $^1$H NMR (300 Hz, CDCl$_3$) δ 8.07 (s, 1H), 7.78 (dd, 1H, J=1.86, 8.34 Hz), 7.61-7.38 (m, 7H), 6.11 (d, J=12.78 Hz), 4.19 (d, J=12.78 Hz), 2.88 and 2.83 (ABq, 2H, J=7.56 Hz), 1.41 (t, 3H, J=7.56 Hz), 0.25 (s, 9H).

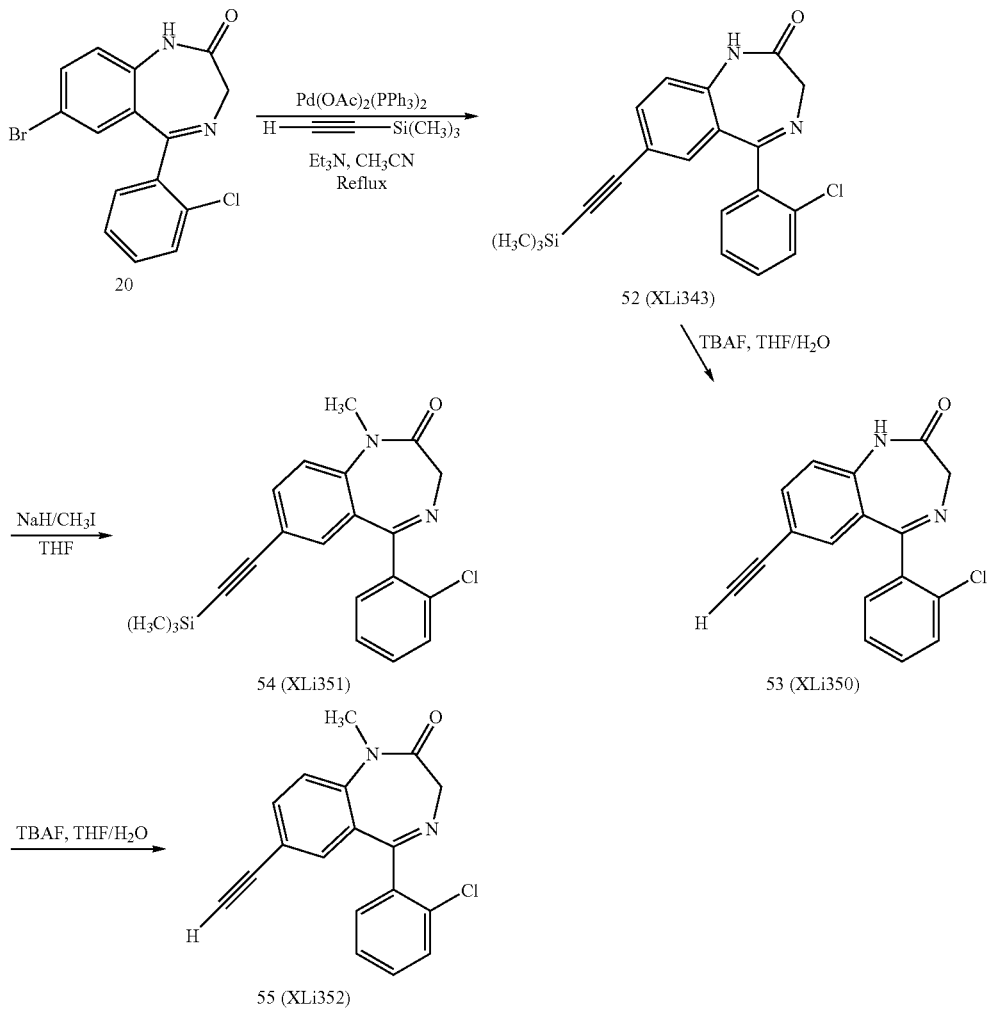

Scheme 11

The bromide 20 available from references 9 and 10 was reacted with trimethylsilyacetylene in the presence of a palladium catalyst to provide trimethylsilyl analog 52. This product was methylated with methyl iodide/sodium hydride to give the N-methyl benzodiazepine 54 (XLi 351). This was subjected to fluoride-mediated desilation to furnish 53 (XLi 350) and 55 (XLi 352).

Procedure for XLi 350 and XLi 352

7-Trimethylsilylacetyleno-5-phenyl-(2'-chlorophenyl)1,3-dihydrobenzo[e]-1,4-diazepin-2-one 52 (XLi 343).[4,5,8]

A mixture of 20[1] (500 mg, 1.43 mmole) available from references 9 and 10 in triethyl amine (10 mL) and $CH_3CN$ (16 mL) with trimethyl-silylacetylene (126 mg, 1.28 mmole) and bis(triphenylphosphine)palladium (II) acetate (64.3 mg, 0.086 mmol) was heated to reflux under nitrogen. After 6 hours, the reaction mixture was cooled to room temperature and filtered. The filtrate was concentrated under vacuum and the residue was treated with a saturated aqueous $NaHCO_3$ solution (15 mL), and extracted with $CH_2Cl_2$ (3×20 mL). The organic layers were combined and washed with brine and dried ($Na_2SO_4$). After removal of solvent under reduced pressure, the residue was purified via flash chromatography (silica gel, EtOAc/hexanes:1/1) to furnish 52 as a yellow powder (310 mg, 59%): mp: 225.8-228.2° C.; IR (KBr) 2953, 2358, 1685, 1616, 1490, 1328, 1248, 1058, 1011, 841, 746 $cm^{-1}$, $^1H$ NMR ($CDCl_3$) δ 0.21 (s, 9H), 4.38 (s, 2H), 7.41 (d, 1H, J=8.37 Hz), 7.19-7.52 (br, 7H), 8.11 (s, 1H); MS (EI) m/e (relative intensity) 366 ($M^+$, 100), 331(59), 229 (18), 161(26).

7-Acetyleno-5-phenyl-(2'-chlorophenyl)-1,3-dihydro-benzo[e]-1,4-diazepin-2-one 53 (XLi 350):[7] A solution of 52 (150 mg, 0.408 mol) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried over ($Na_2SO_4$). The solvent was removed under vacuum and the residue which resulted was passed through a wash column (silica gel, EtOAc/hexanes:4/1) to give 55 as light yellow crystals (110 mg, 95.2%); mp: 215° C.; IR (KBr) 3290, 1685, 1615, 1491, 1328, 731 $cm^{-1}$, $^1H$ NMR ($CDCl_3$) δ 3.06 (s, 1H), 4.40 (s, 3H), 7.03-7.61 (m, 7H), 7.58-7.86 (m, 2H), 7.99 (s, 1H); MS (EI) m/e (relative intensity) 294 ($M^+$, 100), 266(75), 265 (87), 259(83), 231(40), 201(24), 176(23).

1-Methyl-7-trimethylsilylacetyleno-5-phenyl-(2'-chlorophenyl)-1,3-dihydro-benzo[e]-1,4-diazepin-2-one 54 (XLi 351).7

A mixture of 52 (300 mg, 0.82 mmol) was dissolved in dry THF (40 mL) at 0° C. and NaH (60% in mineral oil, 50 mg, 1.25 mmol) was added to the solution in one portion. The slurry was then stirred for 20 min at 0° C. and $CH_3I$ (139 mg, 0.98 mmol) was added to the mixture and it was warmed up to room temperature. After the mixture stirred for 3 hours at room temperature, the THF was then removed under reduced pressure. The residue was purified by flash chromatography [hexanes/EtOAc (1:4)] to provide the title compound 54 (260 mg, 83%) as a white solid: mp: 196.9-198° C.; IR (KBr) 2953, 1676, 1611, 1489, 1346, 1125, 1078, 913, 742 $cm^{-1}$; $^1HNMR$ ($CDCl_3$) δ(ppm) 0.21(s, 9H) 3.46 (s, 3H), 3.54 (d, 1H, J=10.9 Hz), 4.60 (d, 1H, J=10.8 Hz), 7.20-7.43 (m, 5H), 7.58-7.65 (m, 3H). MS (EI) m/e (relative intensity) 380($M^+$, 8), 366(10), 308(100), 280(88), 273(97), 245(61).

1-Methyl-7-acetyleno-5-phenyl-(2'-chlorophenyl)-1,3-dihydro-benzo[e]-1,4-diazepin-2-one 55 (XLi 352):[7]

A solution of 54 (100 mg, 0.262) in THF (30 mL) was treated with tetrabutylammonium fluoride (1M in THF). The mixture was stirred for 20 minutes at room temperature before water (30 mL) was added. The mixture was then extracted with EtOAc (3×30 mL). The combined organic extracts were washed with brine and dried ($Na_2SO_4$). The solvent was removed under vacuum and the residue which resulted was passed through a wash column (silica gel, EtOAc/hexanes:4/1) to give 55 as light yellow crystals (71 mg, 90%): mp: 95.6-98.1° C.; IR (KBr) 2953, 1677, 1489, 1346, 1091, 791, 749 $cm^{-1}$, $^1H$ NMR ($CDCl_3$) δ (ppm) 3.05(s, 1H), 3.46 (s, 3H), 3.83 (d, 1H, J=10.5 Hz), 4.87 (d, 1H, J=9.33 Hz), 5.28 (s, 1H), 7.20-7.43 (m, 5H), 7.58-7.86 (m, 2H); MS (EI) m/e (relative intensity) 308($M^+$, 100), 294(19), 280(82), 273(99), 249(28), 245(61), 229(29), 201 (32), 189(43).

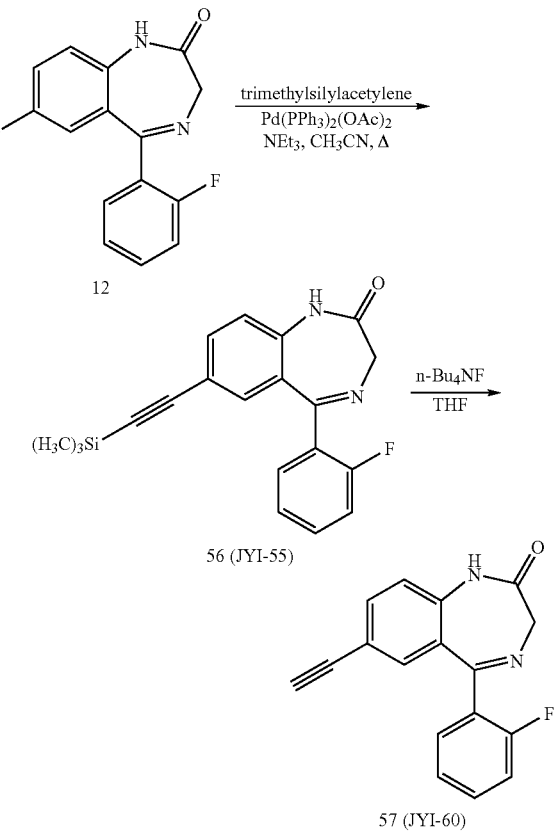

Scheme 12

7-Trimethylsilylacetyleno-5-(2'-fluorophenyl)-1,3-dihydrobenzo[e]-1,4-diazepine-2-one 56 (JYI-55).

A mixture of bromide 12 (1.6 g, 5.0 mmol), trimethylsilyl-acetylene (3.0 mL, 21.0 mmol) and bis(triphenylphosphine) palladium (II) acetate (375 mg, 0.5 mmol) in a mixed solvent system of $CH_3CN$ (60 mL) and anhydrous triethylamine (40 mL) was heated to reflux under argon. After stirring for 3 h at reflux, the mixture was cooled to room temperature and the precipitate which formed was removed by filtration. The filtrate was concentrated under reduced pressure and the residue was treated with a saturated aq solution of NaHCO$_3$ (100 mL), and extracted with CHCl$_3$ (3×200 mL). The combined organic extracts were washed with brine (2×100 mL) and dried (Na$_2$SO$_4$). After removal of solvent under reduced pressure, the residue was purified by flash chromatography (silica gel, hexanes/EtOAc:2/1) to afford 56 (JYI-55, 794 mg, 47%) as a gray solid: mp 168.5-169.5° C.; IR (CHCl$_3$) 3202, 3113, 2955, 1686, 1612, 1490 cm$^{-1}$; $^1$H NMR (CDCl$_3$) δ 0.22 (s, 9 H), 4.38 (s, 2 H), 7.04-7.33 (m, 3 H), 7.34 (s, 1 H), 7.45-7.53 (m, 1 H), 7.56-7.62 (m, 2 H), 8.73 (bs, 1 H). MS (EI) m/e (relative intensity) 350 (94), 322 (100), 167 (41), 153 (37). Anal. Calcd. for C$_{20}$H$_{19}$N$_2$OFSi: C, 68.54; H, 5.46; N, 7.99. Found: C, 68.23; H, 5.40; N, 8.34.

7-Acetyleno-5-(2'-fluorophenyl)-1,3-dihydrobenzo[e]1,4-diazepine-2-one 57 (JYI-60).

A solution of 56 (JYI-55, 700 mg, 2.0 mmol) in THF (200 mL) was treated with Bu$_4$NF (2 mL, 1.0M solution in THF). The mixture, which resulted, was allowed to stir for 5 min at room temperature after which the mixture was added to H$_2$O (5 mL) and extracted with EtOAc (3×10 mL). The combined organic extracts were washed with brine (2×10 mL) and dried (Na$_2$SO$_4$). After the solvent was removed under reduced pressure, the residue was purified by flash chromatography (silica gel, hexanes/EtOAc:2/1) to afford 57 (JYI-60, 400 mg, 72%) as a pale yellow solid: mp 208-209.5° C.; IR (CHCl$_3$) 3290, 3110, 2930, 1685, 1612, 1489 cm$^{-1}$; $^1$H NMR (CDCl$_3$) δ 3.04 (s, 1 H), 4.40 (s, 2 H), 7.06-7.28 (m, 3 H), 7.38 (s, 1 H), 7.44-7.51 (m, 1 H), 7.59-7.62 (m, 2 H), 9.43 (bs, 1 H). MS (EI) m/e (relative intensity) 278 (80), 250 (100). Anal. Calcd. for C$_{17}$H$_{11}$N$_2$OF: C, 73.37; H, 3.98; N, 10.07. Found: C, 73.64; H, 3.92; N, 9.78.

Scheme 13

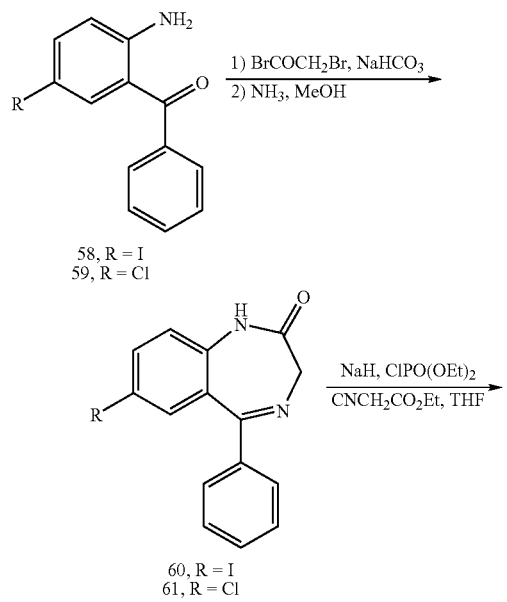

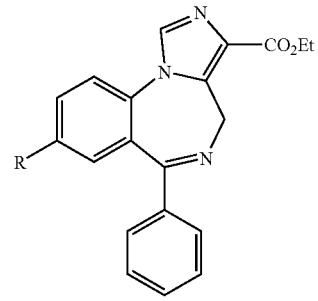

62, R = I (Hz120)
61, R = Cl (Hz111)

2-Amino-5-iodo-benzophenone was prepared from p-iodonitrobenzene and phenylacetonitrile according to the literature.[11] 2-Amino-5-chloro-benzophenone was commercially available from Acros. The benzodiazepine 60 was reacted with diethylphosphorochloridate in the presence of sodium hydride, followed by the addition of ethyl isocyanoacetate to provide the ester 62 (Hz120), as shown in Scheme 13.

Ethyl 8-iodo-6-phenyl-4H-benzo[f]imidazo[1,5-a][1,4]diazepine-3-carboxylate 62.

A solution of benzodiazepine 60 (3 g, 8.3 mmol) in dry THF (36 mL) was cooled to 0° C. and a 60% dispersion of sodium hydride (0.70 g, 17.4 mmol) was added in one portion. The mixture was allowed to warm to rt with stirring and the stirring was continued at rt until no more bubbles were evolved. The suspension was cooled to 0° C. after which diethylphosphorochloridate (2.29 g, 13.3 mmol) was added and this mixture was stirred for 30 min and allowed to warm to rt. The mixture was stirred for an additional 1.5 hr. In another flask, a 60% dispersion of sodium hydride (0.70 g, 17.4 mmol) in mineral oil was added in dry THF (36 mL) and cooled to 0° C. Ethyl isocyanoacetate (1.13 g, 9.94 mmol) was added and the stirring was continued until no more bubbles were evolved. This mixture was transferred to the above mixture at 0° C. The mixture was then stirred at rt for 6 h and quenched with HOAc (3.2 mL). The mixture was partitioned between EtOAc (200 mL) and H$_2$O (50 mL). The organic layer was washed with brine and dried (Na$_2$SO$_4$). After the solvent was removed under reduced pressure, the residue was purified by flash chromatography (silica gel, gradient elution, EtOAc:hexane 1:4, 1:1, 4:1) to provide the ester 62 (Hz120) in 43% yield as a light brown solid. mp: 221-222° C.; IR (KBr) 2977, 1717, 1608, 1489 cm$^{-1}$; $^1$H NMR (DMSO-d$_6$) δ 1.31 (t, 3H, J=7.1 Hz), 4.10 (d, 1H, J=12.5 Hz), 4.29 (q, 2H, J=6.7 Hz), 5.75 (d, 1H, J=12.4 Hz), 7.40-7.50 (m, 5H), 7.63 (d, 1H, J=1.8 Hz), 7.69 (d, 1H, J=8.5 Hz), 8.13 (dd, 1H, J=1.9, 8.5 Hz), 8.36 (s, 1H); MS (EI) m/e (relative intensity) 458 (23), 457 (M$^+$, 100), 411 (62), 384 (29), 383 (100), 257 (29). Anal. Calcd. for C$_{20}$H$_{16}$IN$_3$O$_2$: C, 52.53; H, 3.53; N, 9.19. Found: C, 52.57, H, 3.73; N, 8.64.

Ethyl 8-chloro-6-phenyl-4H-benzo[f]imidazo[1,5-a][1,4]diazepine-3-carboxylate 63.

This ester 63 was obtained in 52% yield from 61 analogous to the procedure employed in [0092] as a white solid. mp: 174-175° C. (lit.[12] 174-175° C.); $^1$HNMR (DMSO-d$_6$) δ 1.32 (t, 3H, J=7.1 Hz), 4.13 (d, 1H, J=12.3 Hz), 4.32 (q, 2H, J=6.7 Hz), 5.76 (d, 1H, J=12.3 Hz), 7.37-7.50 (m, 6H), 7.86-8.38 (m, 2H), 8.74 (s, 1H).

Scheme 14
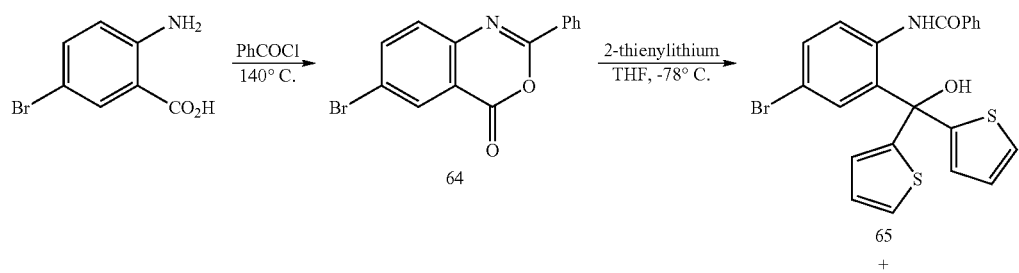
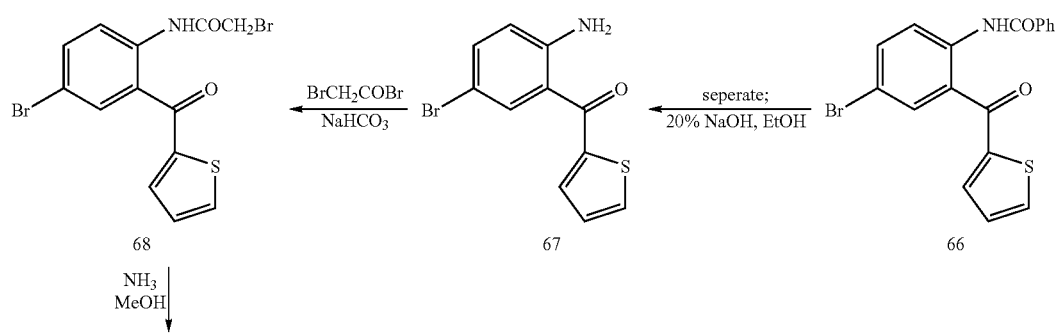
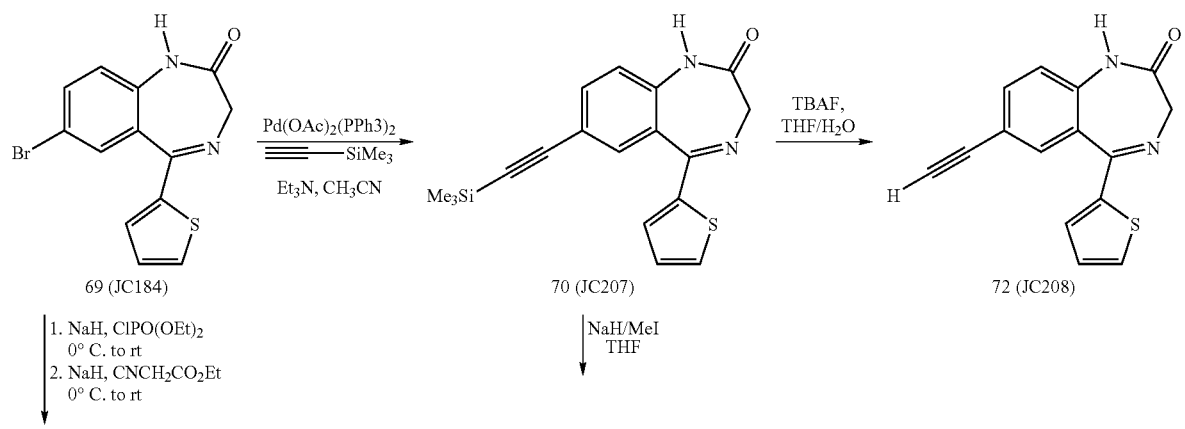
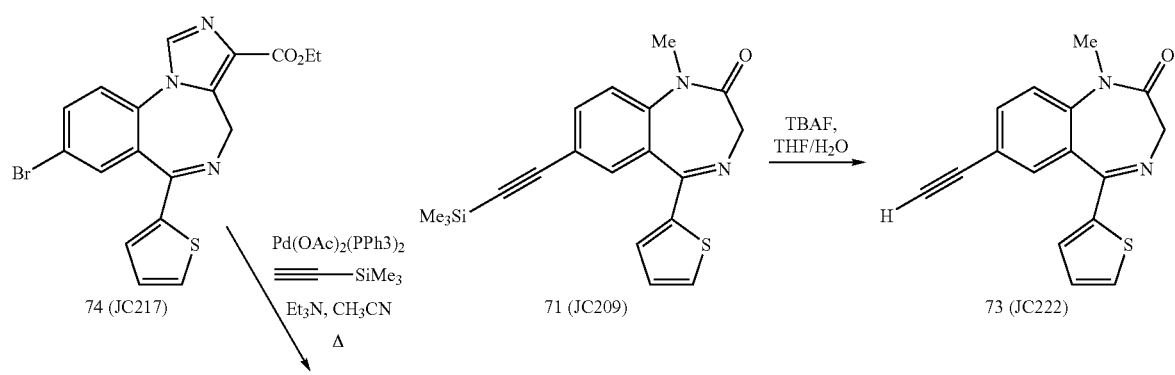

-continued

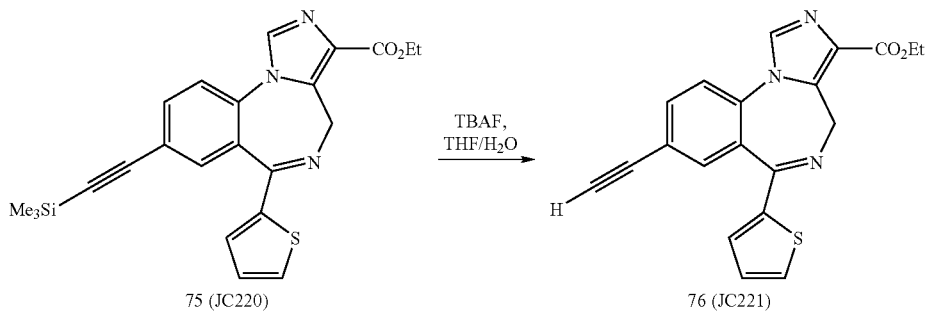

75 (JC220) → TBAF, THF/H₂O → 76 (JC221)

6-Bromo-2-phenyl-4H-benzo[2,3-d]-1,3-oxazin-4-one 64.

The 2-amino-5-bromobenzoic acid (5 g, 23.1 mmol) was treated with benzoyl chloride (237 mL, 2.04 mol) at 140° C. for 3 h. After the reaction mixture was cooled to rt, the crystals that formed were collected by filtration and were washed with hexanes to provide 64 as light brown needles (6.8 g, 97%): $^1$H NMR (CDCl$_3$) δ 7.51-7.2 (m, 4H), 7.9 (dd, 1H, J=2.3, 8.6 Hz), 8.30-8.33 (m, 2H), 8.8 (d, 1H, J=2.2 Hz); $^{13}$C NMR (CDCl$_3$) δ 158.19, 157.35, 145.75, 139.58, 132.82, 130.97, 129.77, 128.82, 128.73, 128.29, 121.37, 118.27; MS (EI) m/e (relative intensity) 303 (M$^+$, 36), 301 (M$^+$, 36), 259 (14), 257 (14), 226 (6), 224 (6), 178 (9), 170 (9), 168 (9), 151 (4), 105 (100).

4-Bromo-2-(2'-thienylcarbonyl)-N-benzoylaniline 66 and bis-(2'-thienyl)-[5-bromo-2-(N-benzoyl)-amino]phenylmethanol 65.

The benzo-xazinone 64 (5.0 g, 16.6 mmol) was dissolved in dry THF (250 mL) and cooled to −78° C. for 45 min. The 2-thienyllithium (18.21 mL of 1M solution in THF) was added dropwise over 35 min and the reaction was stirred at −78° C. for 1.2 h. Saturated aq NH$_4$Cl solution (25 mL) and Et$_2$O (30 mL) were then added. The organic layer was separated, washed with brine and dried (MgSO$_4$). The solvent was removed under reduced pressure, and the residue was purified via flash chromatography (silica gel, hexanes/EtOAc: 1:0, 49:1, 20:1, 11:1, 5:1) to provide 66 as yellow crystals and the alcohol 65. 66: $^1$H NMR (CDCl$_3$) δ 7.23 (dd, 1H), 7.52-7.56 (m, 3H), 7.66 (dd, 1H, J=0.99, 3.8 Hz), 7.82 (d, 1H, J=5.0 Hz), 7.99-8.02 (m, 3H), 7.75 (d, 1H, J=9.0 Hz), 11.2 (s, 1H); $^{13}$C NMR (CDCl$_3$) δ 188.82, 165.45, 143.24, 138.79, 136.57, 135.90, 135.51, 134.25, 134.03, 132.17, 128.81, 128.31, 127.26, 125.65, 123.45, 114.95; MS (EI) m/e (relative intensity) 387 (M$^+$, 12), 385 (M$^+$, 12), 276 (18), 274 (18), 201 (7), 172 (7), 105 (100). 65: $^1$H NMR (CDCl$_3$) δ 4.20 (s, 1H), 6.82 (s, 2H), 6.96-7.01 (m, 3H), 7.33-7.38 (m, 7H), 7.65 (d, 2H, J=7.23 Hz), 8.43 (d, 1H, J=8.8 Hz), 9.92 (s, 1H); $^{13}$C NMR (CDCl$_3$) δ 165.04, 148.94, 136.44, 135.49, 134.49, 132.34, 131.59, 131.40, 128.40, 127.20, 126.89, 126.58, 124.18, 116.00, 79.35, 76.92, 76.50; MS (EI) m/e (relative intensity) 471 (M$^+$, 54), 469 (M$^+$, 51), 453 (100), 451 (93), 348 (96), 346 (92), 316 (54), 314 (58), 282 (20), 280 (19), 267 (88), 235 (12), 234 (12), 223 (15), 222 (17), 201 (56), 173 (20), 172 (12), 158 (10), 129 (10).

5-Bromo-2-(2'-thienylcarbonyl)aniline 67.

The amide 66 (2 g, 635 mmol) was dissolved in EtOH (150 mL) and 20% NaOH solution (30 mL) was added. The mixture was heated to reflux for 5 h and the EtOH was removed under reduced pressure. The mixture was extracted with EtOAc and the organic phases were combined, washed with brine and dried (Na$_2$SO$_4$). The solvent was removed under reduced pressure, and the residue was purified via a wash column (silica gel, hexanes/EtOAc: 11:1 to 4:1) to provide 67 as a bright yellow solid: $^1$H NMR (DMSO-d$_6$) δ 6.28 (br s, 2H), 6.82 (s, 1H), 6.90 (s, 1H), 7.26 (dd, 1H, J=3.8, 5.0 Hz), 7.42 (dd, 1H, J=2.4, 8.9 Hz), 7.61 (dd, 1H, J=1.1, 3.8 Hz), 7.69 (dd, 1H, J=2.4 Hz), 8.04 (dd, 1H, J=1.1, 5.0 Hz); $^{13}$C NMR (DMSO) δ 187.42, 150.09, 143.87, 136.46, 134.75, 134.41, 133.93, 128.78, 119.36, 119.17, 104.95; MS (EI) m/e (relative intensity) 283 (M$^+$, 59), 282 (M$^+$, 87), 281 (M$^+$, 59), 280 (M$^+$, 79), 250 (23), 248 (23), 201 (13), 199 (49), 197 (48), 172 (25), 170 (23), 145 (13), 140 (1), 111 (100), 101 (33).

4-Bromo-2-(2'-thienylcarbonyl)-N-bromoacetylaniline 68.

The thienylaniline 67 (3.3 g, 11.7 mmol) and NaHCO$_3$ (2.9 g, 34.5 mmol) were suspended in dry CHCl$_3$ (180 mL) and cooled to 0° C. A solution of bromoacetyl bromide (1.12 mL, 12.9 mmol) in dry CHCl$_3$ (30 mL) was added dropwise over 20 min at 0° C. and the mixture was stirred at rt for 3 h. The CHCl$_3$ solution was then washed with aq NaHCO$_3$ (5%) and dried (Na$_2$SO$_4$). The CHCl$_3$ was removed under reduced pressure, and Et$_2$O was added to the flask. The solution was sonicated and filtered to provide 68 as a light solid: mp: 144.0-146.5° C.; $^1$H NMR (CDCl$_3$) δ 4.01 (s, 2H), 7.23-7.26 (m, 1H), 7.24 (d, 1H), 7.65 (d, 1H), 7.74 (d, 1H), 7.84 (d, 1H), 8.46 (d, 1H), 10.85 (br s, 1H); MS (EI) m/e (relative intensity) 405 (M$^+$, 69), 404 (40), 403 (M$^+$, 100), 401 (M+, 66), 324 (39), 322 (38), 310 (33), 308 (33), 292 (32), 283 (65), 282 (72), 281 (65), 280 (67), 266 (10), 264 (10), 250 (34), 248 (35), 226 (55), 224 (55), 201 (43), 199 (27), 197 (27), 173 (32), 111 (73).

7-Bromo-5-(2'-thienyl)-1,3-dihydrobenzo[e][1,4] diazepine 69 (JC184).

The bromoacetyl amide 68 (0.236 g, 0.586 mmol) was dissolved in a saturated solution of anhydrous ammonia in MeOH (50 mL) and the mixture was heated to reflux for 6 h. After the MeOH was removed under reduced pressure, EtOAc was added to the residue. The solution was sonicated and then filtered to provide 69 (JC184) as a light solid: MS (EI) m/e (relative intensity) 322 (M$^+$, 54), 320 (M$^+$, 53), 294 (100), 292 (98), 211 (24), 185 (31), 140 (21). The material was used directly in the next step.

7-Trimethylsilylacetylenyl-5-(2'-thienyl)-1,3-dihydrobenzo[e][1,4]diazepine 70 (JC207).

A mixture of 69 (1 g, 3.12 mmol) in CH$_3$CN (20 mL) and Et$_3$N (30 mL) was degassed and heated to reflux under nitrogen. Bis(triphenylphosphine)-palladium (II) acetate (0.26 g, 0.347 mmol) was then quickly added, followed by the addition of TMS acetylene (0.76 g, 7.78 mmol). The mixture was stirred at reflux for 4 h and the solvent was removed under reduced pressure. Water (25 mL) and EtOAc (25 mL) were added to the residue and the mixture was filtered through celite to remove the organometallic species. The filtrate was then extracted with EtOAc and the organic phases were combined, washed with brine and dried (Na$_2$SO$_4$). The solvent was removed under reduced pressure and the residue was purified via flash chromatography (silica gel, hexanes/EtOAc: 11:1, 5:1) to provide 70 (JC207) as a light yellow solid: mp: 198.5-201° C.; MS (EI) m/e (relative intensity) 338 (M$^+$, 68), 337 (M$^+$, 28), 310 (100), 295 (13), 161 (13), 147 (33), 105 (17). The material was used directly in the next step.

7-Acetylenyl-5-(2'-thienyl)-1,3-dihydrobenzo[e][1,4]diazepine 72(JC208).

A solution of 70 (150 mg, 0.457 mmol) in THF (30 mL) was treated with tetrabutylammonium fluoride (1M in THF) at 0° C. for 5 minutes. Water (20 mL) was subsequently added to quench the reaction and the THF was removed under reduced pressure. The remaining aq solution was then extracted with EtOAc and the organic phases were combined, washed with brine and dried (Na$_2$SO$_4$). Upon removal of the solvent, Et$_2$O was added to the residue which was sonicated and then filtered to provide the title compound 72 (JC208, 111 mg, 91%) as an ivory colored solid: mp: 214-216° C.; MS (EI) m/e (relative intensity) 266 (M$^+$, 61), 265 (M$^+$, 30), 238 (100), 237 (49), 210 (13), 209 (10), 164 (6), 153 (7), 139 (7). This material was used in the next step.

1-N-methyl-7-trimethylsilylacetylenyl-5-(2'-thienyl)-1,3-dihydrobenzo[e][1,4]diazepine 71 (JC209).

Thiophere 70 (500 g, 1.52 mmol) was dissolved in dry THF (25 mL) at 0° C. and NaH (60% in mineral oil, 76 mg, 1.50 mmol) was added to the solution in one portion. After the mixture was stirred at 0° C. for 30 min, MeI (0.14 mL, 2.25 mmol) was added and the ice bath was allowed to warm to rt. The mixture was allowed to stir for 3 h and the THF was then removed under reduced pressure. The residue was purified via flash chromatography (silica gel, hexanes/EtOAc 8:1, 4:1) to provide the title compound 71 (JC209) as a white solid: mp: 171.3-173.6° C.; $^1$H NMR (CDCl$_3$) δ 0.26 (br s, 9H), 3.38 (s, 3H), 4.71 (d, 1H), 7.09 (dd, 1H, J=3.7, 5.0 Hz), 7.17 (dd, 1H, J=1.1, 3.7 Hz), 7.30 (s, 1H), 7.49 (dd, 1H, J=1.1, 5.0 Hz), 7.65 (dd, 1H, J=2.0, 8.5 Hz), 7.75 (d, 1H); $^{13}$C NMR (CDCl$_3$) δ (CDCl$_3$) δ 170.12, 163.22, 143.65, 143.14, 134.69, 133.12, 131.38, 130.14, 127.77, 127.47, 121.01, 119.10, 103.01, 95.66, 56.38, 34.67; MS (EI) m/e (relative intensity) 352 (M$^+$, 71), 351 (M$^+$, 60), 337 (10), 324 (100), 309 (24), 168 (28), 154 (38).

1-N-methyl-7-acetyleno-5-(2'-thienyl)-1,3-dihydrobenzo[e][1,4]diazepine 73 (JC222).

The same procedure for preparing 72 (JC208) was applied to 73 (JC222) and a very light brown solid resulted: mp: 218.3-220.4° C.; $^1$H NMR (CDCl$_3$) δ 3.16 (s, 1H), 3.39 (s, 3H), 3.78 (d, 1H, J=11.07 Hz), 4.72 (d, 1H, J=5.9 Hz), 7.08 (dd, 1H, J=3.8, 5.0 Hz), 7.31 (d, 1H, J=8.6 Hz), 7.49 (dd, 1H, J=1.0, 5.0 Hz), 7.67 (dd, 1H, J=2.0, 8.5 Hz), 7.79 (d, 1H, J=1.9 Hz); $^{13}$C NMR (CDCl$_3$) □ 171.04, 170.07, 163.12, 143.49, 134.79, 133.50, 131.34, 130.25, 127.85, 127.46, 121.16, 117.99, 81.83, 78.30, 56.34, 34.69. MS (EI) m/e (relative intensity) 281 (13), 280 (M$^+$, 60), 279 (51), 253 (19), 252 (100), 251(2), 235 (11), 209(10).

Ethyl 8-bromo-6-(2'-thienyl)-4H-benzo[f]imidazo[1,5-a][1,4]diazepine-3-carboxylate 74 (JC217).

Dry THF (30 mL) was added to a flask containing the benzodiazepine 69 (1.27 g, 3.96 mmol) and the solution was allowed to cool to 0° C. and NaH (60% in mineral oil, 0.191 g, 4.76 mmol) was quickly added. The mixture was stirred for 30 min at 0° C. and then removed from an ice bath to stir another 1 h at rt. Prior to adding ClPO(OEt)$_2$ (1.06 g, 6.35 mmol), the mixture was again pre-cooled to 0° C. The solution was stirred another 3 h as the ice bath warmed to rt. Meanwhile, dry THF (10 mL) was added to a second flask containing NaH (60% in mineral oil, 0.229 g, 5.72 mmol). After the second mixture was cooled to 0° C., CNCH$_2$CO$_2$Et was added dropwise and the solution continued to stir for 30 min at 0° C. After both reaction mixtures were again pre-cooled to 0° C., the two solutions were combined under Ar via cannula and the solution stirred at rt overnight. The reaction was quenched with ice water and worked up with EtOAc, and the combined organic phases were washed with brine and dried (Na$_2$SO$_4$). The solvent was removed under reduced pressure and the residue was purified via flash chromatography (silica gel, hexanes:EtOAc 4:1, 1:1, 1:3) to provide the title compound 74 (JC217) as an ivory solid (500 mg, 30% yield): mp: 204.0-205.3° C.; $^1$H NMR (CDCl$_3$) δ 1.45 (t, 3H, J=7.1, 14.3 Hz), 4.07 (d, 1H, J=8.8 Hz), 4.44 (dd, 2H, J=3.8, 4.7 Hz), 5.98 (d, 1H, J=12.8 Hz), 7.05 (d, 1H, J=10 Hz), 7.07 (s, 1H), 7.46-7.49 (m, 2H), 7.83 (dd, 1H, J=2.2, 8.5 Hz), 7.91 (s, 1H), 7.96 (d, 1H, J=2.2 Hz): MS (EI) m/e (relative intensity) 418 (M$^+$, 15), 417 (M$^+$, 68), 416 (M$^+$, 15), 415 (M$^+$, 64), 407 (22), 344 (26), 343 (100), 342 (30), 341 (93), 293 (15), 291 (21), 262 (18), 235 (15), 211 (12), 154 (10), 127 (11).

Ethyl 8-trimethylsilylacetylenyl-6-(2-thienyl)-4H-benzo[f]imidazo[1,5-a][1,4]diazepine-3-carboxylate 75 (JC220).

The same procedure for preparing 70 (JC207) was applied to 75 (JC220) and an ivory colored solid resulted: $^1$H NMR (CDCl$_3$) δ 0.29 (s, 9H), 1.45 (t, 3H, J=7.1, 14.3 Hz), 4.0 (d, 1H, J=18.1 Hz), 4.45 (dd, 2H, J=7.2, 8.5 Hz), 5.97 (d, 1H, J=12.8 Hz), 7.06-7.11 (m, 2H), 7.49 (dd, 1H, J=1.2, 5.0 Hz), 7.52 (d, 1H, J=8.3 Hz), 7.77 (dd, 1H, J=1.9, 8.3 Hz), 7.90 (d, 1H, J=1.8 Hz), 7.93 (s, 1H). MS (EI) m/e (relative intensity) 433 (M$^+$, 74), 387 (49), 359 (100), 277 (28), 262 (19), 235 (24), 172 (19), 129(17).

Ethyl 8-acetyleno-6-(2'-thienyl)-4H-benzo[f]imidazo[1,5-a][1,4]diazepine-3-carboxylate 76 (JC221).

The same procedure for preparing 72 (JC208) was applied to 76 (JC221) and an ivory colored solid resulted: mp: >198° C.; $^1$H NMR (CDCl$_3$) δ 1.43 (t, 3H, J=4.3, 11.4 Hz), 3.25 (s, 1H), 4.10 (d, 1H, J=12.8 Hz) 4.40-4.49 (m, 2H), 5.99 (d, 1H, J=12.9 Hz), 7.50 (d, 1H, J=5.0 Hz), 7.56 (d, 1H, J=8.3 Hz), 7.81 (dd, 1H, J=1.8, 8.3 Hz), 7.95 (s, 1H); MS (EI) m/e (relative intensity) 361, (M$^+$, 24), 315 (35), 287 (100), 237 (26), 178 (30), 153 (21), 126 (18). MS (EI) m/e (relative intensity) 361 (M$^+$, 29), 315 (41), 287 (100), 237 (31), 178 (40), 153 (26), 126 (21).

Scheme 15

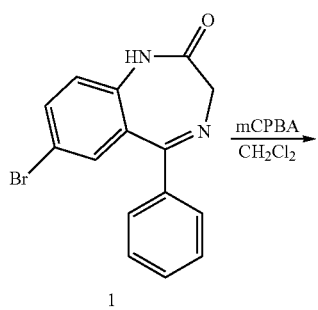

1

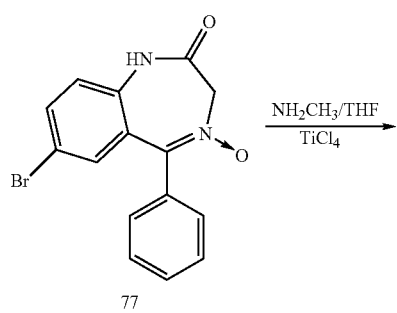

77

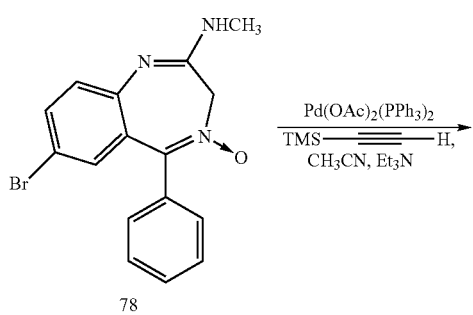

78

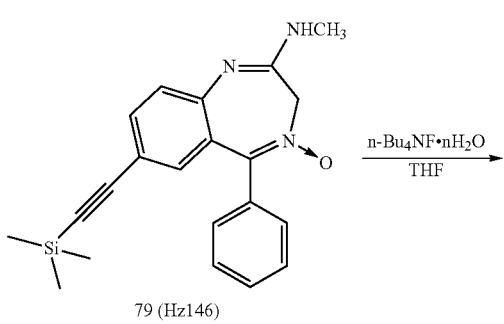

79 (Hz146)

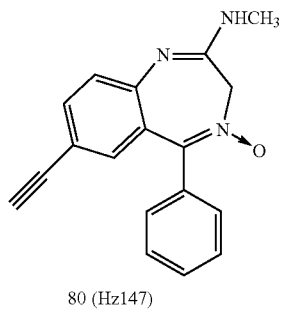

80 (Hz147)

Scheme 16

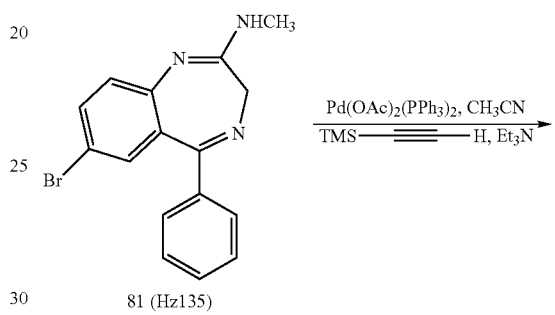

81 (Hz135)

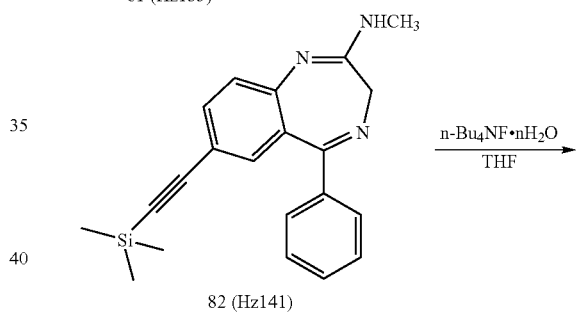

82 (Hz141)

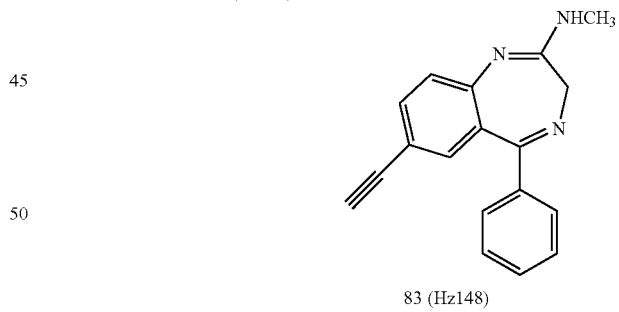

83 (Hz148)

The benzodiazepine 1 was oxidized with 3-chloroperoxybenzoic acid (mCPBA) to form 77, followed by the addition of methylamine to afford amidine 78. N-Oxide 78 was reacted with trimethylsilyacetylene in the presence of a palladium catalyst to provide the trimethylsilyl analog 79 (Hz146) which was subjected to fluoride-mediated desilation to afford 80 (Hz147), as shown in Scheme 15. In a related route, bromide 81 was converted into the trimethylsilylacetylene 82 (Hz141). This analog was then transformed into target 79 (Hz146) with mCPBA or the key target (Hz148) or treatment with fluoride (Scheme 16).

7-Bromo-4-oxy-5-phenyl-1,3-dihydro-benzo[e][1,4]diazepin-2-one 77.

Bromide 1 (1.88 g, 5.95 mmol) was dissolved in CH$_2$Cl$_2$ (50 mL) and mCPBA (77% max) (1.76 g) was added at rt. The reaction mixture was stirred overnight. The mixture was diluted with CH$_2$Cl$_2$ (80 mL) and washed with a sat. solution of NaHCO$_3$ (50 mL), water (50 mL) and brine (40 mL). The organic layer was dried (Na$_2$SO$_4$) and concentrated. The residue was purified by flash chromatography (silica gel, EtOAc) to afford compound 77 in 90% yield as a white solid. mp: 230-231° C. (lit.[3] 230-231° C.); $^1$H NMR (CDCl$_3$) δ 4.69 (s, 2H), 7.16 (d, 1H, J=8.7 Hz), 7.24 (d, 1H, J=2.1 Hz), 7.45 (m, 3H), 7.54 (dd, 1H, J=8.6, 2.2 Hz), 7.64 (dd, 2H, J=7.3, 3.6 Hz), 10.02 (s, 1H).

(7-Bromo-4-oxy-5-phenyl-3H-benzo[e][1,4]diazepin-2-yl)-methylamine 78.

Methylamine (50 mL, 2 M in THF) was added to 77 (1.9 g, 5.7 mmol) in a 100 mL round-bottom flask. The mixture was cooled to 0° C. after which TiCl$_4$ (0.54 g, 2.86 mmol) was added dropwise. The reaction mixture was allowed to warm to rt and stirred for 4 h. The mixture was quenched with water (5 mL), diluted with EtOAc (100 mL) and washed with dilute NH$_4$OH. The organic layer was washed with water, brine and dried (Na$_2$SO$_4$). After the solvent was removed under reduced pressure, the residue was purified by flash chromatography (silica gel, gradient elution, EtOAc, EtOAc:MeOH 10:1) to provide 78 in 86% yield as a white solid. mp: 236-237° C. (lit.[4] 242-243° C.); $^1$H NMR (300 MHz, CDCl$_3$) δ 0.21 (s, 9H), 2.91 (s, 3H), 4.17 (s, 1H), 4.85 (s, 1H), 7.13-7.66 (m, 9H).

(7-Trimethylsilylacetylenyl-4-oxy-5-phenyl-3H-benzo[e][1,4]diazepin-2-yl)-methyl-amine 79 (Hz146).

Trimethylsilylacetylenyl analog 79 (Hz146) was obtained in 58% yield from 78 analogous to the procedure employed in [0047] as a light gray solid. mp: 239-240° C.; IR (KBr) 3229, 3060, 2952, 2149, 1616, 1593, 1462, 1238, 868 cm$^{-1}$; $^1$H NMR (300 MHz, CDCl$_3$) δ 2.89 (d, 3H, J=4.4 Hz), 4.14 (d, 1H, J=10.6 Hz), 4.78 (d, 1H, J=10.4 Hz), 7.15 (d, 1H, J=1.7 Hz), 7.24-7.28 (m, 2H), 7.45 (m, 4H), 7.66 (m, 2H); MS (EI) m/e (relative intensity) 361 (M$^+$, 48), 344 (100), 303 (31), 165(33).

(7-Acetylenyl-4-oxy-5-phenyl-3H-benzo[e][1,4]diazepin-2-yl)-methyl-amine 80 (Hz147).

The 7-acetyleno target 80 was obtained in 90% yield from 79 analogous to the procedure employed in [0048] as a light yellow solid. mp: 213-214° C.; IR (KBr) 3242, 3068, 2977, 1619, 1589, 1460, 1414 cm$^{-1}$; $^1$H NMR (300 MHz, CDCl$_3$) δ 2.89 (d, 2H, J=3.7 Hz), 2.98 (s, 1H), 4.13 (bs, 1H), 4.78 (bs, 1H), 7.18-7.71 (m, 9H); MS (EI) m/e (relative intensity) 289 (M$^+$, 47), 272 (100), 231 (42).

(7-Bromo-5-phenyl-3H-benzo[e][1,4]diazepin-2-yl)-methyl-amine 81 (Hz135).

Bromide 81 was obtained in 70% yield from 1 analogous to the procedure employed in [0106] as a white solid. mp: 234-235° C.; IR (KBr) 3253, 3076, 1609, 1571, 1415, 1326, 1230 cm$^{-1}$; $^1$H NMR (300 MHz, CDCl$_3$) δ 2.62 (s, 3H), 3.56 (bs, 1H), 4.68 (bs, 1H), 6.34 (s, 1H), 7.17 (d, 1H, J=8.7 Hz), 7.36-7.81 (m, 7H); MS (EI) m/e (relative intensity) 329 (80), 328 (M$^+$, 100), 327 (82), 326 (92), 220 (38), 219(48), 218(46), 205 (38).

(7-Trimethylsilylacetylenyl-5-phenyl-3H-benzo[e][1,4]diazepin-2-yl)-methyl-amine 82 (Hz141).

Trimethylsilylacetylenyl analog 82 (Hz141) was obtained in 73% yield from 81 analogous to the procedure employed in [0047] as a light yellow solid. mp: 210-211° C.; IR (KBr) 3257, 3079, 2956, 2150, 1619, 1610, 1580, 1416, 1237, 880, 843 cm$^{-1}$; $^1$H NMR (300 MHz, CDCl$_3$) δ 0.22 (s, 9H), 2.59 (d, 3H, J=3.5 Hz), 3.56 (bs, 1H), 4.66 (bs, 1H), 6.39 (s, 1H), 7.21 (d, 1H, J=8.4 Hz), 7.39-7.65 (m, 7H); MS (EI) m/e (relative intensity) 345 (M$^+$, 100), 344 (98), 164(50).

(7-Acetylenyl-4-oxy-5-phenyl-3H-benzo[e][1,4]diazepin-2-yl)-methylamine 83 (Hz148).

The 7-acetyleno analog 83 (Hz148) was obtained in 92% yield from 82 analogous to the procedure employed in [0048] as a white solid. mp: 226-227° C.; IR (KBr) 3275, 3245, 3075, 2102, 1618, 1599, 1580, 1467, 1416, 1333, 1235 cm$^{-1}$; $^1$H NMR (300 MHz, CDCl$_3$) δ 2.65 (d, 3H, J=4.4 Hz), 2.97 (s, 1H), 3.57 (bs, 1H), 4.65 (bs, 1H), 6.20 (d, 1H, J=3.7 Hz), 7.22 (d, 1H, J=8.4 Hz), 7.42-7.58 (m, 7H). MS (EI) m/e (relative intensity) 273 (M$^+$, 100), 272 (98).

Scheme 17

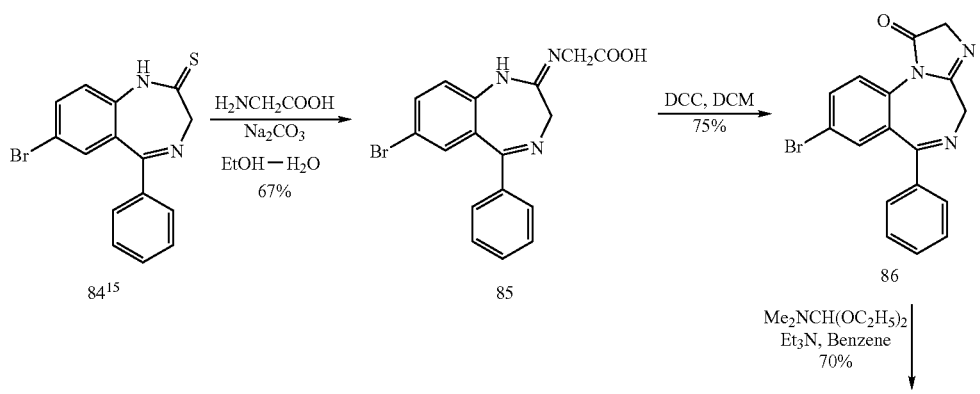

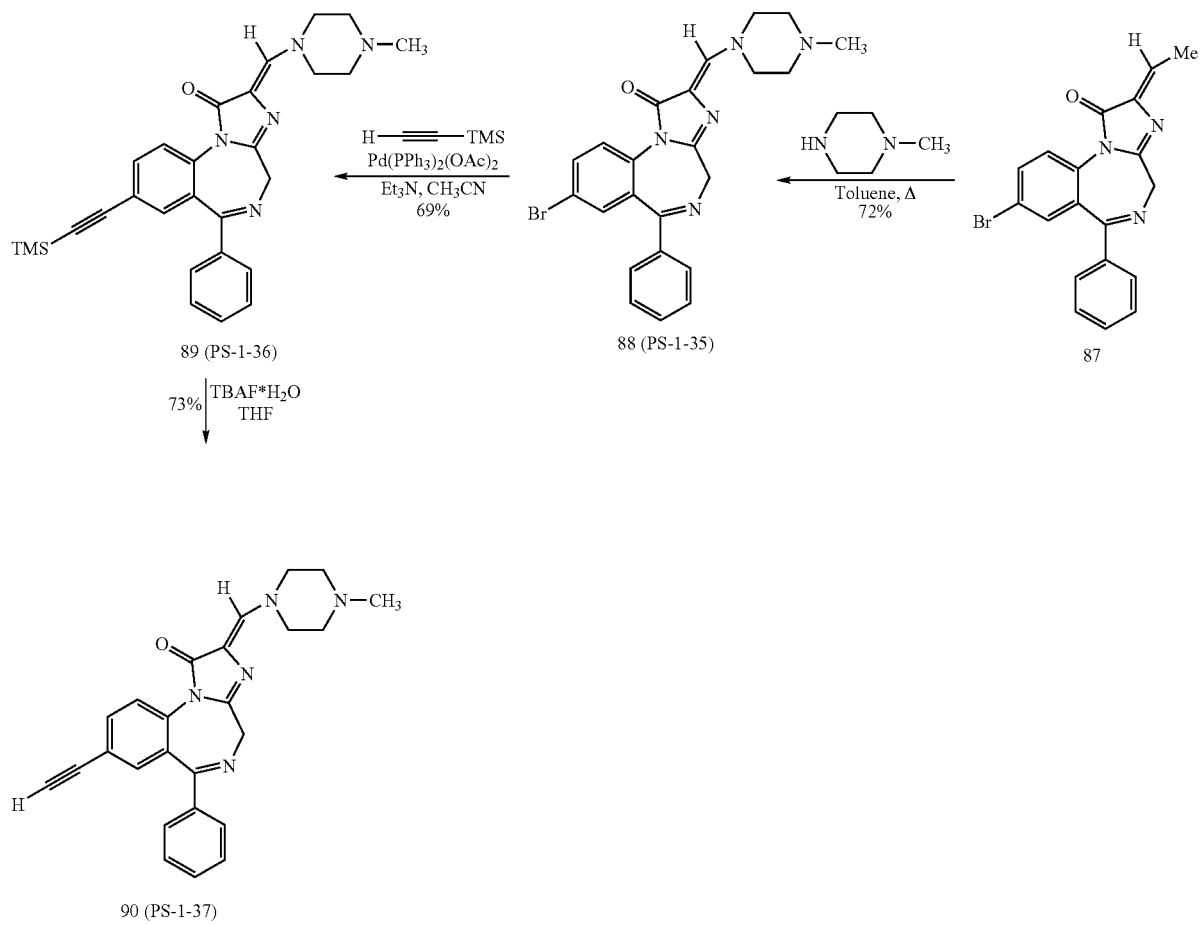

A suspension of 7-bromo-1,3-dihydro-5-phenyl-2H-1,4-benzodiazepin-2-thione 84[15] (1.6 g, 4.83 mmol), glycine (1.81 g, 24.2 mmol) and Na$_2$CO$_3$ (1.84 g, 17.4 mmol) in EtOH (38 mL)-H$_2$O (16 mL) was stirred at reflux for 5 h, poured into water (100 mL), and then filtered to remove a small amount of 7-bromo-1,3-dihydro-5-phenyl-2H-1,4-benzodiazepin-2-one which remained. The filtrate was extracted with CHCl$_3$. The CHCl$_3$ extract was discarded; the aqueous layer was adjusted to pH 4 with 2N HCl and then extracted with CHCl$_3$ (3×25 mL). Evaporation of the CHCl$_3$ solution gave pure acid 85 (1.2 g, 67%) as a yellow solid. Acid 85 (350 mg, 0.941 mmol) was suspended in dry CH$_2$Cl$_2$ (10 mL) and DCC (223 mg, 1.08 mmol) was added. The suspension which resulted was stirred at 40° C. for 2 h and then cooled to 0° C. It was filtered, and the solvent was removed in vacuum to give 8-bromo-2,4-dihydro-6-phenyl-1H-imidazo[1,2-a][1,4]benzodiazepin-1-one 3 as a brown oil. The cyclized product 86 (ca. 250 mg) was dissolved in dry benzene (6 mL), dimethylformamide diethylacetal (130 mg, 0.883 mmol) and triethylamine (89 mg, 0.883 mmol) were added. The solution which resulted was stirred at room temperature for 1 h and the solvent was removed in vacuum, The residue was then crystallized from EtOAc-MeOH to give 87 (200 mg, 70%). A solution of 87 (180 mg, 0.440 mmol) in dry toluene (5 mL) was treated with 1-methyl piperazine (1 mL) and heated to reflux for 5 h. The solvent was removed in vacuum to give a gum which crystallized from CH$_2$Cl$_2$-Et$_2$O to furnish 88 (PS-1-35, 146 mg, 72%). mp>250° C.; IR (KBr) 3324, 2932, 2787, 1692, 1624, 1475, 1402, 1297, 1137, 933 cm$^{-1}$; $^1$H NMR (CDCl$_3$) δ 7.95 (d, 1H, J=8.8 Hz), 7.72 (dd, 1H, J=2.3 Hz, J=8.8 Hz), 7.58-7.55 (m, 2H), 7.49-7.37 (m, 4H), 7.17 (s, 1H), 5.01 (d, 1H, J=12 Hz), 4.50-4.60 (m, 1H), 4.20-4.30 (m, 1H), 4.16 (d, 1H, J=12 Hz), 3.50-3.58 (m, 2H), 2.40-2.60 (m, 4H), 2.34 (s, 3H); MS (m/z) 465 (100).

To the suspension of compound 88 (PS-1-35, 140 mg, 0.302 mmol) in acetonitrile (4 mL) and triethylamine (3 mL) was added bis(triphenylphosphine)-palladium (II) acetate (22.6 mg, 0.03 mmol). The solution was degassed and trimethylsilylacetylene (0.1 mL, 0.7 mmol) was added. The mixture was heated to reflux and stirred overnight. After removal of the solvent in vacuum, the residue was dissolved in CH$_2$Cl$_2$ and washed with a saturated aqueous solution of NaHCO$_3$ and brine. The organic layer was dried (Na$_2$CO$_3$), filtered and concentrated under vacuum. The residue was purified by flash column chromatography (EtOAc:MeOH 9:1) to furnish the trimethylsilyl analogue 89 (PS-1-36, 100 mg, 69%) as a pale yellow solid. mp>250° C.; IR (KBr) 3436, 2936, 2794, 2154, 1682, 1625, 1489, 1136, 847 cm$^{-1}$; $^1$H NMR (CDCl$_3$) δ 8.0 (d, 1H, J=8.5 Hz), 7.68 (dd, 1H, J=1.9 Hz, J=8.5 Hz), 7.55-7.59 (m, 2H), 7.37-7.49 (m, 4H), 7.16 (s, 1H), 4.99 (d, 1H, J=12 Hz), 4.50-4.60 (m, 1H), 4.20-4.30 (m, 1H), 4.13 (d, 1H, J=12.4 Hz), 3.48-3.58 (m, 2H), 2.4-2.6 (m, 4H), 2.35 (s, 3H), 0.23 (s, 9H); MS (m/z) 482 (100).

A solution of the trimethylsilyl analog 89 (PS-1-36, 65 mg, 0.135 mmol) in THF (15 mL) was stirred with tetrabutylammonium fluoride hydrate (45 mg, 0.175 mmol) at −5° C. for 5 min. After this, H$_2$O (5 mL) was added to the solution to quench the reaction and stirring continued at low temperature for one half hour. The solution was extracted with EtOAc (3×40 mL), and the organic layer was washed with water. After removal of the solvent under reduced pressure, ethyl ether was added to the residue to precipitate a solid. The mixture was filtered and the solid was washed with CHCl$_3$-Et$_2$O (ca 1:15) to provide the acetyl target 90 (PS-1-37, 40 mg, 73%). mp 223-224° C.; IR (KBr) 3298, 2935, 2786, 1695, 1628, 1364, 1136, 1002, 778 cm$^{-1}$; $^1$H NMR (CDCl$_3$) δ 8.04 (d, 1H, J=8.5 Hz), 7.71 (dd, 1H, J=1.9 Hz, J=8.5 Hz), 7.55-7.58 (m, 2H), 7.36-7.48 (m, 4H), 7.17 (s, 1H), 5.0 (d, 1H, J=12.1 Hz), 4.5-4.6 (m, 1H), 4.2-4.3 (m, 1H), 4.16 (d, 1H, J=12.1 Hz), 3.5-3.6 (m, 2H), 3.08 (s, 1H), 2.4-2.6 (m, 4H), 2.35 (s, 3H); MS (m/z) (100).

Scheme 18

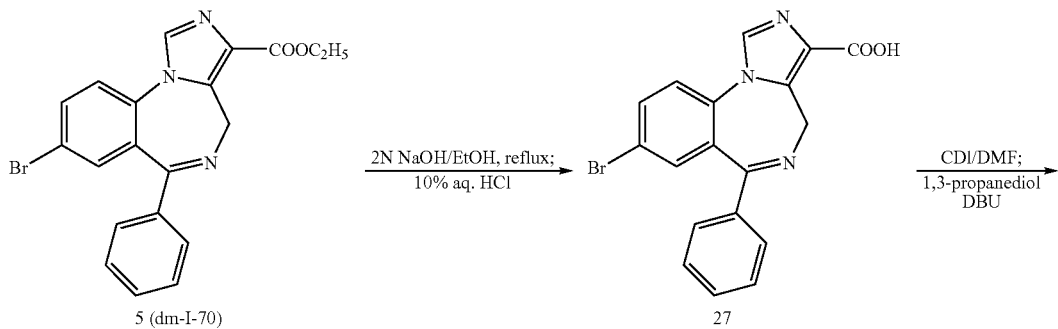

5 (dm-I-70)

27

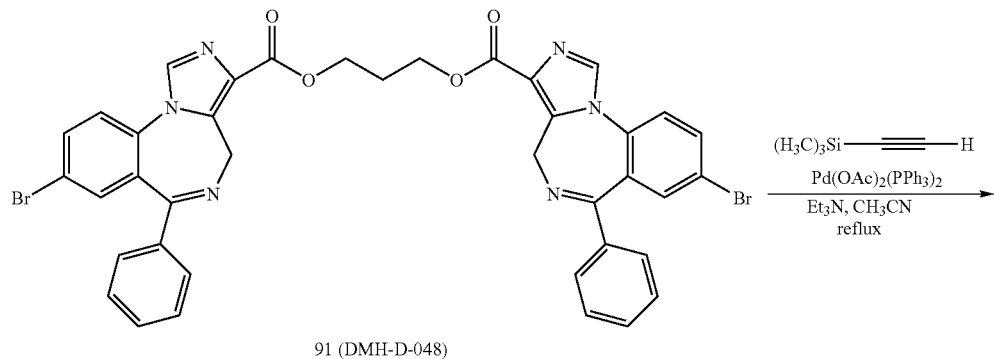

91 (DMH-D-048)

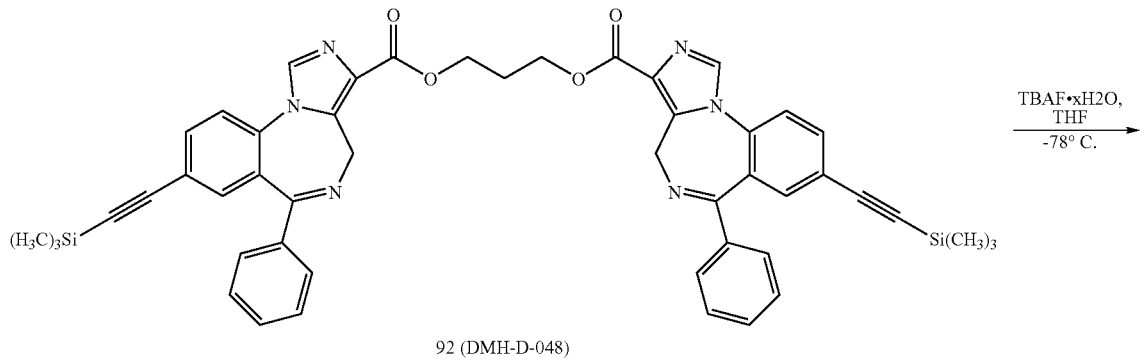

92 (DMH-D-048)

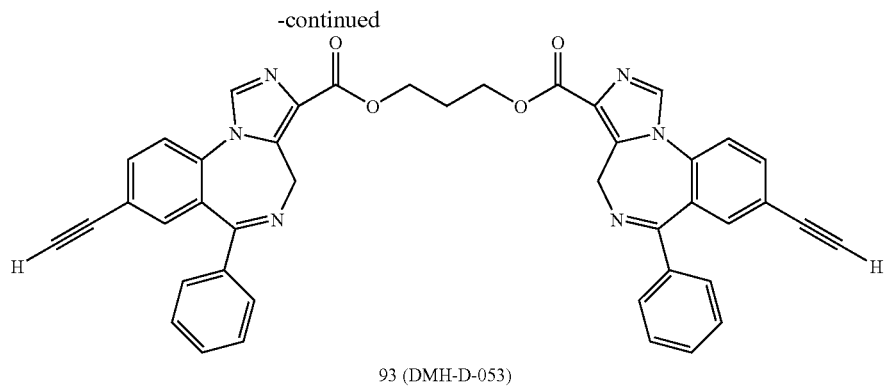

93 (DMH-D-053)

The acid 27, obtained from the ester 5 (dm-1-70), was stirred with CDI in DMF, followed by stirring with 1,3-propanediol and DBU to provide 91 (DMH-D-070, the dimer of dm-1-70). This was converted into the trimethylsilylacetylenyl compound 92 (DMH-D-048, the dimer of XLiXHe048) under standard conditions (Pd-mediated, Heck-type coupling).[4,7,8] The bisacetylene 93 (DMH-D-053, the dimer of XHeII-053) was easily obtained by treatment of trimethylsilyl compound 92 with fluoride anion as shown in Scheme 18.[7]

8-Bromo-6-phenyl-4H-benzo[f]imidazo[1,5-a][1,4]diazepine-3-carboxylic acid 27.

The ester 5 (2 g) was dissolved in EtOH (50 mL) and aq sodium hydroxide (10 mL, 2N) was added to the solution. The mixture was heated to reflux for half an hour. After the EtOH was removed under reduced pressure, the solution was allowed to cool. The pH value was adjusted to 4 by adding 10% aq HCl dropwise. The mixture was filtered and the solid was washed with water and ethyl ether. The solid was dried to provide 27 (1.8 g, 96.6%): mp>250° C.; IR (KBr) 3450 (b), 2844, 1707, 1615, 1493, 1166, 700 cm$^{-1}$; $^1$H NMR (300 MHz, DMSO-d$_6$) δ 4.14 (d, 1H, J=12.6 Hz), 5.79 (d, 1H, 12.6 Hz), 7.41-7.54 (m, 6H), 7.88 (d, 1H, J=8.7 Hz), 8.03 (dd, 1H, J=8.7 Hz, J=2.1 Hz), 8.47 (s, 1H); MS (EI) m/e (rel intensity) 381 (M$^+$, 20), 383 (19).

1,3-Bis(8-bromo-6-phenyl-4H-benzo[f]imidazo[1,5-a][1,4]diazepine-3-carb-oxy)propyl diester 91 (DMH-D-070).

The carboxylic acid 27 (2 g, 5.2 mmol) was dissolved in DMF (20 mL), after which CDI (1.02 g, 6.3 mmol) was added at rt and the mixture was stirred for 2 h. Then 1,3-propanediol (0.19 mL, 2.6 mmol) and DBU (0.78 mL, 5.2 mmol) were added to the mixture and stirring continued overnight. The reaction solution was then cooled with an ice-water bath, after which water was added to precipitate a solid. This material was purified further by flash chromatography on silica gel (gradient elution, EtOAc:EtOH 20:1, 15:1, 10:1) to provide the bisbromide 91 (DMH-D-070) as a white solid (1.3 g, 61.9%): mp 187.5-189° C.; IR (KBr) 3112, 2968, 1708, 1610, 1559, 1491, 1269, 1160, 1123, 1073 cm$^{-1}$; $^1$H NMR (300 MHz, CDCl$_3$) δ 2.35 (m, 2H), 4.08 (d, 2H, J=12.6 Hz), 4.55 (m, 4H), 6.05 (d, 2H, J=12.6 Hz), 7.37-7.53 (m, 12H), 7.6 (d, 2H, J=2.1 Hz), 7.81 (dd, 2H, J=2.1 Hz, 8.6 Hz), 7.93 (s, 2H); $^{13}$C NMR (75.5 MHz, CDCl$_3$) δ 28.2, 44.9, 61.4, 120.7, 124.2, 128.3, 129.0, 129.3, 129.6, 130.6, 134.1, 134.4, 134.7, 135.0, 138.9, 138.9, 162.6, 167.9; MS (FAB, NBA) m/e (rel intensity) 803 (M$^+$+1, 15); Anal. Calcd. For C$_{39}$H$_{28}$N$_6$O$_4$Br$_2$: C, 58.23; H, 3.51; N, 10.45. Found: C, 57.92; H, 3.43; N, 10.29.

1,3-Bis(8-trimethylsilylacetylenyl-6-phenyl-4H-benzo[f]imidazo[1,5-a][1,4]-diazepine-3-carboxy)propyl diester 92 (DMH-D-048)[4,7,8]

To a suspension of bisbromide 91 (1.005 g, 1.25 mmol) in acetonitrile (50 mL) and triethylamine (65 mL), was added bis(triphenylphosphine)-palladium (II) acetate (0.15 g, 0.2 mmol). The solution was degassed and trimethylsilylacetylene (0.7 mL, 5 mmol) was added after which it was degassed again. The mixture was heated to reflux and stirring maintained overnight. After removal of the solvent under reduced pressure, the residue was dissolved in CH$_2$Cl$_2$ and washed with water. 3-Mecaptopropyl functionalized silica gel (0.6 g) was added into the organic layer and stirring continued for 1 hour. The silica gel/Pd complex was removed by filtration and the filtrate was concentrated under reduced pressure. The residue was purified by flash column chromatography on silica gel (gradient elution, EtOAc:EtOH 20:1, 15:1, 10:1) to furnish the bistrimethylsilyl dimer 92 (DMH-D-048, 680 mg, 60.8%) as a white solid: mp 169-172° C.; IR (KBr) 3449, 2950, 1725, 1720, 1715, 1496, 1250, 1160, 1080, 847 cm$^{-1}$; $^1$H NMR (300 MHz, CDCl$_3$) δ 0.25 (s, 18H), 2.35 (m, 2H), 4.05 (d, 2H, J=12.6 Hz), 4.55 (m, 4H), 6.02 (d, 2H, J=12.6 Hz), 7.37-7.55 (m, 14H), 7.75 (dd, 2H, J=1.8 Hz, 8.4 Hz), 7.94 (s, 2H); $^{13}$C NMR (75.5 MHz, CDCl$_3$) δ -0.3, 28.3, 44.9, 61.4, 97.4, 102.3, 122.4, 122.6, 128.0, 128.3, 129.0, 129.4, 130.5, 134.1, 134.9, 135.1, 139.0, 139.2, 139.2, 162.6, 168.5; MS (FAB, NBA) m/e (rel intensity) 839 (M$^+$+1, 100); Anal. Calcd. For C$_{49}$H$_{46}$N$_6$O$_4$Si$_2$: C, 70.14; H, 5.53; N, 10.02. Found: C, 69.97; H, 5.35; N, 9.77.

1,3-Bis(8-acetylenyl-6-phenyl-4H-benzo[f]imidazo[1,5-a][1,4]diazepine-3-carboxy)propyl diester 93 (DMH-D-053)[7]

A solution of bistrimethylsilyl dimer 92 (330 mg, 0.4 mmol) in THF (70 mL) was stirred with tetrabutylammonium fluoride hydrate (250 mg, 0.96 mmol) at −78° C. for 5 min. After this, H$_2$O (35 mL) was added to the solution to quench the reaction and stirring continued at low temperature for one half hour. The solution was extracted with EtOAc (3×100 mL), and the organic layer was washed with water. After removal of the solvent under reduced pressure, ethyl ether was added to the residue to precipitate a solid. The mixture was filtered and the solid was washed with CHCl$_3$-Et$_2$O (ca 1:15), the bisacetylenyl dimer 93 (DMH-D-053, 220 mg, 80%) was obtained as a yellow solid: mp 172-175° C.; IR (KBr) 3450, 3280, 2950, 1720, 1715, 1495, 1250, 1120, 1050 cm$^{-1}$; $^1$H NMR (300 MHz, CDCl$_3$) δ 2.35 (m, 2H), 3.18 (s, 2H), 4.08 (d, 2H, J=12.3 Hz), 4.56 (m, 4H), 6.04 (d, 2H, J=12.6 Hz), 7.36-7.59 (m, 14H), 7.78 (dd, 2H, J=8.4 Hz, 1.7 Hz), 7.95 (s, 2H); $^{13}$C NMR (75.5 MHz, CDCl$_3$) δ 28.8, 45.4, 61.9, 80.2, 81.3, 121.4, 122.7, 128.1, 128.3, 129.0, 129.3, 130.5, 134.2, 135.2, 135.3, 135.6, 138.9, 139.2, 162.6, 168.5; MS (FAB, NBA) m/e (rel intensity) 695 (M$^+$+1, 100).

and 93 (DMH-D-053), respectively, by using 1,5-pentanediol in place of 1,3-propanediol (Scheme 19).

1,5-Bis(8-bromo-6-phenyl-4H-benzo[f]imidazo[1,5-a][1,4]diazepine-3-carb-oxy)pentyl diester 94 (dm-II-26)

A yellow powder (63.2%): mp 172-175° C.; IR (KBr) 3112, 2970, 1721, 1609, 1490, 1267, 1158, 1075, 754, 697 cm$^{-1}$; $^1$H NMR (300 MHz, CDCl$_3$) δ 1.62 (m, 2H), 1.90 (m, 4H), 4.07 (d, 2H, J=12.6 Hz), 4.39 (m, 4H), 6.05 (d, 2H, J=12.6 Hz), 7.37-7.53 (m, 12H), 7.58 (d, 2H, J=2.1 Hz), 7.78 (dd, 2H, J=2.1 Hz, 8.6 Hz), 7.92 (s, 2H); $^{13}$C NMR (75.5

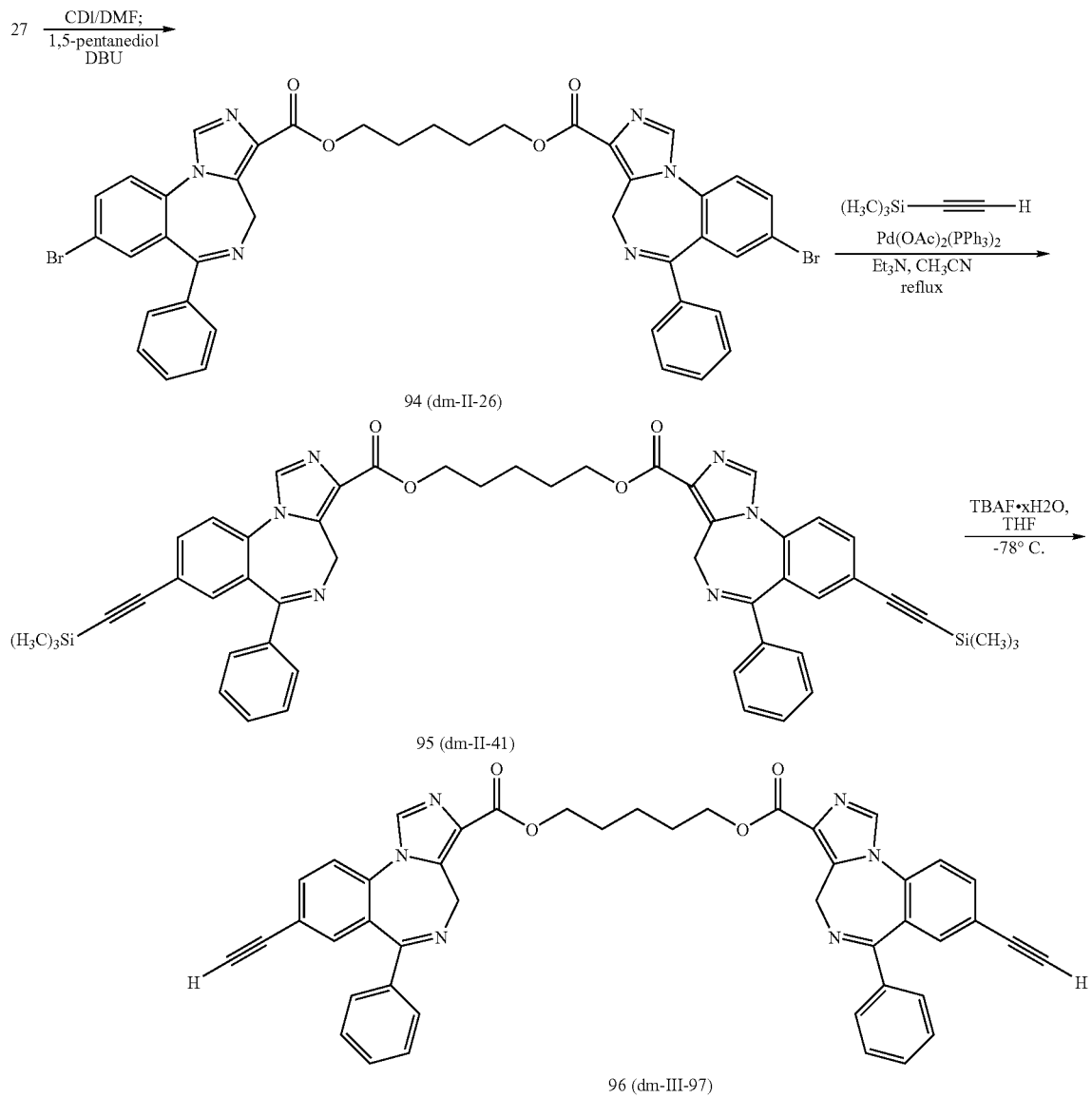

MHz, CDCl$_3$) δ 22.5, 28.4, 44.9, 64.5, 120.7, 124.2, 128.3, 129.2, 129.3, 129.6, 130.6, 134.0, 134.5, 134.6, 135.0, 138.8, 138.9, 162.8, 167.9; MS (FAB, NBA) m/e (rel intensity) 831 (M$^+$+1, 5). Anal. Calcd. For C$_{41}$H$_{32}$N$_6$O$_4$Br$_2$·0.25H$_2$O: C, 58.95; H, 3.89; N, 10.07. Found: C, 58.69; H, 3.74; N, 9.70.

The 5-carbon linker bisbromide 94 (dm-II-26), bis-trimethylsilylacetylenyl dimer 95 (dm-II-41) and bisacetylene dimer 96 (dm-II-97), which are analogues of dimers DMH-D-070, DMH-D-048 and DMH-D-053, respectively, were prepared from acid 27 under the same conditions employed for preparing dimers 91 (DMH-D-070), 92 (DMH-D-048)

1,5-Bis(8-trimethylsilylacetylenyl-6-phenyl-4H-benzo[f]imidazo[1,5-a][1,4]-diazepine-3-carboxy) pentyl diester 95 (dm-II-41)

A yellow solid (58.1%): mp 154-156° C.; IR (KBr) 3426, 2955, 1727, 1720, 1612, 1495, 1251, 1174, 1076, 846 cm$^{-1}$; $^1$H NMR (300 MHz, CDCl$_3$) δ 0.25 (s, 18H), 1.63(m, 2H), 1.90 (m, 4H), 4.05 (d, 2H, J=12.6 Hz), 4.39 (m, 4H), 6.03 (d, 2H, J=12.6 Hz), 7.40-7.54 (m, 14H), 7.75 (dd, 2H, J=1.8 Hz, 8.4 Hz), 7.93 (s, 2H); $^{13}$C NMR (75.5 MHz, CDCl$_3$) δ −0.3, 22.5, 28.4, 44.9, 64.5, 97.4, 102.3, 122.4, 122.6, 128.0, 128.3, 129.2, 129.4, 130.5, 134.1, 135.0, 135.1, 135.1, 138.9, 139.3, 162.8, 168.5; MS (FAB, NBA) m/e (rel intensity) 867 (M$^+$+1, 100).

1,5-Bis(8-acetylenyl-6-phenyl-4H-benzo[f]imidazo[1,5-a][1,4]diazepine-3-carboxy) pentyl diester 96 (dm-III-97).

A yellow solid: mp 150-153° C.; IR (KBr) 3290, 2953, 1718, 1611, 1493, 1253, 1172, 1120, 1076 cm$^{-1}$; $^1$H NMR (300 MHz, CDCl$_3$) δ 1.62 (m, 2H), 1.90 (m, 4H), 3.18 (s, 2H), 4.07 (d, 2H, J=12.3 Hz), 4.38 (m, 4H), 6.04 (d, 2H, J=12.3 Hz), 7.36-7.58 (m, 14H), 7.77 (dd, 2H, J=8.4 Hz, 1.6 Hz), 7.94 (s, 2H); $^{13}$C NMR (75.5 MHz, CDCl$_3$) δ 22.5, 28.4, 44.9, 64.5, 79.8, 81.3, 121.3, 122.7, 128.1, 128.3, 129.2, 129.3, 130.5, 134.1, 135.2, 135.3, 135.6, 138.8, 139.2, 162.8, 168.5; MS (FAB, NBA) m/e (rel intensity) 723 (M$^+$+1, 13).

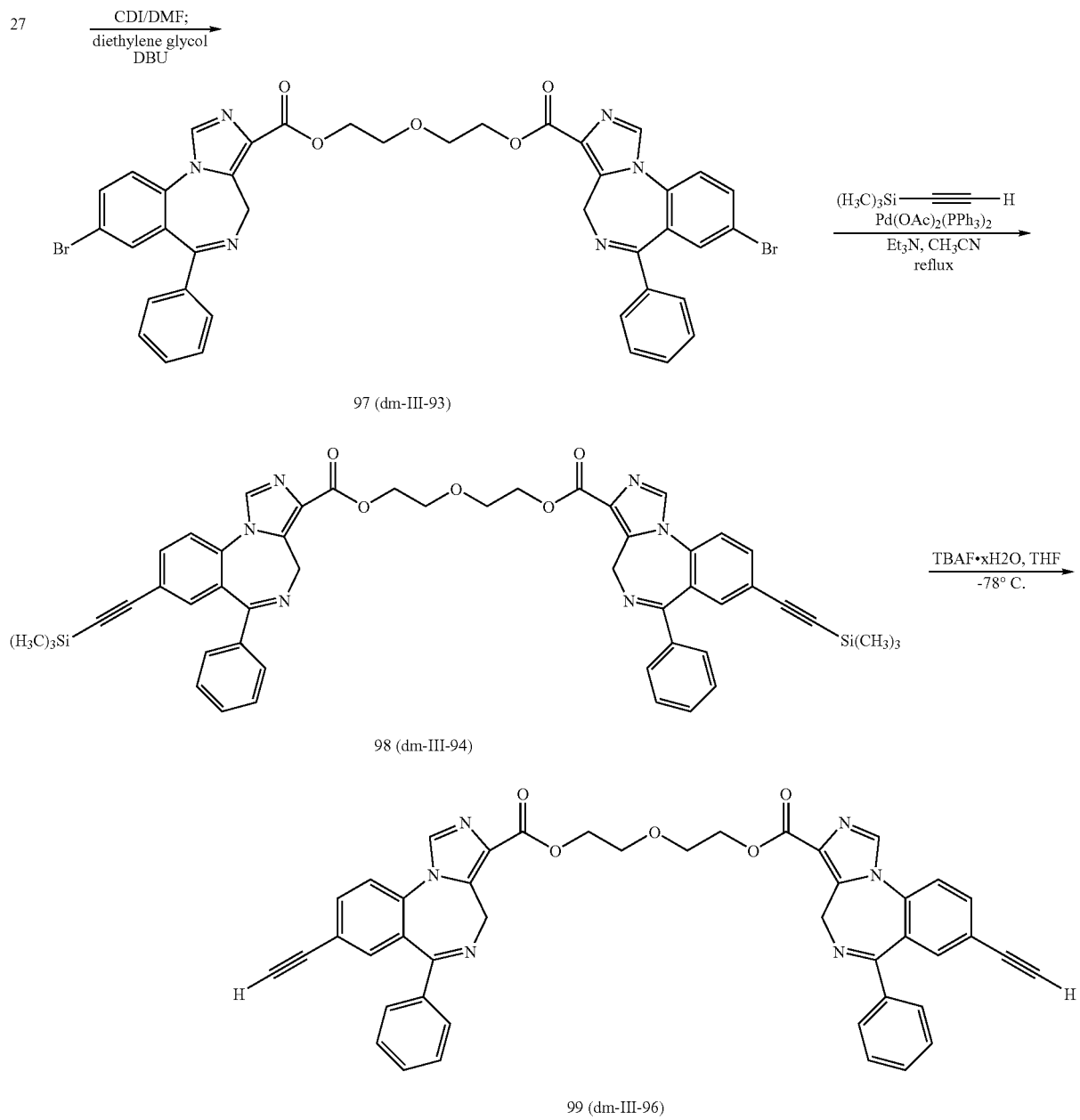

Scheme 20

In order to improve the water solubility of the dimers, the oxygen-containing 5-atom linked dimers 97 (dm-III-93), 98 (dm-II-94) and 99 (dm-III-96), were designed and prepared from acid 27 under the same conditions employed for preparation of dimers DMH-D-070, DMH-D-048 and DMH-D-053, respectively, by replacing 1,3-propanediol with diethylene glycol (Scheme 20).

Bis(8-bromo-6-phenyl-4H-benzo[f]imidazo[1,5-a][1,4]diazepine-3-carboxy)diethylene glycol diester 97 (dm-III-93)

A yellow solid (93.7%): mp 165-168° C.; IR (KBr) 3060, 2956, 1725, 1610, 1558, 1491, 1267, 1161, 1123, 1074 cm$^{-1}$; $^1$H NMR (300 MHz, CDCl$_3$) δ 3.93 (t, 4H, J=4.8 Hz), 4.06 (d, 2H, J=12.6 Hz), 4.54 (m, 4H), 6.05 (d, 2H, J=12.6 Hz), 7.39-7.50 (m, 12H), 7.57 (d, 2H, J=2.7 Hz), 7.80 (dd, 2H, J=2.1 Hz, 8.4 Hz), 7.90 (s, 2H); $^{13}$C NMR (75.5 MHz, CDCl$_3$) δ 44.9, 63.6, 69.0, 120.7, 124.2, 128.3, 129.0, 129.3, 129.6, 130.6, 134.1, 134.4, 134.6, 135.0, 138.9, 139.0, 162.5, 167.9; MS (FAB, NBA) m/e (rel intensity) 833 (M$^+$+1, 5).

Bis(8-trimethylsilylacetylenyl-6-phenyl-4H-benzo[f]imidazo[1,5-a][1,4]diazepine-3-carboxy)diethylene glycol diester 98 (dm-III-94)

A yellow solid (49.5%): mp 205-208° C.; IR (KBr) 3433, 2960, 1730, 1700, 1612, 1493, 1255, 1169, 1120, 1071, 847 cm$^{-1}$; $^1$HNMR (300 MHz, CDCl$_3$) δ 0.25 (s, 18H), 3.93 (t, 4H, J=5.4 Hz), 4.04 (d, 2H, J=12.6 Hz), 4.55 (m, 4H), 6.04 (d, 2H, J=12.6 Hz), 7.37-7.53 (m, 14H), 7.74 (dd, 2H, J=1.2 Hz, 8.4 Hz), 7.91 (s, 2H); $^{13}$C NMR (75.5 MHz, CDCl$_3$) δ −0.3, 45.0, 63.6, 69.0, 97.5, 102.4, 122.5, 122.7, 128.1, 128.3, 129.0, 129.4, 130.5, 134.2, 135.0, 135.1, 135.2, 139.1, 139.3, 162.7, 168.6; MS (FAB, NBA) m/e (rel intensity) 869 (M$^+$+1, 100).

Bis(8-acetylenyl-6-phenyl-4H-benzo[f]imidazo[1,5-a][1,4]diazepine-3-carb-oxy)diethylene glycol diester 98 (dm-III-96)

A yellow solid (81.6%): mp 173-177° C.; IR (KBr) 3432, 3280, 1720, 1715, 1496, 1254, 1175, 1120, 1074 cm$^{-1}$; $^1$H NMR (300 MHz, CDCl$_3$) δ 3.12 (s, 2H), 3.93 (t, 4H, J=4.5 Hz), 4.06 (d, 2H, J=12.6 Hz), 4.55 (m, 4H), 6.05 (d, 2H, J=12.6 Hz), 7.38-7.56 (m, 14H), 7.75 (dd, 2H, J=8.4 Hz, 1.8 Hz), 7.91 (s, 2H); $^{13}$C NMR (75.5 MHz, CDCl$_3$) δ 45.0, 63.6, 69.0, 79.8, 81.3, 121.3, 122.7, 128.1, 128.3, 129.0, 129.3, 130.5, 134.2, 135.2, 135.3, 135.6, 139.0, 139.1, 162.6, 168.4; MS (FAB, NBA) m/e (rel intensity) 725 (M$^+$+1, 63).

Scheme 21

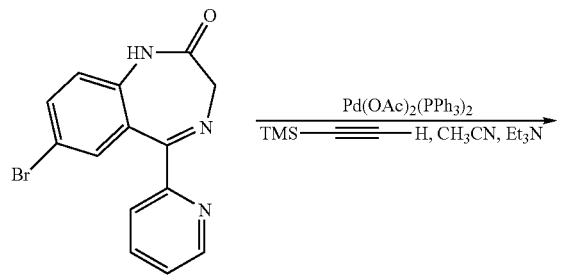

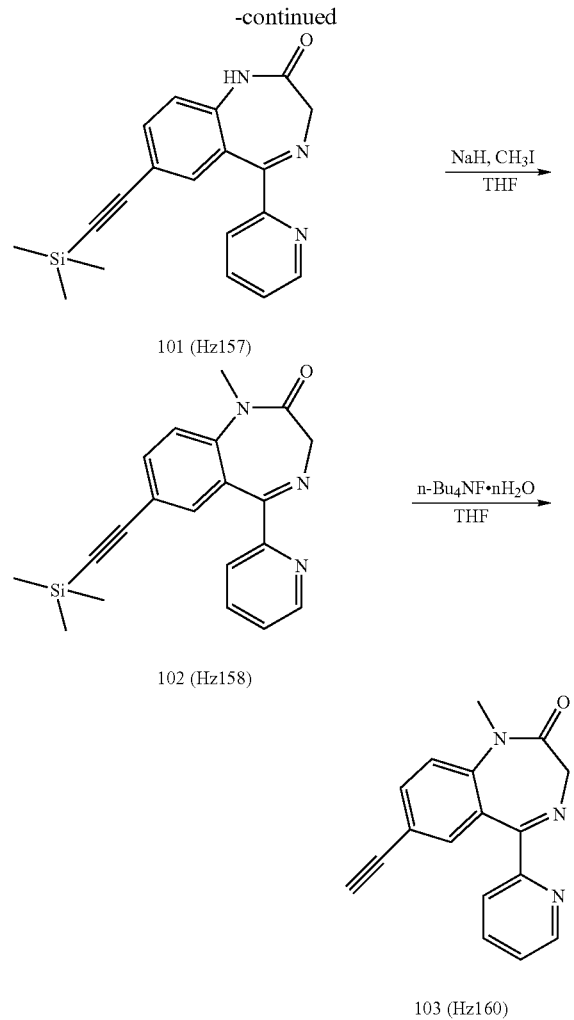

The benzodiazepine 100 (bromazepam)[16,17] was reacted with trimethylsilyacetylene in the presence of a palladium catalyst to provide trimethylsilyl analog 101 (Hz157) that was methylated with methyl iodide/sodium hydride to afford analog 102 (Hz158). This was subjected to fluoride-mediated desilation to achieve analog 103 (Hz160).

7-Trimethylsilylacetylenyl-5-pyridin-2-yl-1,3-dihydro-benzo[e][1,4]diazepin-2-one (Hz157).

Trimethylsilylacetylenyl analog 101 (Hz157) was obtained in 76% yield from 100 analogously to the procedure employed in [0047] as a light gray solid. mp: 242-243° C.; IR (KBr) 2956, 2155, 1690, 1616, 1492, 1332, 1248, 1018, 842, 754 cm$^{-1}$; $^1$H NMR (300 MHz, CDCl$_3$) δ 0.23 (s, 9H), 4.39 (s, 2H), 7.06 (d, 1H, J=8.4 Hz), 7.41 (ddd, 1H, J=7.5, 4.8, 1.2 Hz), 7.46 (d, 1H, J=1.8 Hz), 7.57 (dd, 1H, J=8.4, 1.9 Hz), 7.83 (td, 1H, J=7.7, 1.7 Hz), 7.97 (d, 1H, J=7.9 Hz), 8.41 (bs, 1H), 8.68 (d, 1H, J=4.2 Hz); MS (EI) m/e (relative intensity) 334 (35), 333 (M$^+$, 100), 332 (57), 318 (21), 304 (31).

7-Trimethylsilylacetylenyl-1-methyl-5-pyridin-2-yl-1,3-dihydro-benzo[e][1,4]diazepin-2-one (Hz158).

Trimethylsilyacetylenyl analog 102 (Hz158) was obtained in 74% yield from 101 analogously to the procedure employed in [0048] as a light grey solid. mp: 194-195° C.; IR (KBr) 2956, 2154, 1682, 1614, 1491, 1335, 1249, 881, 844, 747 cm$^{-1}$; $^1$H NMR (300 MHz, CDCl$_3$) δ 0.24 (s, 9H), 3.42 (s, 3H), 3.84 (d, 1H, J=10.6 Hz), 4.89 (d, 1H, J=10.6 Hz), 7.29 (d, 1H, J=7.6 Hz), 7.40 (m, 1H), 7.46 (d, 1H, J=1.9 Hz), 7.63 (dd, 1H, J=8.5, 1.9 Hz), 7.84 (td, 1H, J=7.7, 1.7 Hz), 8.09 (d, 1H, J=7.9 Hz), 8.68 (d, 1H, J=4.3 Hz); MS (EI) m/e (relative intensity) 348 (28), 347 (M$^+$, 100), 346 (44), 318 (34), 291 (23).

7-Acetylenyl-1-methyl-5-pyridin-2-yl-1,3-dihydro-benzo[e][1,4]diazepin-2-one (Hz160).

The 7-acetyleno analog 103 (Hz160) was obtained in 63% yield from 102 analogous to the procedure employed in [0048] as a white solid. mp: 190-191° C.; IR (KBr) 3286, 3233, 1678, 1614, 1491, 1344, 1126, 750 cm$^{-1}$; $^1$HNMR (300 MHz, CDCl$_3$) δ 3.07 (s, 1H), 3.86 (d, 1H, J=10.6 Hz), 4.93 (d, 1H, J=10.2 Hz), 7.32 (d, 1H, J=8.6 Hz), 7.39 (m, 1H), 7.51 (d, 1H, J=1.8 Hz), 7.65 (dd, 1H, J=8.5, 1.9 Hz), 7.83 (td, 1H, J=7.7, 1.7 Hz), 8.11 (d, 1H, J=7.9 Hz), 8.65 (d, 1H, J=4.7 Hz); MS (EI) m/e (relative intensity) 275 (M$^+$, 100), 274 (35), 246 (43), 219 (30).

Scheme 22

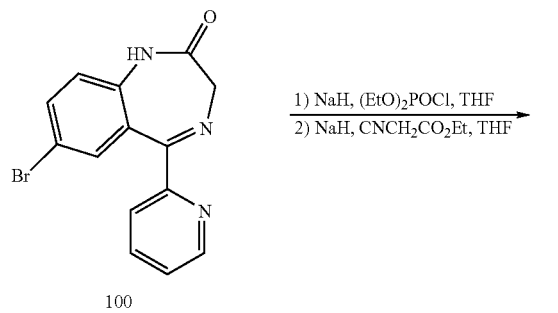

100

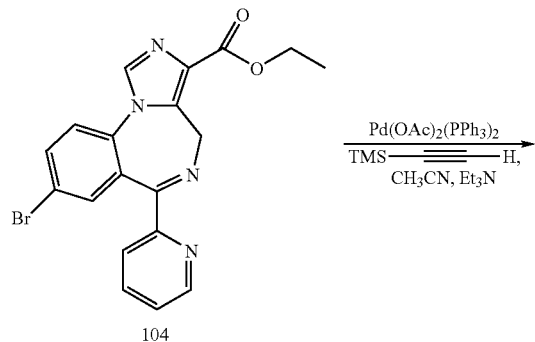

104

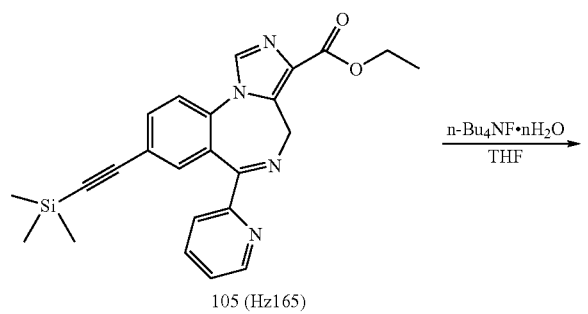

105 (Hz165)

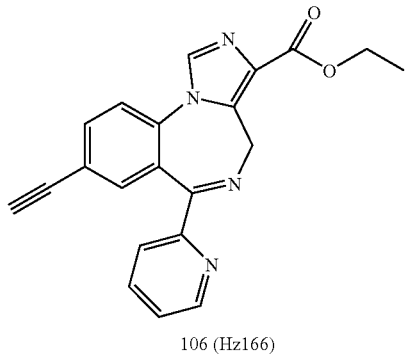

106 (Hz166)

The benzodiazepine 100 (bromazepam) was reacted with diethylphosphorochloridate, followed by the addition of ethyl isocyanoacetate to provide the ester 104. This was then reacted with trimethylsilyacetylene in the presence of a palladium catalyst to provide trimethylsilyl analog 105 (Hz165) which was subjected to fluoride-mediated desilylation to furnish analog 106 (Hz166).

8-Trimethylsilylacetylenyl-6-pyridin-2-yl-4H-benzo[f]imidazo[1,5-a][1,4]diazepine-3-carboxylic acid ethyl ester 105 (Hz165)

Trimethylsilyacetylenyl analog 105 (Hz165) was obtained in 73% yield from 104 analogous to the procedure employed in [0047] as a white solid. mp: 205-206° C.; $^1$H NMR (300 MHz, CDCl$_3$) δ 0.25 (s, 9H), 1.44 (t, 3H, J=7.1 Hz), 4.14 (d, 1H, J=11.0 Hz), 4.44 (m, 2H), 6.11 (d, 1H, J=10.9 Hz), 7.38 (ddd, 1H, J=7.5, 4.8, 1.1 Hz), 7.51 (s, 1H), 7.54 (d, 1H, J=8.4 Hz), 7.74 (dd, J=8.3, 1.8 Hz), 7.83 (td, 1H, J=7.7, 1.7 Hz), 7.93 (s, 1H), 8.05 (m, 1H), 8.61 (m, 1H).

8-Acetylenyl-6-pyridin-2-yl-4H-benzo[f]imidazo[1,5-a][1,4]diazepine-3-carboxylic acid ethyl ester 106 (Hz166).

The 7-acetyleno analog 106 (Hz166) was obtained in 98% yield from 105 analogous to the procedure employed in [0048] as a white solid. mp: 243-244° C.; $^1$H NMR (300 MHz, CDCl$_3$) δ 1.45 (t, 3H, J=7.1 Hz), 3.17 (s, 1H), 4.17 (d, 1H, J=10.0 Hz), 4.45 (m, 2H), 6.13 (d, 1H, J=10.4 Hz), 7.38 (ddd, 1H, J=7.5, 4.8, 1.1 Hz), 7.56 (d, 1H, J=8.2 Hz), 7.58 (s, 1H), 7.77 (dd, 1H, J=8.6, 1.8 Hz), 7.83 (td, 1H, J=7.7, 1.8 Hz), 7.93 (s, 1H), 8.08 (m, 1H), 8.59 (m, 1H).

Some exemplary compounds falling under the scope of the present invention are as follows:

In general, any 1,4-benzodiazepine with a 5-phenyl-like substituent in which C(7) has been replaced with an acetylene substituent or a trimethylsilyl acetylene substituent or any triazolo benzodiazepine that has a corresponding substituent at C(8) with a 6-phenyl group (alprazolam numbering system). For example, we claim any benzodiazepine structurally related to analogs (and other related compounds) to diazepam, alprazolam, medazolam, and triazolam in which the C(7) or C(8) substituent has been replaced with an acetylene or trimethylsilylacetylene substituent.

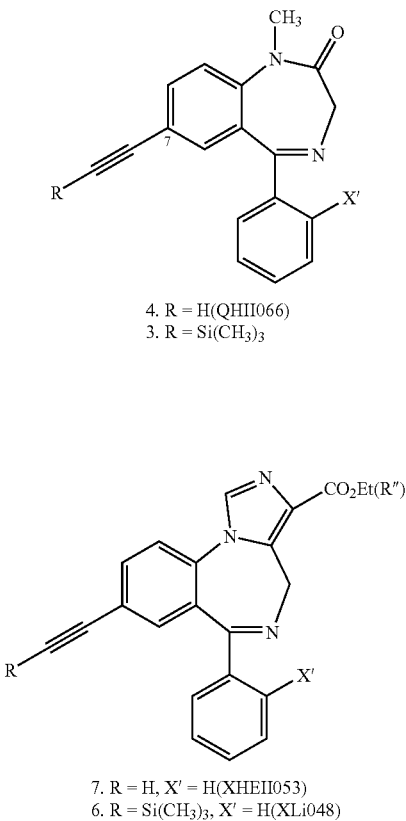

4. R = H(QHII066)
3. R = Si(CH₃)₃

7. R = H, X' = H(XHEII053)
6. R = Si(CH₃)₃, X' = H(XLi048)

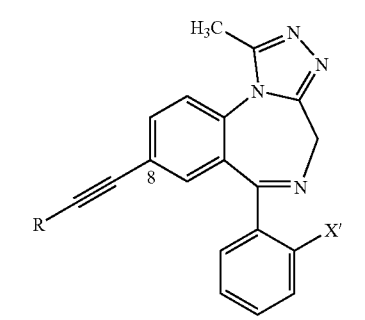

10. R = H, X' = H(XLi-270)
9. R = Si(CH₃)₃, X' = H(XLi269)
18. R = H, X' = F(JYI-70)
17. R = Si(CH₃)₃, X' = F(JYI-72)
23. R-H, X' = Cl(XLi-JY-DMH-TMS)
22. R = Si(CH₃)₃, X' = Cl(XLi-JY-DMH)

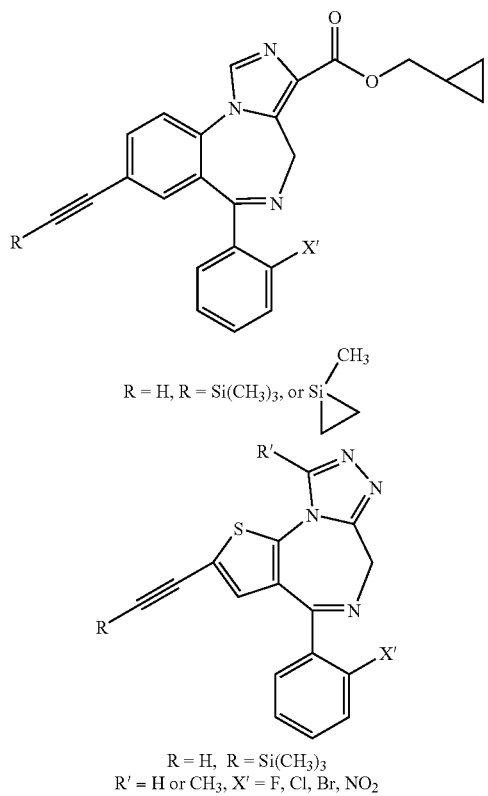

R = H, R = Si(CH₃)₃, or Si(CH₃)(cyclopropyl)

R = H, R = Si(CH₃)₃
R' = H or CH₃, X' = F, Cl, Br, NO₂

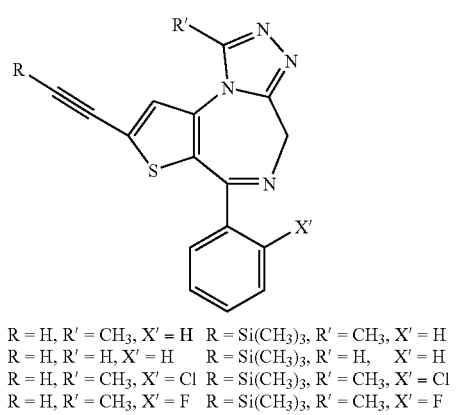

R = H, R' = CH₃, X' = H    R = Si(CH₃)₃, R' = CH₃, X' = H
R = H, R' = H, X' = H       R = Si(CH₃)₃, R' = H, X' = H
R = H, R' = CH₃, X' = Cl   R = Si(CH₃)₃, R' = CH₃, X' = Cl
R = H, R' = CH₃, X' = F    R = Si(CH₃)₃, R' = CH₃, X' = F

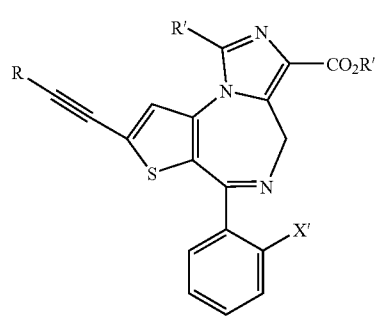

R = H, R' = Et, X' = H
R = H, R' = Et, X' = Br
R = H, R' = Et, X' = Cl
R = H, R' = Et, X' = F

Generally, we contemplate all analogs of 1–4 above with X'=F, Cl, Br, NO₂ and/or R''=CH₃, isopropyl, t-butyl, isoxazoles. Also, all analogs of R—C≡C— with R=t-butyl, isopropyl, cyclopropyl. We believe that replacement of the halogen atom in 1,4-benzodiazepines or the related triazolo-1,4-benzodiazepines at C(7) or C(8) generally results in anxiolytic activity with greatly decreased sedative/hypnotic/muscle relaxant activity or, in some cases, no sedative hypnotic activity compared to known agents.

-continued
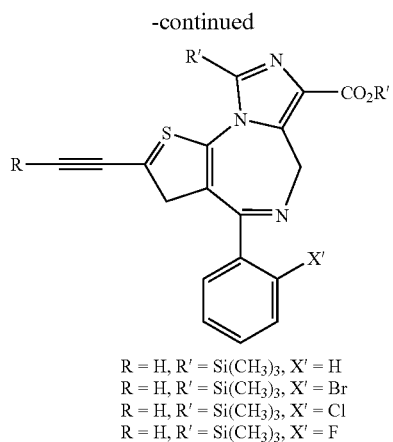
R = H, R' = Si(CH₃)₃, X' = H
R = H, R' = Si(CH₃)₃, X' = Br
R = H, R' = Si(CH₃)₃, X' = Cl
R = H, R' = Si(CH₃)₃, X' = F
All of the above claimed also with R' = t-butyl, isopropyl, isoxazole,
CH₂—△
All of the above claimed with this unit below CO₂R' replaced with
[isoxazole with R'']
R'' = CH₃, CH₂CH₃, iPr.
-continued
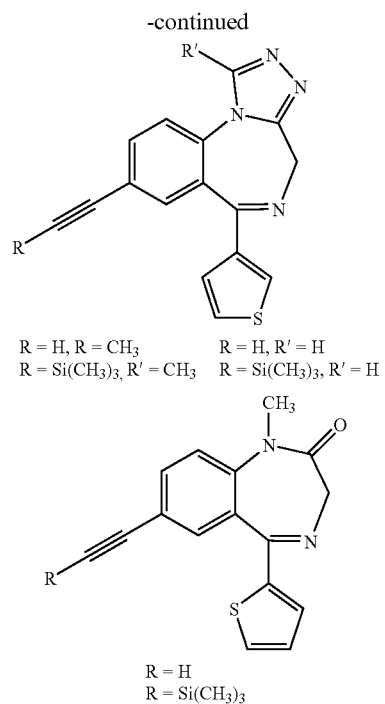
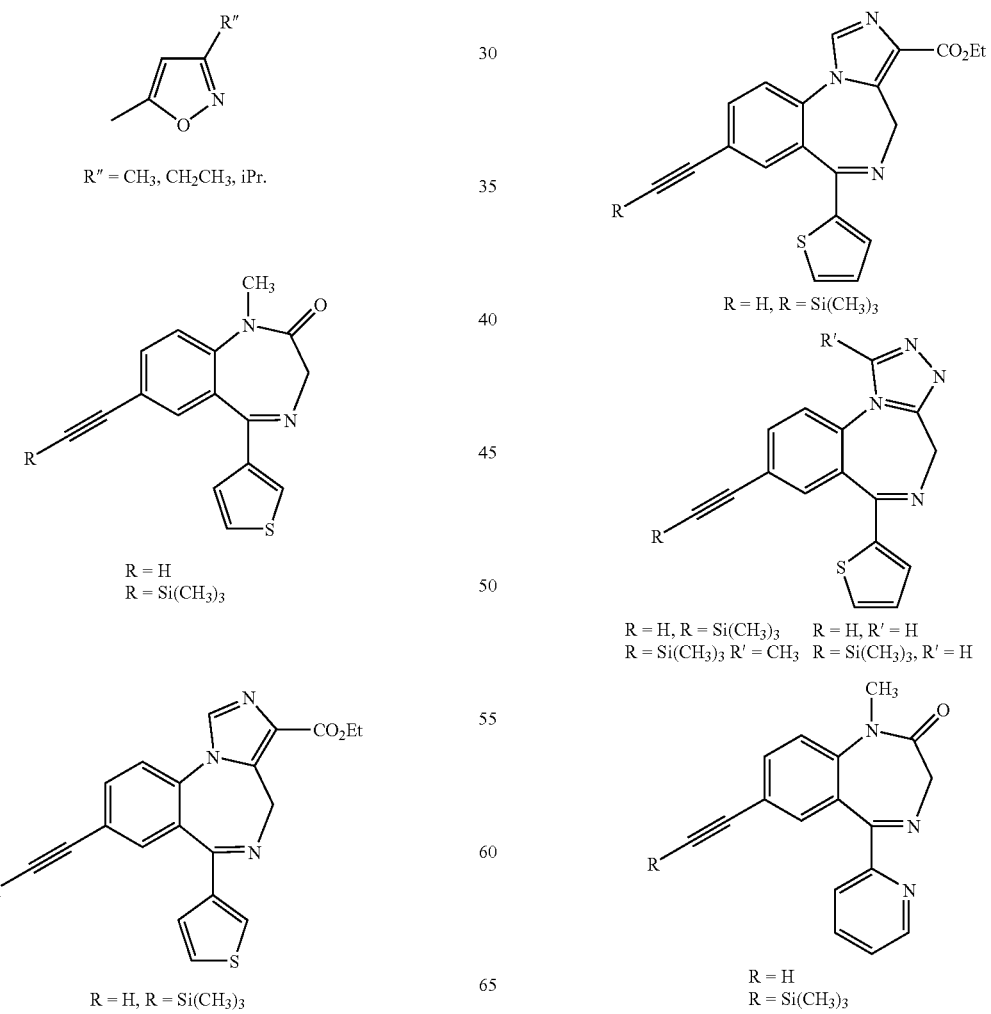

-continued
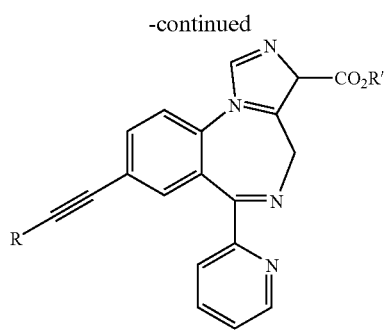
R = H, R' = Et
R = Si(CH₃)₃, R' = Et
R' = t-butyl, isopropyl, isoxazole, CH₂—cyclopropyl
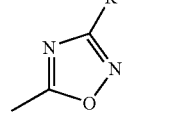
R'' = CH₃, CH₂CH₃, iPr.
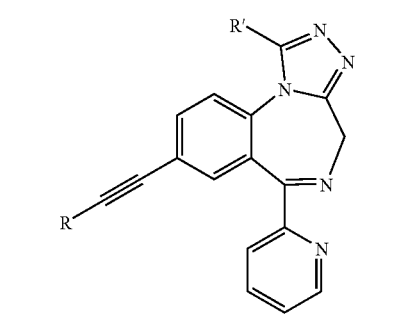
R = H, R' = CH₃     R = H, R' = H
R= Si(CH₃)₃, R' = CH₃    R = Si(CH₃)₃, R' = H
R = H, R' = CH₂CH₃    R = Si(CH₃)₃, R' = CH₂CH₃
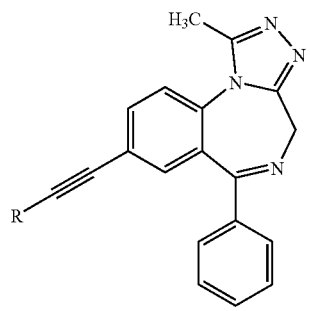
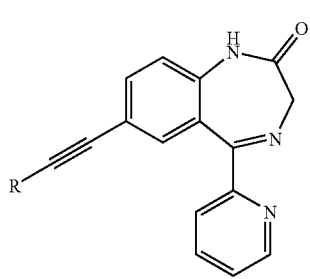
-continued
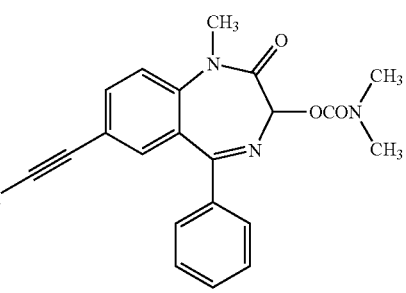
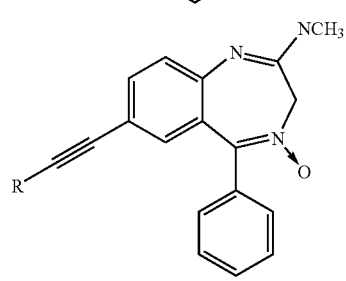
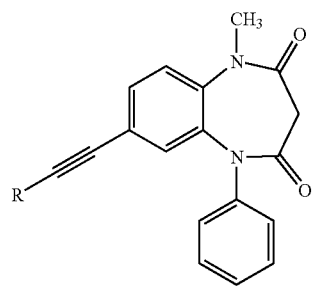
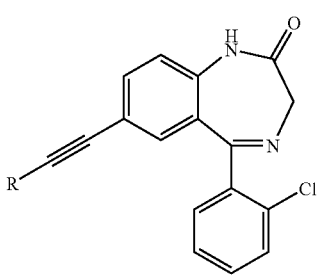
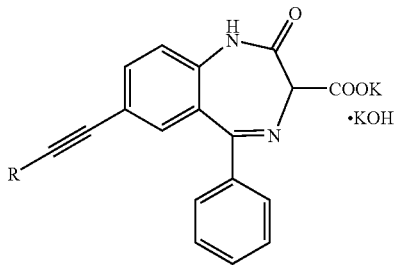
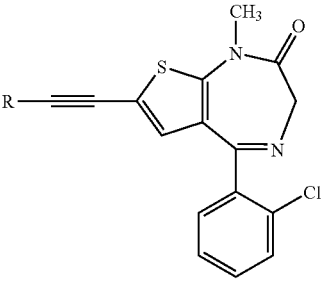

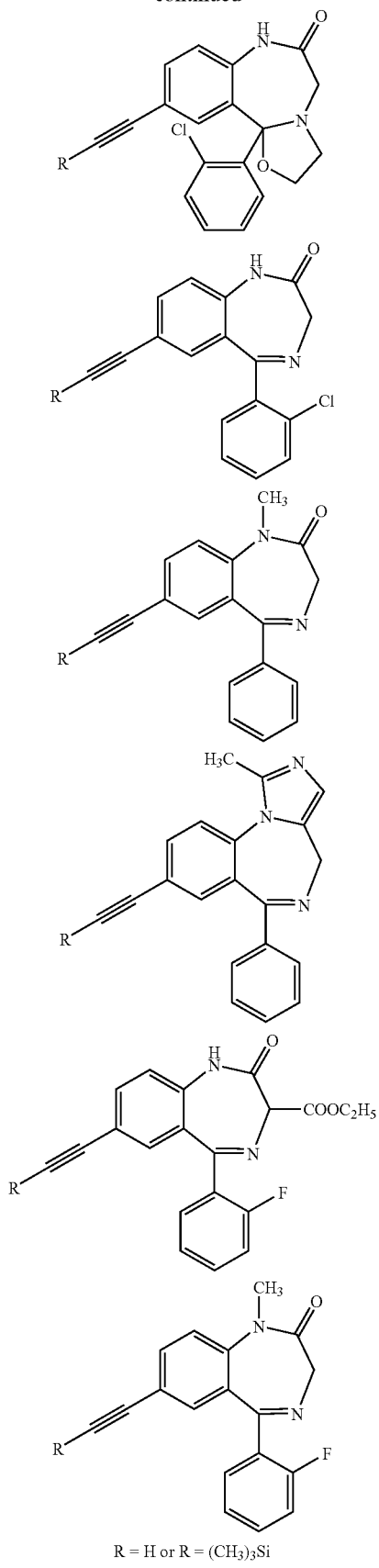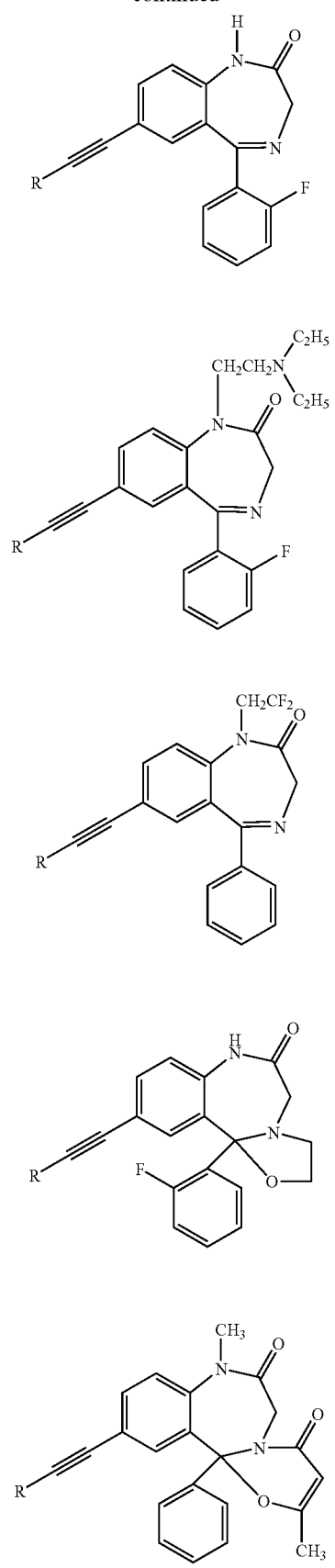
R = H or R = (CH₃)₃Si

-continued
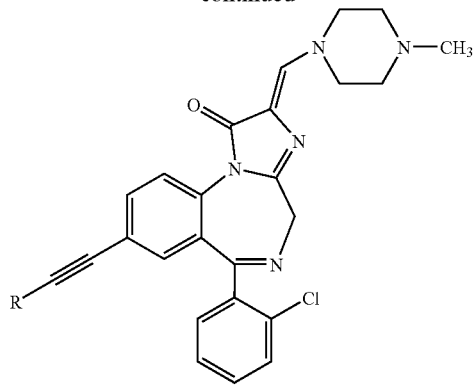
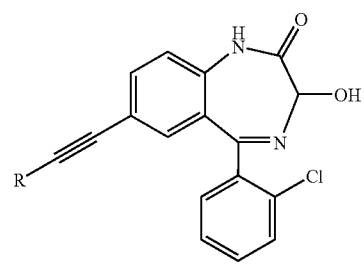
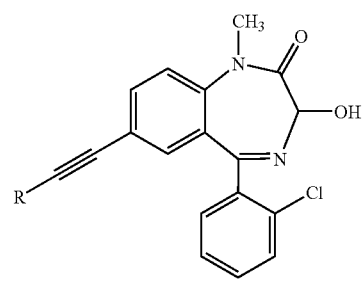
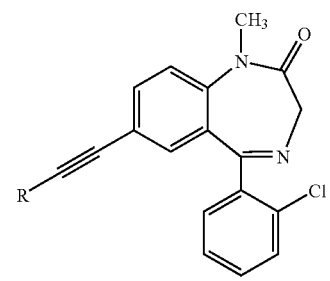
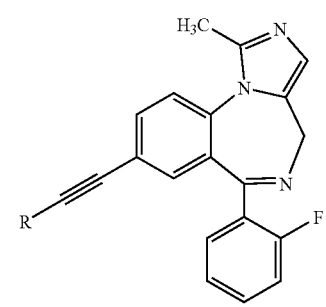
-continued
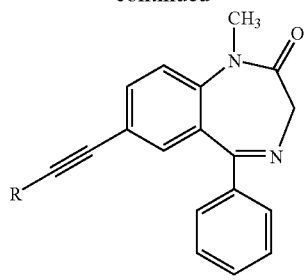
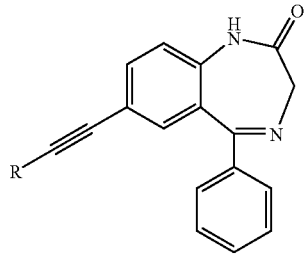
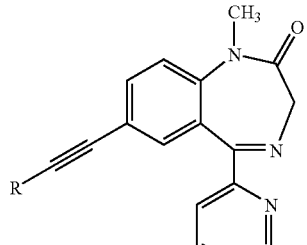
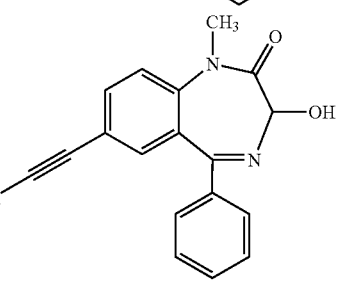
R = H, or R = (CH₃)₃Si
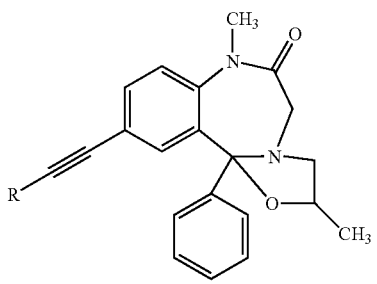
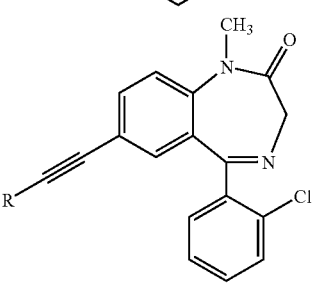

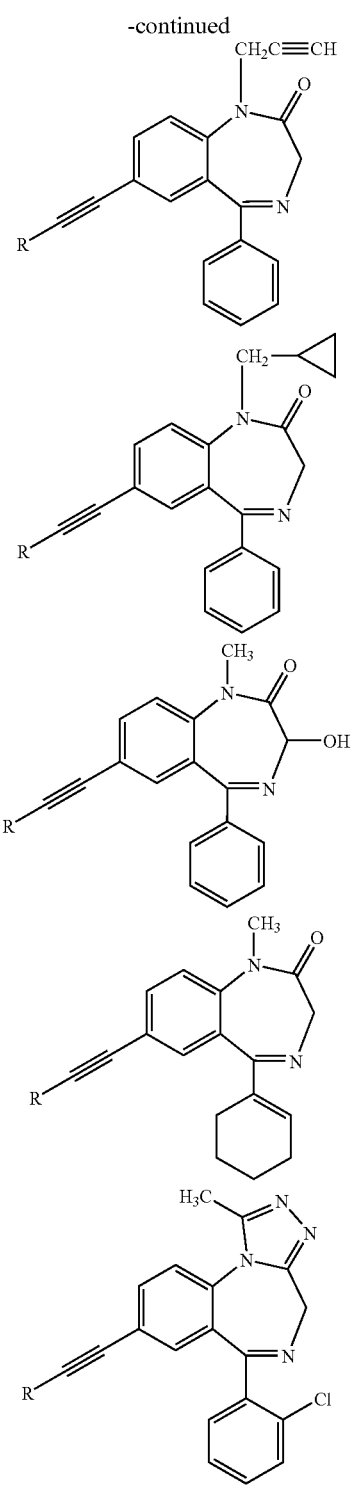

Experimental Methods

Situational Anxiety Model in Rats

Male Sprague-Dawley rats weighing 180-200 grams were purchased from Charles River Laboratories (Wilmington, Mass.). The rats were housed individually in suspended wire cages in a colony room maintained at constant temperature (21±2° C.) and humidity (50±10%). The room was illuminated 12 hours per day (lights on at 0600 h). The rats had ad libitum access to food and water throughout the study. Behavioral studies were conducted between 0600 and 1300 hours. Testing: A modification of the Defensive Withdrawal procedure, as originally described by Takahashi et al. (1989), was employed. The testing apparatus consisted of an opaque plexiglass open field (106 cm length×92 cm width× 50 cm height), containing a cylindrical galvanized chamber (14 cm length, 10 cm diameter) that was positioned lengthwise against one wall, with the open end 40 cm from the corner. The open field was illuminated by a 60 watt incandescent bulb, and illumination was titrated by a powerstat transformer to a 23 lux reading at the entrance to the cylinder. Rats were habituated to handling by gently stroking their dorsal surface for approximately one minute daily for 5-6 consecutive days before testing. To initiate testing of exploratory behavior in this unfamiliar environment, each rat was placed within the cylinder, which was then secured to the floor. Behavior was assessed for 15 minutes by a trained observer (unaware of treatment assignment) via a video monitor in an adjacent room. The latency to emerge from the cylinder, defined by the placement of all four paws into the open field, was recorded for each rat. After testing each rat, the plexiglass chamber and the cylinder were cleaned with 1.0% glacial acetic acid to prevent olfactory cues from influencing the behavior of subsequently tested rats. Drug Administration: All drugs were administered PO 20-60 minutes prior to behavioral testing. Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at $p<0.05$.

Protection from Pentylenetetrazole-Induced Seizures

Male CF1 mice weighing 20-22 g at the time of the experiment were purchased from Charles River Laboratories (Wilmington, Mass.). Pentylenetetrazole (Sigma Chemical Co.) was administered at 125 mg/kg s.c. The number of animals surviving was recorded at 30 minutes and 60 minutes after administration of pentylenetetrazole. Drug Administration: All drugs were administered PO 60 minutes before administration of pentyenetetrazole. Data Analysis: The data are presented as the percent of animals protected from death. The data were analyzed by Chi Square statistics. The significance level was set at $p<0.05$.

Protection from Electroshock-Induced Seizures

Male CF1 mice weighing 20-22 g at the time of the experiment were purchased from Charles River Laboratories (Wilmington, Mass.). Electroshock is administered using a Ugo Basile ECT, Unit 7801 seizure apparatus (Ugo Basile, Italy) and corneal electrodes soaked in 0.9% saline. Mice received a shock of 30 mA for 0.3 seconds. Drug Administration: All experimental compounds were administered PO 60 minutes before administration of electroshock. Data Analysis: The data are presented as the percent of animals protected from the hind-limb extensor component of the seizure. The data were analyzed by Chi Square statistics. The significance level was set at $p<0.05$.

Open-Field Locomotor Activity in Rats

Male Sprague-Dawley rats, weighing 250-290 grams at the beginning of the experiment were purchased from Charles River Laboratories (Wilmington, Mass.). The animals were housed in groups of four in a colony room maintained at constant temperature (21±2° C.) and humidity (50±10%). The room was illuminated 12 hours per day (lights on at 0600 h). The rats had ad libitum access to food and water. The testing apparatus consisted of plexiglas chambers (42×42×30 cm) equipped with Digiscan activity monitors (Omnitech Electronics, Columbus, Ohio) that detect interruptions of 16 photobeams spaced 2.5 cm apart and 2.5 cm above the floor. Horizontal activity was monitored for 60 minutes. Drug Administration: All drugs were administered PO 20-60 minutes before behavioral testing. Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at p<0.05.

Rotorod Performance in Rats

Male Sprague-Dawley rats, weighing 180-200 grams at the beginning of the experiment were purchased from Charles River Laboratories (Wilmington, Mass.). The animals were housed in groups of four in a colony room maintained at constant temperature (21±2° C.) and humidity (50±10%). The room was illuminated 12 hours per day (lights on at 0600 h). The rats had ad libitum access to food and water. The degree of muscle coordination or balance (i.e., ataxia) was determined using a standard accelerating rotorod treadmill (Ugo Basile, Comerio-Varese, Italy or Columbus Instruments, Columbus, Ohio) that was 6 cm in diameter, 24 cm above the base, and run from an initial speed of 2 rpm to a maximum speed of 20 rpm. The time each animal remained on the rotating rod was automatically recorded, up to a maximum of 5 minutes. Each rat had three pretest acclimation trials, and the latency from the third trial was used to counterbalance rats for subsequent drug testing. Drug Administration: All drugs were administered PO 20-60 minutes before behavioral testing. Data Analysis: Results were expressed as the mean±1 SEM. All data were subjected to analysis of variance (ANOVA) followed by individual mean comparisons using Fisher's Least Significant Difference Test (Kirk, 1968) where appropriate. The significance level was set at p<0.05.

Discriminative Stimulus Effects of Chlordiazepoxide in Rats

Male Sprague-Dawley rats weighing 240 to 300 g at the start of the experiment were purchased from Charles River Laboratories (Wilmington, Mass.). Animals were housed singly in hanging wire cages in a room maintained at constant temperature (21-23° C.) and humidity (50±10%) and illuminated 12 hours per day (lights on at 0600 h). Throughout the study rats were restricted to 12 g of laboratory rodent chow pellets (Bio-Serv, Frenchtown, N.J.) per day, while access to water was unlimited. All training and testing was done Monday through Friday of each week.

Twelve model E10-10 Coulbourn operant chambers (28× 26×31 cm) were housed in light-proof, sound-attenuated, and fan-ventilated chambers. Each operant chamber was equipped with two non-retractable levers, requiring a downward force equivalent to 15 g (0.15 N), that were mounted 3 cm from the side wall, 3 cm above the metal grid floor, and 5 cm from a centrally placed dipper that delivered one 45 mg food pellet (Dustless Precision Pellets, Bio-Serv, Frenchtown, N.J.). The experimental chambers were connected to a Micro PDP11/73 computer using a LAB LINC interface. A SKED-11 operating system (State System, Kalamazoo, Mich.) was used to record and control behavior. Discrimination training: After habituation to the operant chamber, rats were trained to alternate daily between response levers on a Fixed Ratio 1 (FR 1) schedule of reinforcement. Once lever pressing was well established, the reinforcement contingency was increased incrementally to an FR 10 schedule, while maintaining the lever alternation. Next, rats were trained to discriminate between drug (5.0 mg/kg, IP, chlordiazepoxide) and drug vehicle (0.9% saline). Half of the rats were randomly assigned the left lever as "drug-correct" and the right lever as "saline-correct." The lever assignments were reversed for the remaining animals. Every tenth response on the drug-correct lever was reinforced on days when the rats were pretreated with drug, whereas every tenth response on the opposite lever was reinforced after saline injections. In each 2-week period there were 5 drug days and 5 saline days, with the constraint that there not be more than 3 consecutive drug or vehicle days. Discrimination sessions were continued until each rat reached the criterion of no more than three incorrect responses before first food presentation in 9 out of 10 consecutive sessions. Test sessions: Once criterion for testing was met, stimulus substitution tests were conducted on Friday of each week. Test sessions were 10 minutes in duration. During the test sessions, the lever on which the rat first responded 10 times resulted in reinforcement and subsequent FR 10 reinforcement was made contingent upon pressing this "selected" lever. The lever on which the rat first made 10 responses (the selected lever) and the total number of responses in the session were recorded. On Monday through Thursday of each week, training sessions were conducted to ensure that criterion for testing was met. If any rat failed to meet the criterion for testing, testing with that animal was postponed and discrimination training continued until the performance criterion was attained. Data analysis: Drug discrimination results are expressed as the percentage of animals selecting the chlordiazepoxide-correct lever.

REFERENCES

Kirk R E (1968) Experimental Design: Procedures for the Behavioral Sciences. Brooks/Cole, Belmont, Calif.

Takahashi L K, Kalin N H, Vanden Burgt J A, Sherman J E (1989) Corticotropin-releasing factor modulates defensive-withdrawal and exploratory behavior in rats. Behav Neurosci 103:648-654

Experimental Results

Table 1 (below) shows ratios of lowest effective anxiolytic doses in the situational anxiety (SA) assay compared with lowest effective doses producing side effects in three different models: locomotor activity (LMA), rotorod (RR), and chlordiazepoxide-like subjective effects as measured by the drug discrimination method (DD).

Table 2 (below) shows effective doses in a model of epilepsy (pentylenetetrazole-induced seizures) in mice (mg/kg, PO) for QH-ii-066, Xli-JY-DMH, and XHe-ii-053 in comparison with diazepam, triazolam, and DM-1-070.

EXAMPLE 1

Situational Anxiety in Rats

Rats were handled daily for at least 5-6 days. They were then placed in a dark cylinder in an illuminated open field. The time for the rats to exit the dark cylinder was then measured. Vehicle-treated animals remain within the dark cylinder for 10-15 minutes (total test duration is 15 minutes). This high latency to exit the dark chamber is an index of a heightened state of anxiety. Compounds with anxiolytic efficacy reduce latency to exit the dark chamber. Table 1 shows that QH-ii-066, XLi-JY-DMH, and XHe-ii-053 show anxiolytic effects in the situational anxiety test at doses>100-fold lower than doses producing sedative and ataxic effects (see examples 2 and 3).

EXAMPLE 2

Locomotor Activity in Rats

Rats were placed in an open field and the total distance covered by the rat was measured. The test duration was 60 minutes. Compounds producing sedative effects decrease the distance covered. Table 1 shows that QH-ii-066, XLi-JY-DMH, and XHe-ii-053 are less effective in producing sedative or hypnotic effects than diazepam or triazolam.

EXAMPLE 3

Rotorod Performance in Rats

Rats were placed on a slowly rotating rod and the speed of rotation was gradually increased. The time on the rod for each rat was recorded. Compounds producing ataxia (motor incoordination) decrease the time spent on the rod compared with vehicle-treated animals. Table 1 shows that QH-ii-066, XLi-JY-DMH, and XHe-ii-053 are less potent in producing ataxia than diazepam or triazolam. Thus, they are likely better drugs clinically because they have decreased side effects [decreased sedation (example 2) and ataxia (example 3)].

EXAMPLE 4

Drug Discrimination in Rats

Animals are taught to emit one response if they just received drug and a different response if they just received saline. The animals learn to discriminate between a "drug state" and a "no drug state". The rats were trained to discriminate between a state induced by a typical benzodiazepine chlordiazepoxide (CDP; "drug state") and a state induced by vehicle (methocel: "no drug state"). Table 1 shows that QH-ii-066, XLi-JY-DMH, and XHe-ii-053 are less potent in producing CDP-like effects than diazepam or triazolam and thus may have reduced abuse potential compared with CDP.

EXAMPLE 5

Seizure Protection in Mice

Mice treated with certain compounds of the present invention were subjected to pentylenetetrazole (PTZ) at 125 mg/kg to induce seizures. The percent of animals protected from death within one hour of PTZ was measured. Table 2 shows that QH-ii-066 and XLi-JY-DMH have anticonvulsant effects against PTZ-induced seizures at doses comparable to those for diazepam and triazolam. Table 2 also shows that XHe-ii-053 is effective against PTZ-induced seizures.

TABLE 1

|  | Antianxiety/sedation | Antianxiety/ataxia | Antianxiety/abuse liability |
|---|---|---|---|
| Diazepam | 10 | 100 | 5 |
| QH-ii-066 | 100 | >100 | 30 |

TABLE 1-continued

|  | Antianxiety/sedation | Antianxiety/ataxia | Antianxiety/abuse liability |
|---|---|---|---|
| Triazolam | 300 | 100 | 30 |
| XLi-JY-DMH | 10000 | 10000 | 1000 |
| DM-i-070 | >100 | >100 | 10 |
| XHe-ii-053 | >300 | >300 | >300 |

TABLE 2

|  | PTZ Seizures (mg/kg, PO) |
|---|---|
| Diazepam | <10 |
| QH-ii-066 | <30 |
| Triazolam | <1.0 |
| XLi-JY-DMH | <1.0 |
| DM-i-070 | <100 |
| XHe-ii-053 | ≦100 |

REFERENCES

1. Sternbach, L. H.; Fryer, R. I.; Metlesics, W.; Reeder, E.; Sach, G.; Saucy, G.; Stempel, A. *J. Org. Chem.* 1962, 27, 3788-3796.
2. Gu, Q.; Wang, G.; Dominguez, C.; Costa, B. R.; Rice, K. C.; Skolnick, P. *J. Med. Chem.* 1993, 36, 1001-1006.
3. Ning, R. Y.; Fryer, R. I.; Madan, P. B.; Sluboski, B. C. *J. Org. Chem.* 1976, 41, 2724-2727.
4. Liu, R.; Zhang, P.; Skolnick, P.; McKernan, R; Cook, J. M. *J. Med. Chem.* 1996, 39, 1928-1934.
5. Austin, W. B.; Bilow, N.; Kelleghan, W. J.; Lau, K. S. Y. *J. Org. Chem.* 1981, 46, 2280-2286.
6. Sternbach, L. H.; Reeder, E.; Archer, G. A. *J. Org. Chem.* 1963, 28, 2456-2459.
7. He, X. *Ph.D. Thesis*, UW-Milwaukee, 2000.
8. Heck, R. F. *Palladium Reagents in Organic Synthesis*; Academic Press, Orlando, Fla.: Academic Press, 1985.
9. Bogatskii, A. V.; Andronati, S. A.; Vikhlyaev, Yu. I.; Voronina, T. A.; Yakubovskaya, L. N.; Ben'ko, A. V. *Pharm. Chem. J. (Engl. Transl.)* 1977, 11, 1520-1525
10. Vejdelek, Zdenek; Protiva, Miroslav. *Collect. Czech. Chem. Commun.* 1983, 48, 1477-1482
11. Hester, J. B.; Ludens, J. H.; Emmert, D. E.; West, B. E. *J. Med. Chem.* 1989, 32, 1157-1163.
12. Fryer, R. I.; Kudzma, L. K; Gu, Z.; Lin, K. *J. Org. Chem.* 1991, 56, 3715-3719.
13. Patent, Hoffmann-LaRoche, 1963, DE 1145625.
14. Patent, Hoffmann-LaRoche, 1958, U.S. Pat. No. 2,893,992.
15. G. A. Archer and L. H. Sternbach, *J. Org. Chem.*, 29, 231 (1964).
16. Fryer, R. I.; Zhang, P.; Rios, R. *Synth. Commun.* 1993, 23, 985-992.
17. U.S. Pat. No. 3,886,141, 1975.

The invention claimed is:
1. A compound of formula V, or a salt thereof,

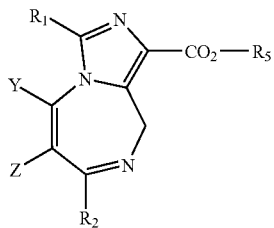 (V)

wherein:
- Y and Z are taken together with the two intervening carbon atoms to form a thienyl ring, which is substituted at the C(8) position with at least the substituent —C≡C—R, where R is H, Si(CH$_3$)$_3$, t-butyl, isopropyl, methyl, or cyclopropyl;
- R$_1$ is one of H, CH$_3$, CF$_3$, CH$_2$CF$_3$, CH$_2$CH$_3$, CH$_2$C≡CH or cyclopropyl;
- R$_2$ is a substituted or unsubstituted at least partially unsaturated 5 membered or 6 membered carbocyclic ring or 5 membered or 6 membered heterocyclic ring having at least one heteroatom selected from N, O and S, wherein if substituted the substituent is one or more of F, Cl, Br, or NO$_2$ at the 2'-position;
- R$_5$ is a branched or straight chain C$_1$ to C$_4$ halogenated or unhalogenated alkyl or a methyl cyclopropyl.

2. The compound according to claim 1, wherein said compound is:

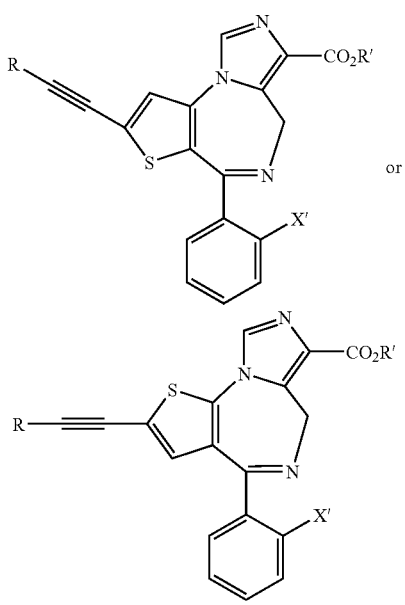

wherein
R is H or Si(CH$_3$)$_3$
R' is one of ethyl, t-butyl, isopropyl, isoxazole,

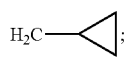

and
X' is H, NO$_2$, Br, Cl or F.

3. The compound according to claim 2, wherein R is hydrogen, R' is ethyl and X' is H.

4. The compound according to claim 2, wherein the CO$_2$R' is replaced with

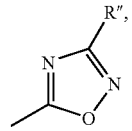

wherein R" is CH$_3$, CH$_2$CH$_3$ or iPr.

5. A compound of formula VI, or a salt thereof,

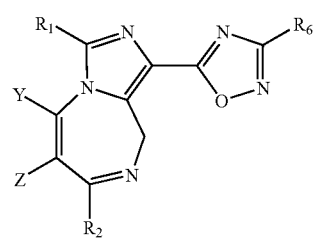 (VI)

wherein:
- Y and Z are taken together with the two intervening carbon atoms to form a thienyl ring, which is substituted at the C(8) position with at least the substituent —C≡C—R, where R is H, Si(CH$_3$)$_3$, t-butyl, isopropyl, methyl, or cyclopropyl;
- R$_1$ is one of H, CH$_3$, CF$_3$, CH$_2$CH$_3$, CH$_2$CF$_3$, CH$_2$C≡CH or cyclopropyl;
- R$_2$ is a substituted or unsubstituted at least partially unsaturated 5 membered or 6 membered carbocyclic ring or 5 membered or 6 membered heterocyclic ring having at least one heteroatom selected from N, O and S, wherein if substituted the substituent is one or more of F, Cl, Br, or NO$_2$ at the 2'-position;
- R$_6$ is a branched or straight chain C$_1$ to C$_4$ alkyl or a methyl cyclopropyl.

6. A compound of formula IX, or a salt thereof,

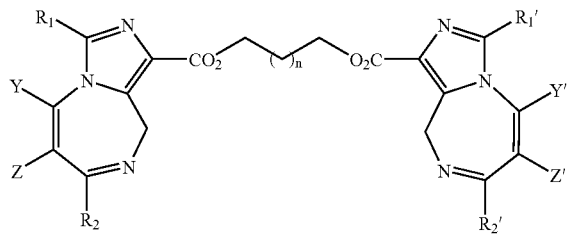 (IX)

wherein:
- n is 0 to 4;
- Y and Z are taken together with the two intervening carbon atoms to form a thienyl ring, which is substituted at the C(8) position with at least the substituent —C≡C—R, where R is H, Si(CH$_3$)$_3$, t-butyl, isopropyl, methyl, or cyclopropyl;
- Y' and Z' are taken together with the two intervening carbon atoms to form a thienyl ring, which is substituted at the C(8)' position with at least the substituent —C≡C—R', where R' is H, Si(CH$_3$)$_3$, t-butyl, isopropyl, methyl, or cyclopropyl;

$R_1$ and $R_1'$ are independently one of H, $CH_3$, $CF_3$, $CH_2CF_3$, $CH_2CH_3$, $CH_2C\equiv CH$ or cyclopropyl;

$R_2$ and $R_2'$ are independently a substituted or unsubstituted at least partially unsaturated 5 membered or 6 membered carbocyclic ring or 5 membered or 6 membered heterocyclic ring having at least one heteroatom selected from N, O and S, wherein if substituted the substituent is one or more of F, Cl, Br, or $NO_2$ at the 2'-position.

7. A compound of formula X, or a salt thereof,

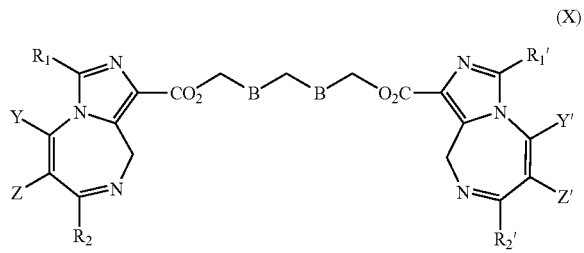

(X)

wherein:

Y and Z are taken together with the two intervening carbon atoms to form a thienyl ring, which is substituted at the C(8) position with at least the substituent —C≡C—R, where R is H, $Si(CH_3)_3$, t-butyl, isopropyl, methyl, or cyclopropyl;

Y' and Z' are taken together with the two intervening carbon atoms to form a thienyl ring, which is substituted at the C(8)' position with at least the substituent —C≡C—R', where R' is H, $Si(CH_3)_3$, t-butyl, isopropyl, methyl, or cyclopropyl;

$R_1$ and $R_1'$ are independently one of H, $CH_3$, $CF_3$, $CH_2CH_3$, $CH_2CF_3$, $CH_2C\equiv CH$ or cyclopropyl;

$R_2$ and $R_2'$ are independently a substituted or unsubstituted at least partially unsaturated 5 membered or a 6 membered carbocyclic ring or 5 membered or 6 membered heterocyclic ring having at least one heteroatom selected from N, O and S, wherein if substituted the substituent is one or more of F, Cl, Br, or $NO_2$ at the 2'-position;

B is O or NH and wherein —$BCH_2B$— is optionally replaced with —$N(R_7)$—$N(R_7)$—, where $R_7$ is one of H, $CH_3$, alkyl, or cycloalkyl.

8. A compound of formula XI, or a salt thereof,

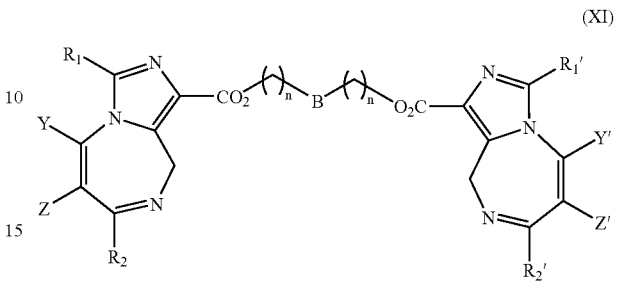

(XI)

wherein:

n is 1 or 2

Y and Z are taken together with the two intervening carbon atoms to form a thienyl ring, which is substituted at the C(8) position with at least the substituent —C≡C—R, where R is H, $Si(CH_3)_3$, t-butyl, isopropyl, methyl, or cyclopropyl;

Y' and Z' are taken together with the two intervening carbon atoms to form a thienyl ring, which is substituted at the C(8)' position with at least the substituent —C≡C—R', where R' is H, $Si(CH_3)_3$, t-butyl, isopropyl, methyl, or cyclopropyl;

$R_1$ and $R_1'$ are independently one of H, $CH_3$, $CF_3$, $CH_2CH_3$, $CH_2CF_3$, $CH_2C\equiv CH$ or cyclopropyl;

$R_2$ and $R_2'$ are independently a substituted or unsubstituted at least partially unsaturated 5 membered or 6 membered carbocyclic ring or 5 membered or 6 membered heterocyclic ring having a heteroatom selected from N, O and S, wherein if substituted the substituent is one or more of F, Cl, Br, or $NO_2$ at the 2'-position;

B is O, NH, or —$N(R_7)$—$N(R_7)$—, where $R_7$ is one of H, $CH_3$, alkyl, or cycloalkyl.

* * * * *